US011578373B2

(12) United States Patent
Dobak, III et al.

(10) Patent No.: US 11,578,373 B2
(45) Date of Patent: Feb. 14, 2023

(54) GENE CLASSIFIERS AND USES THEREOF IN SKIN CANCERS

(71) Applicant: DermTech, Inc., La Jolla, CA (US)

(72) Inventors: John Daniel Dobak, III, La Jolla, CA (US); Burkhard Jansen, La Jolla, CA (US); Zuxu Yao, San Diego, CA (US)

(73) Assignee: DermTech, Inc., San Diego, CA (US)

( * ) Notice: Subject to any disclaimer, the term of this patent is extended or adjusted under 35 U.S.C. 154(b) by 0 days.

(21) Appl. No.: 16/828,289

(22) Filed: Mar. 24, 2020

(65) Prior Publication Data

US 2020/0308657 A1    Oct. 1, 2020

Related U.S. Application Data

(60) Provisional application No. 62/824,163, filed on Mar. 26, 2019.

(51) Int. Cl.
*C12Q 1/6886* (2018.01)
*A61K 45/06* (2006.01)

(52) U.S. Cl.
CPC ............ *C12Q 1/6886* (2013.01); *A61K 45/06* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,122,947 A | 10/1978 | Falla |
| 4,365,409 A | 12/1982 | Riley et al. |
| 4,458,066 A | 7/1984 | Caruthers et al. |
| 4,537,776 A | 8/1985 | Cooper |
| 4,683,195 A | 7/1987 | Mullis et al. |
| 4,683,202 A | 7/1987 | Mullis |
| 4,836,217 A | 6/1989 | Fischer |
| 4,851,510 A | 7/1989 | Khan |
| 4,971,800 A | 11/1990 | Chess et al. |
| 5,190,049 A | 3/1993 | Briggs et al. |
| 5,460,939 A | 10/1995 | Hansbrough et al. |
| 5,493,009 A | 2/1996 | Ferrone |
| 5,583,032 A | 12/1996 | Torrence et al. |
| 5,654,286 A | 8/1997 | Hostetler |
| 5,753,612 A | 5/1998 | Mitrani |
| 5,786,146 A | 7/1998 | Herman et al. |
| 5,807,522 A | 9/1998 | Brown et al. |
| 5,811,239 A | 9/1998 | Frayne |
| 5,858,683 A | 1/1999 | Keesee et al. |
| 5,921,396 A | 7/1999 | Brown, Jr. |
| 5,962,477 A | 10/1999 | Mak |
| 5,972,602 A | 10/1999 | Hyland et al. |
| 5,989,815 A | 11/1999 | Skolnick et al. |
| 6,017,704 A | 1/2000 | Herman et al. |
| 6,033,854 A | 3/2000 | Kurnit et al. |
| 6,054,277 A | 4/2000 | Furcht et al. |
| 6,056,859 A | 5/2000 | Ramsey et al. |
| 6,106,732 A | 8/2000 | Johnston et al. |
| 6,129,983 A | 10/2000 | Schuemann et al. |
| 6,176,836 B1 | 1/2001 | Trudil et al. |
| 6,180,349 B1 | 1/2001 | Ginzinger et al. |
| 6,200,756 B1 | 3/2001 | Herman et al. |
| 6,203,987 B1 | 3/2001 | Friend et al. |
| 6,265,171 B1 | 7/2001 | Herman et al. |
| 6,306,597 B1 | 10/2001 | Macevicz |
| 6,312,909 B1 | 11/2001 | Shyjan |
| 6,331,393 B1 | 12/2001 | Laird et al. |
| 6,355,439 B1 | 3/2002 | Chung et al. |
| 6,410,019 B1 | 6/2002 | De Simone et al. |
| 6,410,240 B1 | 6/2002 | Hodge et al. |
| 6,447,463 B1 | 9/2002 | Borkowski |
| 6,551,799 B2 | 4/2003 | Gurney et al. |
| 6,720,145 B2 | 4/2004 | Rheins et al. |
| 6,726,971 B1 | 4/2004 | Wong |
| 6,797,470 B2 | 9/2004 | Barany et al. |
| 6,891,022 B1 | 5/2005 | Stewart et al. |
| 6,949,338 B2 | 9/2005 | Rheins et al. |
| 7,037,687 B2 | 5/2006 | Williams et al. |
| 7,083,917 B2 | 8/2006 | Barany et al. |
| 7,166,434 B2 | 1/2007 | Barany et al. |
| 7,169,560 B2 | 1/2007 | Lapidus et al. |
| 7,183,057 B2 | 2/2007 | Benson |
| 7,186,512 B2 | 3/2007 | Martienssen et al. |
| 7,232,656 B2 | 6/2007 | Balasubramanian et al. |
| 7,247,426 B2 | 7/2007 | Yakhini et al. |

(Continued)

FOREIGN PATENT DOCUMENTS

CN    1612936 A    5/2005
CN    106119242 A    11/2016

(Continued)

OTHER PUBLICATIONS

Juppner Functional properties of the PTH/PTHrP receptor (1995) Bone vol. 17 No. 2 Supplement 39S-42S. (Year: 1995).*
Sugaya et al. Serum Interleukin-15 Levels are not Elevated in Patients with Stage I and II Mycosis Fungoides (2000) Acta Derm Venereol Letters to the Editor 80, 455. (Year: 2000).*
UniProt—LEF1 (Year: 2000).*
Dulmage et al. Lessons learned from gene expression profiling of cutaneous T-cell lymphoma (2013) Brit J of Derm 169:6, 1188-1197 (Year: 2013).*
Litvinov et al. Gene expression analysis in Cutaneous T-Cell Lymphoma (CTCL) highlights disease heterogeneity and potential diagnostic and prognostic indicators (2017) Oncoimmunology 6:5 e136618, 14 pages. (Year: 2017).*

(Continued)

*Primary Examiner* — Katherine D Salmon
(74) *Attorney, Agent, or Firm* — Wilson Sonini Goodrich & Rosati

(57) ABSTRACT

Disclosed herein, in certain embodiments, are methods of detecting the presence of a skin cancer based on molecular risk factors. In some instances, the skin cancer is cutaneous T cell lymphoma (CTCL). In some cases, the skin cancer is mycosis fungoides (MF) or Sézary syndrome (SS).

18 Claims, 9 Drawing Sheets

(56) References Cited

U.S. PATENT DOCUMENTS

| | | |
|---|---|---|
| 7,267,951 B2 | 9/2007 | Alani et al. |
| 7,297,480 B2 | 11/2007 | Vogt |
| 7,320,865 B2 | 1/2008 | Barany et al. |
| 7,332,285 B2 | 2/2008 | Barany et al. |
| 7,364,858 B2 | 4/2008 | Barany et al. |
| 7,429,453 B2 | 9/2008 | Barany et al. |
| 7,459,274 B2 | 12/2008 | Lakey et al. |
| 7,553,627 B2 | 6/2009 | Laird et al. |
| 7,598,035 B2 | 10/2009 | Macevicz |
| 7,611,869 B2 | 11/2009 | Fan |
| 7,615,349 B2 | 11/2009 | Riker et al. |
| 7,645,596 B2 | 1/2010 | Williams et al. |
| 7,662,558 B2 | 2/2010 | Liew |
| 7,700,324 B1 | 4/2010 | Issa et al. |
| 7,769,400 B2 | 8/2010 | Backholm et al. |
| 7,771,950 B2 | 8/2010 | Wohlgemuth et al. |
| 7,901,880 B2 | 3/2011 | Jeddeloh et al. |
| 7,910,296 B2 | 3/2011 | Jeddeloh et al. |
| 7,919,246 B2 | 4/2011 | Lai et al. |
| 7,921,999 B1 | 4/2011 | Kimball |
| 7,972,788 B2 | 7/2011 | Miyata et al. |
| 7,989,165 B2 | 8/2011 | Benson |
| 8,067,173 B2 | 11/2011 | Liew |
| 8,389,215 B2 | 3/2013 | Krueger et al. |
| 8,492,102 B2 | 7/2013 | Kashani-Sabet et al. |
| 8,541,170 B2 | 9/2013 | Kennedy et al. |
| D692,149 S | 10/2013 | Uematsu |
| D692,152 S | 10/2013 | Inoo |
| D704,343 S | 5/2014 | Inoo et al. |
| 8,729,252 B2 | 5/2014 | Himmelreich et al. |
| 9,057,109 B2 | 6/2015 | Chang |
| D738,514 S | 9/2015 | Tagami et al. |
| D747,455 S | 1/2016 | Uematsu |
| D857,212 S | 8/2019 | Sugaya et al. |
| 10,407,729 B2 | 9/2019 | Chang |
| 10,781,200 B2 | 9/2020 | McDonald et al. |
| D899,606 S | 10/2020 | Kang |
| D899,607 S | 10/2020 | Ryu |
| 10,852,307 B2 | 12/2020 | Leung et al. |
| 2001/0031481 A1 | 10/2001 | Liotta et al. |
| 2001/0051344 A1 | 12/2001 | Shalon et al. |
| 2002/0037538 A1 | 3/2002 | Trepicchio et al. |
| 2002/0086019 A1 | 7/2002 | Wolf et al. |
| 2002/0110824 A1 | 8/2002 | Rheins et al. |
| 2002/0115086 A1 | 8/2002 | Rheins et al. |
| 2002/0119471 A1 | 8/2002 | Rheins et al. |
| 2002/0127573 A1 | 9/2002 | Rheins et al. |
| 2002/0150918 A1 | 10/2002 | Rheins et al. |
| 2002/0165192 A1 | 11/2002 | Kerr et al. |
| 2003/0010888 A1 | 1/2003 | Shimada et al. |
| 2003/0032617 A1 | 2/2003 | Harel et al. |
| 2003/0037538 A1 | 2/2003 | Rendahl et al. |
| 2003/0044406 A1 | 3/2003 | Dingivan |
| 2003/0045810 A1 | 3/2003 | Borkowski |
| 2003/0049256 A1 | 3/2003 | Tobinick |
| 2003/0073888 A1 | 4/2003 | Blumenberg |
| 2003/0108896 A1 | 6/2003 | Vogt |
| 2003/0113906 A1 | 6/2003 | Sangha et al. |
| 2003/0133936 A1 | 7/2003 | Byrne et al. |
| 2003/0175736 A1 | 9/2003 | Chinnaiyan et al. |
| 2003/0207315 A1 | 11/2003 | Burmer et al. |
| 2003/0208138 A1 | 11/2003 | Olson |
| 2003/0224422 A1 | 12/2003 | Evans et al. |
| 2003/0224465 A1 | 12/2003 | Nevalainen et al. |
| 2003/0228617 A1 | 12/2003 | Aune et al. |
| 2004/0191782 A1 | 9/2004 | Wang |
| 2005/0069879 A1 | 3/2005 | Berlin |
| 2005/0221334 A1 | 10/2005 | Benson |
| 2005/0261210 A1 | 11/2005 | Bhatnagar et al. |
| 2006/0019256 A1 | 1/2006 | Clarke et al. |
| 2006/0019286 A1 | 1/2006 | Horvitz et al. |
| 2006/0040335 A1 | 2/2006 | Butt et al. |
| 2006/0182755 A1 | 8/2006 | Bodary-Winter et al. |
| 2006/0271309 A1 | 11/2006 | Showe et al. |
| 2006/0294615 A1 | 12/2006 | Lin |
| 2007/0059717 A1 | 3/2007 | Pascual et al. |
| 2007/0066967 A1 | 3/2007 | Sieckmann et al. |
| 2007/0077553 A1 | 4/2007 | Bentwich |
| 2007/0082347 A1 | 4/2007 | Lanchbury et al. |
| 2007/0087323 A1 | 4/2007 | Armitage et al. |
| 2007/0099209 A1 | 5/2007 | Clarke et al. |
| 2007/0179198 A1 | 8/2007 | Iwai et al. |
| 2007/0243537 A1 | 10/2007 | Tuck et al. |
| 2007/0281314 A1 | 12/2007 | Benson |
| 2008/0032293 A1 | 2/2008 | Szabo et al. |
| 2008/0070883 A1 | 3/2008 | Nagpal |
| 2008/0131902 A1 | 6/2008 | Maor et al. |
| 2008/0138819 A1 | 6/2008 | Vogt |
| 2008/0254464 A1 | 10/2008 | Weindruch et al. |
| 2008/0260744 A1 | 10/2008 | Gaitanaris et al. |
| 2008/0274908 A1 | 11/2008 | Chang |
| 2009/0042204 A1 | 2/2009 | Thiboutot |
| 2009/0048510 A1 | 2/2009 | Miller et al. |
| 2009/0082265 A1 | 3/2009 | Bartel et al. |
| 2009/0111095 A1 | 4/2009 | Nishimura et al. |
| 2009/0155791 A1 | 6/2009 | Wojdacz et al. |
| 2009/0203639 A1 | 8/2009 | Van Criekinge et al. |
| 2009/0233319 A1* | 9/2009 | Katagiri et al. ....... G01N 33/00 |
| 2009/0246768 A1 | 10/2009 | Sawalha et al. |
| 2009/0263792 A1 | 10/2009 | Miyata et al. |
| 2009/0280479 A1 | 11/2009 | Hoon et al. |
| 2009/0298060 A1 | 12/2009 | Lal et al. |
| 2009/0299640 A1 | 12/2009 | Ellis et al. |
| 2009/0305242 A1 | 12/2009 | Miyata et al. |
| 2009/0318534 A1 | 12/2009 | Gallo et al. |
| 2010/0009375 A1 | 1/2010 | Sherman et al. |
| 2010/0086501 A1 | 4/2010 | Chang et al. |
| 2010/0105102 A1 | 4/2010 | Hanes et al. |
| 2010/0144836 A1 | 6/2010 | Van Engeland et al. |
| 2010/0233718 A1 | 9/2010 | Aubert et al. |
| 2010/0267033 A1 | 10/2010 | Abbas et al. |
| 2010/0279877 A1 | 11/2010 | Vogt |
| 2011/0033842 A1 | 2/2011 | Moon et al. |
| 2011/0040571 A1 | 2/2011 | Warren |
| 2011/0059113 A1 | 3/2011 | Celebi |
| 2011/0091384 A1 | 4/2011 | Alani et al. |
| 2011/0158953 A1 | 6/2011 | Scott |
| 2011/0159496 A1 | 6/2011 | Kashani-Sabet et al. |
| 2011/0160080 A1 | 6/2011 | Chang |
| 2011/0250251 A1 | 10/2011 | Maes et al. |
| 2011/0262464 A1 | 10/2011 | Chin et al. |
| 2011/0287034 A1 | 11/2011 | Frank et al. |
| 2012/0065086 A1 | 3/2012 | Benson |
| 2012/0071343 A1 | 3/2012 | Ma et al. |
| 2012/0094853 A1 | 4/2012 | Clark et al. |
| 2012/0171193 A1 | 7/2012 | Blaser et al. |
| 2012/0201750 A1 | 8/2012 | Ryu |
| 2013/0079423 A1 | 3/2013 | Abkevich et al. |
| 2013/0143747 A1 | 6/2013 | Gutin et al. |
| 2013/0244256 A1 | 9/2013 | Clarke et al. |
| 2013/0296185 A1 | 11/2013 | Benson |
| 2013/0302242 A1 | 11/2013 | Stone et al. |
| 2013/0344481 A1 | 12/2013 | Kashani et al. |
| 2014/0045915 A1 | 2/2014 | Skog et al. |
| 2014/0065147 A1 | 3/2014 | Kastelein et al. |
| 2014/0154684 A1 | 6/2014 | Chang |
| 2014/0206574 A1 | 7/2014 | Chapman et al. |
| 2014/0206957 A1 | 7/2014 | Tseng et al. |
| 2014/0272998 A1* | 9/2014 | Ralfkiaer et al. ....... C12Q 1/68 |
| 2014/0323331 A1 | 10/2014 | Chang et al. |
| 2015/0005184 A1 | 1/2015 | Alsobrook et al. |
| 2015/0133328 A1 | 5/2015 | Ikuta et al. |
| 2015/0259739 A1 | 9/2015 | Chang et al. |
| 2015/0361500 A1 | 12/2015 | Ang et al. |
| 2015/0361509 A1 | 12/2015 | Chang |
| 2015/0376717 A1 | 12/2015 | Thomas et al. |
| 2016/0000936 A1 | 1/2016 | Cuff et al. |
| 2016/0024595 A1 | 1/2016 | Alsobrook, II |
| 2016/0051493 A1 | 2/2016 | Lumpkin et al. |
| 2017/0115291 A1 | 4/2017 | Wong et al. |
| 2017/0176455 A1 | 6/2017 | Leung et al. |
| 2017/0329929 A1 | 11/2017 | Fishman |
| 2018/0110500 A1 | 4/2018 | Palmer et al. |
| 2018/0128714 A1 | 5/2018 | Adey et al. |

(56) References Cited

U.S. PATENT DOCUMENTS

| | | |
|---|---|---|
| 2018/0296591 A1 | 10/2018 | Yu et al. |
| 2019/0367994 A1 | 12/2019 | Chang |
| 2019/0369119 A1 | 12/2019 | Zhuang et al. |
| 2020/0149115 A1 | 5/2020 | Dobak et al. |
| 2020/0289099 A1 | 9/2020 | Palmer et al. |
| 2020/0308649 A1 | 10/2020 | Dobak et al. |
| 2020/0319205 A1 | 10/2020 | Dobak et al. |
| 2020/0383665 A1 | 12/2020 | Palmer et al. |
| 2020/0407800 A1 | 12/2020 | Dobak et al. |
| 2021/0198749 A1 | 7/2021 | Chang |
| 2021/0222246 A1 | 7/2021 | Dobak et al. |
| 2021/0222247 A1 | 7/2021 | Dobak et al. |
| 2021/0222258 A1 | 7/2021 | Chang |
| 2021/0246514 A1 | 8/2021 | Chang |
| 2021/0324480 A1 | 10/2021 | Dobak et al. |
| 2021/0330245 A1 | 10/2021 | Dobak, III et al. |
| 2021/0332442 A1 | 10/2021 | Dobak, III et al. |
| 2021/0345995 A1 | 11/2021 | Dobak, III et al. |

FOREIGN PATENT DOCUMENTS

| | | |
|---|---|---|
| EP | 2151505 A1 | 2/2010 |
| JP | H0852142 A | 2/1996 |
| JP | 2006000385 A | 1/2006 |
| JP | 2007050126 A | 3/2007 |
| JP | 2007259851 A | 10/2007 |
| JP | 2007531529 A | 11/2007 |
| JP | 2010014689 A | 1/2010 |
| WO | WO-0010579 A1 | 3/2000 |
| WO | WO-02053773 A2 | 7/2002 |
| WO | WO-03001985 A2 | 1/2003 |
| WO | WO-03064701 A2 | 8/2003 |
| WO | WO-2005012578 A1 | 2/2005 |
| WO | WO-2005091777 A2 | 10/2005 |
| WO | WO-2005100603 A2 | 10/2005 |
| WO | WO-2006002433 A2 | 1/2006 |
| WO | WO-2006039399 A2 | 4/2006 |
| WO | WO-2006056480 A2 | 6/2006 |
| WO | WO-2007023808 A1 | 3/2007 |
| WO | WO-2007124072 A2 | 11/2007 |
| WO | WO-2008137772 A1 | 11/2008 |
| WO | WO-2009021141 A1 | 2/2009 |
| WO | WO-2009048282 A2 | 4/2009 |
| WO | WO-2009049916 A2 | 4/2009 |
| WO | WO-2009140550 A2 | 11/2009 |
| WO | WO-2010025341 A2 | 3/2010 |
| WO | WO-2010097773 A1 | 9/2010 |
| WO | WO-2011039734 A2 | 4/2011 |
| WO | WO-2011067549 A1 | 6/2011 |
| WO | WO-2011109224 A1 | 9/2011 |
| WO | WO-2012013931 A1 | 2/2012 |
| WO | WO-2012115885 A1 | 8/2012 |
| WO | WO-2012125411 A1 | 9/2012 |
| WO | WO-2012174282 A2 | 12/2012 |
| WO | WO-2013022995 A2 | 2/2013 |
| WO | WO-2013033609 A2 | 3/2013 |
| WO | WO-2013041724 A1 | 3/2013 |
| WO | WO-2013056042 A1 | 4/2013 |
| WO | WO-2013057241 A1 | 4/2013 |
| WO | WO-2013098797 A2 | 7/2013 |
| WO | WO-2013184905 A1 | 12/2013 |
| WO | WO-2014028461 A2 | 2/2014 |
| WO | WO-2014028884 A2 | 2/2014 |
| WO | WO-2014127359 A1 | 8/2014 |
| WO | WO-2014176446 A1 | 10/2014 |
| WO | WO-2014208645 A1 | 12/2014 |
| WO | WO-2014210467 A1 | 12/2014 |
| WO | WO-2015093998 A1 | 6/2015 |
| WO | WO-2016014705 A1 | 1/2016 |
| WO | WO-2016030287 A1 | 3/2016 |
| WO | WO-2016179043 A1 | 11/2016 |
| WO | WO-2017083576 A1 | 5/2017 |
| WO | WO-2017165199 A1 | 9/2017 |
| WO | WO-2018065384 A1 | 4/2018 |
| WO | WO-2018109078 A1 | 6/2018 |
| WO | WO-2018191268 A1 | 10/2018 |
| WO | WO-2019005764 A1 | 1/2019 |
| WO | WO-2019161126 A1 | 8/2019 |
| WO | WO-2019183620 A1 | 9/2019 |
| WO | WO-2019217478 A1 | 11/2019 |
| WO | WO-2020008192 A2 | 1/2020 |
| WO | WO-2020035707 A1 | 2/2020 |
| WO | WO-2020198229 A1 | 10/2020 |
| WO | WO-2020206085 A1 | 10/2020 |
| WO | WO-2021216721 A1 | 10/2021 |
| WO | WO-2021226482 A1 | 11/2021 |
| WO | WO-2022115487 A1 | 6/2022 |
| WO | WO-2022256674 A1 | 12/2022 |

OTHER PUBLICATIONS

Gerami et al. Development and validation of a noninvasive 2-gene molecular assay for cutaneous melanoma (2017) J. Am Acad Dermatol 761, 114-120. (Year: 2017).*

Yao et al. An Adhesive Patch-Based Skin Biopsy Device for Molecular Diagnostics and Skin Microbiome Studies (2017) J Drugs in Derm16:10, 979-986. (Year: 2017).*

Lattimore et al. Investigation of Experimental Factors that Underlie BRCA 1/2 mRNA Isoform Expression Variation: Recommendations for Utilizing Targeted RNA Sequencing to Evaluate Potential Spliceogenic Variants (2018) Front. Onc. 8:140, 9 pages. (Year: 2018).*

Affymetrix NetAffxTM Analysis Center (available via URL: https://www.affynnetrix.conn/analysis/netaffx/showresults.affx. printed on Oct. 21, 2020 (2020).

Al-Shobaili et al. Biochemical markers of oxidative and nitrosative stress in acne vulgaris: correlation with disease activity. J Clin Lab Anal. 2013. 27(1):45-52.

Bernerd et al. Galectin-7 overexpression is associated with the apoptotic process in UVB-induced sunburn keratinocytes. PNAS USA 96(20):11329-11334 (1999).

Chang et al. Liver X Receptor Is a Therapeutic Target for Photoaging and Chronological Skin Aging. Mol Endocrinology 22:2407-2419 (2008).

Chen et al. Type I interferon suppresses memory Th2 cell cytokine secretion from allergic subjects. Allergy 75(3):695-698 (2020).

Deboyes et al., Reduced number of actinic keratoses with topical application of DNA repair enzyme creams. Journal of drugs in dermatology: JDD 9(12):1519-1521 (2010).

Emanuele et al. Anti-inflammatory effects of a topical preparation containing nicotinamide, retinol, and 7-dehydrocholesterol in patients with acne: a gene expression study. Clin Cosmet Investig Dermatol. 2012. 5:33-37.

Graengsjoe et al. Different Pathways in Irritant Contact Eczema? Early Differences in the Epidermal Elemental Content and Expression of Cytokines After Application of 2 Different Irritants. Contact Dermatitis 35(6):355-360 (1996).

Itoh et al. Generation of 3D skin equivalents fully reconstituted from human induced pluripotent stem cells (iPSCs). PLoS One 8(10):e77673 (2013).

Koga et al. Genome-wide screen of promoter methylation identifies novel markers in melanoma. Genome Res. 19:1462-1470 (2009).

Liu et al. Epidermal Genetic Information Retrieval is a non-invasive method of evaluating message (mRNA) profiles of lesional versus non-lesional skin of psoriatic subjects before and after initiations of therapy. J Investigative Dermatology. 122:A54 Abstract 323 (2004).

Liu et al. Inhibition of p38 MAPK signaling augments skin tumorigenesis via NOX2 driven ROS generation. PLoS One 9(5):e97245 (2014).

Merola et al. Non-invasive tape sampling reveals a type I interferon RNA signature in cutaneous lupus erythematosus that distinguishes affected from unaffected and healthy volunteer skin. J Investigative Dermatology 138(5): Abstract 1096 (2018).

Neagu et al. miRNAs in the Diagnosis and Prognosis of Skin Cancer. Front Cell Dev Biol 8:71 (2020).

PCT/US2009/055327 International Preliminary Report on Patentability dated Mar. 10, 2011.

PCT/US2009/055327 International Search Report dated Jan. 7, 2010.

(56) References Cited

OTHER PUBLICATIONS

PCT/US2014/035336 International Preliminary Report on Patentability dated Nov. 5, 2015.
PCT/US2014/035336 International Search Report and Written Opinion dated Sep. 2, 2014.
PCT/US2020/026339 International Search Report and Written Opinion dated Jun. 16, 2020.
PCT/US2020/24469 International Search Report and Written Opinion dated Jun. 19, 2020.
Ressler et al. p16INK4A is a robust in vivo biomarker of cellular aging in human skin. Aging Cell 5(5):379-389 (2006).
Sander et al. Expression of extracellular matrix protein 1 (ECM1) in human skin is decreased by age and increased upon ultraviolet exposure. Br J Dermatol 154(2):218-224 (2006).
Schauberger et al. Development of a non-invasive method of RNA collection in children with atopic dermatitis. J Allergy Clin Immunol. 139(2):AB239, No. 751 (2017).
Stevens et al. Disease-associated KIF3A variants alter gene methylation and expression impacting skin barrier and atopic dermatitis risk. Nature Communications 11:4092 (2020).
Stoddard et al., Improvement of actinic keratoses using topical DNA repair enzymes: a randomized placebo-controlled trial. Journal of Drugs in Dermatology: JDD 16(10):1030-1034 (2017).
Torres et al. MicroRNA Ratios Distinguish Melanomas from Nevi. J Invest Dermatol . 140(1):164-173.e7 (2020).
U.S. Appl. No. 12/550,060 Office Action dated Nov. 18, 2014.
U.S. Appl. No. 14/715,424 Office Action dated Oct. 24, 2016.
U.S. Appl. No. 14/832,964 Office Action dated Aug. 9, 2017.
U.S. Appl. No. 14/832,964 Office Action dated Dec. 12, 2016.
U.S. Appl. No. 16/874,473 Office Action dated Oct. 26, 2020.
U.S. Appl. No. 12/550,060 Office Action dated Apr. 2, 2014.
Wang et al. Why minimally invasive skin sampling techniques? A bright scientific future. Cutan Ocul Toxicol 30(1):1-6 (2011).
Yaar et al. Fifty years of skin ageing. JID symposium Proceedings 7(1):51-58 (2002).
Yao et al. An Adhesive Patch-Based Skin Biopsy Device for Non-Invasive Gene Expression Analysis in Dermatology. DermTech, Mar. 2017, available via URL: dernntech.conn/wp-content/uploads/2017/03/Skin-Biopsy-Device-1.pdf (2017).
Cerda et al. Geometry and Physics of Wrinkling. Phys Rev Lett 90(7):074302 (2003).
Co-pending U.S. Appl. No. 17/183,589, inventors Palmer; Tara J. et al., filed Feb. 24, 2021.
Co-pending U.S. Appl. No. 29/770,783, inventors Dobak; John et al., filed Feb. 16, 2021.
Co-pending U.S. Appl. No. 29/770,784, inventors Dobak; John et al., filed Feb. 16, 2021.
Co-pending U.S. Appl. No. 29/770,785, inventors Dobak; John et al., filed Feb. 16, 2021.
Co-pending U.S. Appl. No. 29/770,786, inventors Dobak; John et al., filed Feb. 16, 2021.
Dalbe et al. Multiscale Stick-Slip Dynamics of Adhesive Tape Peeling. Phys Rev Lett 115(12):128301 (2015).
De Zotti et al. Bending to Kinetic Energy Transfer in Adhesive Peel Front Microinstability. Phys Rev Lett 122(6):068005 (2019).
Thoroddsen et al. Stick-slip substructure in rapid tape peeling. Phys Rev Lett 82(4 Pt 2):046107 (2010).
U.S. Appl. No. 16/522,291 Office Action dated Apr. 28, 2021.
U.S. Appl. No. 16/522,291 Office Action dated Jan. 7, 2021.
U.S. Appl. No. 16/603,435 Restriction Requirement dated May 25, 2021.
U.S. Appl. No. 16/874,473 Office Action dated Feb. 5, 2021.
Capone et al. Systems analysis of human T helper17 cell differentiation uncovers distinct time-regulated transcriptional modules. iScience. 24:102492 (2021).
Co-pending U.S. Appl. No. 29/796,477, inventor Dobak; John, filed Jun. 24, 2021.
Dobbeling et al. Method for simultaneous RNA and DNA isolation from biopsy material, culture cells, plants and bacteria. Biotechniques 22:88-90 (1997).
Dyjack et al. Minimally invasive skin tape strip RNA sequencing identifies novel characteristics of the type 2-high atopic dermatitis disease endotype. J Allergy Clin Immunol. 141(4):1298-1309 (2018).
Emtage et al. IGFL: A secreted family with conserved cysteine residues and similarities to the IGF superfamily. Genomics 88(4):513-520 (2006).
Enderle et al. Monitoring therapy response and resistance mutations in circulating RNA and DNA of plasma from melanoma patients. Obtained from http://cpnr-cw7w.accessdomain.com/sites/default/files/2014_11_14_longitudinal_poster_final3_website.pdf on Aug. 23, 2021 (2014).
Hennig et al. Automated extraction of DNA and RNA from a single formalin-fixed paraffin-embedded tissue section for analysis of both single-nucleotide polymorphisms and mRNA expression. Clinical Chemistry 56:1845-1853 (2010).
Homey et al. Cutting edge: the orphan chemokine receptor G protein-coupled receptor-2 (GPR-2, CCR10) binds the skin-associated chemokine CCL27 (CTACK/ALP/ILC). J. Immunol. 164:3465-3470 (2000).
Kim et al J Allergy Clin Immunol. Feb. 2015 vol. 135, Issue 2, Supplement AB261 (2015).
Krueger et al. Non-invasive gene expression analysis for psoriasis. Available via URL: dermtech.com/wp-content/uploads/2017/03/Psoriasis.pdf (2017).
Lund et al. Genome-wide identification of novel genes involved in early Th1 and Th2 cell differentiation. J Immunology 178:3648-3660 (2007).
Nindl et al. Identification of differentially expressed genes in cutaneous squamous cell carcinoma by microarray expression profiling. Mol Cancer 5(1):30 (2006).
Pacifico et al. Loss of CDKN2A and pl4ARF expression occurs frequently in human nonmelanoma skin cancers: Inactivation of CDKN2A in human NMSC. Br J Dermatol 158(2):291-297 (2007).
Pan et al. Expression profiles of Th17 pathway related genes in human systemic lupus erythematosus. Mol Biol Rep. 40:391-399 (2013).
PCT/US2021/028415 International Search Report and Written Opinion dated Aug. 6, 2021.
PCT/US2021/031330 International Search Report and Written Opinion dated Aug. 31, 2021.
Pedicini et al. Combining network modeling and gene expression microarray analysis to explore the dynamics of Th1 and Th2 cell regulation. PLoS Comput Biol. 6(12):e1001032 (2010).
Rivlin et al. Mutations in the p53 Tumor Suppressor Gene: Important Milestones at the Various Steps of Tumorigenesis. Genes Cancer 2(4):466-474 (2011).
Seibold et al. J Allergy Clin Immunol. vol. 139. Issue 2, Supplement, Abstract 856, p. AB273 (2017).
Sonokoly et al. IL-31: A new link between T cells and pruritus in atopic skin inflammation. J Allergy Clin Immunol. 117:411-417 (2006).
Thijs et al. Moving toward endotypes in atopic dermatitis: Identification of patient clusters based on serum biomarker analysis. J Allergy Clin Immunol. 140:730-737 (2017).
U.S. Appl. No. 16/522,291 Office Action dated Dec. 7, 2021.
U.S. Appl. No. 16/522,291 Office Action dated Sep. 16, 2021.
U.S. Appl. No. 16/603,435 Office Action dated Sep. 10, 2021.
U.S. Appl. No. 16/874,473 Office Action dated Aug. 6, 2021.
U.S. Appl. No. 17/214,675 Office Action dated Jul. 27, 2021.
U.S. Appl. No. 17/214,675 Office Action dated Nov. 29, 2021.
U.S. Appl. No. 17/214,695 Office Action dated Jul. 27, 2021.
U.S. Appl. No. 17/214,695 Office Action dated Nov. 29, 2021.
Wang et al. Frequency and features of TP53 mutation in 30 Chinese patients with sporadic basal cell carcinoma. Clin Exp Dermatol 39(7):829-834 (2014).
Wang et al. Simultaneous Extraction of DNA and RNA from Hepatocellular Carcinoma (Hep G2) Based on Silica-Coated Magnetic Nanoparticles. J. Nanosci. Nanotechnol. 17:802-806 (2017).
Acevedo et al. Analysis of the mechanisms mediating tumor-specific changes in gene expression in human liver tumors. Cancer Res. 68:2641-2651 (2008).
Ackerman et al. Charcot-Leyden crystal protein (galectin-10) is not a dual function galectin with lysophospholipase activity but binds a

(56) References Cited

OTHER PUBLICATIONS lysophospholipase inhibitor in a novel structural fashion. J Biol Chem 277(17):14859-148-68 (2002).
Affymetrix GeneChip Human Genome U133 Array Set HG-U133A, Geo Expression, Mar. 11, 2002 (XP002361324).
Affymetrix HG U133 Gene Chip (www.affymetrix.com U133 gene chip) accessed Oct. 13, 2015.
Aitman. DNA microarrays in medical practice. BMJ. 323(7313):611-615 (2001).
Albert et al. Years of potential life lost: another indicator of the impact of cutaneous malignant melanoma on society. J Am Acad Dermato 23(2 Pt 1):308-310 (1990).
Alberts et al. The immune system. Molecular Biology of The Cell. New York, NY, Garland Publishing, Inc. pp. 1229-1235 (1994).
Allison et al. A mixture model approach for the analysis of microarray gene expression data. Computational Statistics and Data Analysis 39:1-20 (2002).
Applied Biosystems, User Bulletin #2: Relative quantitation of gene expression. http://docs.appliedbiosystems.com/pebiodocs/04303859.pdf (2001).
Armstrong et al., The epidemiology of UV induced skin cancer. Journal of Photochemistry and Photobiology B: Biology 63(1-3):8-18 (2001).
Asada et al. Cytokine Gene Expression during the Elicitation Phase of Contact Sensitivity: Regulation by Endogenous IL-4. Journal of Investigative Dermatology 108(4):406-411 (1997).
Asadullah et al. Cytokines: interleukin and interferon therapy in dermatology. Clinical & Experimental Dermatology 27:578-584 (2002).
Baehrecke. miRNAs: micro managers of programmed cell death. Curr Biol 13(12):R473-R475 (2003).
Baggerly et al. Deriving Chemosensitivity From Cell Lines: Forensic Bioinformatics And Reproducible Research In High-Throughput Biology. The Annals of Applied Sciences 3:1309-1334 (2009).
Baker et al. Normal keratinocytes express Toll-like receptors (TLRs) 1, 2 and 5: modulation of TLR expression in chronic plaque psoriasis. Br J Dermatol 148(4):670-679 (2003).
Baldi et al. A Bayesian framework for the analysis of microarray expression data: regularized t-test and statistical inferences of gene changes. Bioinformatics 17(6):509-519 (2001).
Baldi et al. cDNA array technology in melanoma: an overview. J. Cell. Physiol. 196(2):219-223 (2003).
Balic et al. High quality assessment of DNA methylation in archival tissues from colorectal cancer patients using quantitative high-resolution melting analysis. J. Mol. Diagn. 11:102-108 (2009).
Ball et al. Targeted and genome-scale methylomics reveals gene body signatures in human cell lines. Nat. Biotechnol 27:361-368 (2009).
Bartel. MicroRNAs: genomics, biogenesis, mechanism, and function. Cell 116(2): 281-297 (2004).
Bashir et al. Physical and physiological effects of stratum corneum tape stripping. Skin Res Technol 7(1):40-48 (2001).
Bataille. Genetics of familial and sporadic melanoma. Clin. Exp. Dermatol. 25(6):464-467 (2000).
Bayon et al. Mechanisms of cell signaling in immune-mediated inflammation. Cytokines Cell Mol Ther 4(4):275-286 (1998).
Becker et al. Detection of differentially regulated genes in keratinocytes by cDNA array hybridization: Hsp27 and other novel players in response to artificial ultraviolet radiation.J. Invest. Dermatol. 116:983-988 (2001).
Becker et al. Mouse models for melanoma: a personal perspective. Experimental Dermatology 19:157-164 (2010).
Benavides et al. Impaired hair follicle morphogenesis and cycling with abnormal epidermal differentiation in nackt mice, a cathepsin L-deficient mutation. Am J Pathol 161(2):693-703 (2002).
Benner, et al. Evolution, language and analogy in functional genomics. Trends in Genetics, 17:414-418 (2001).
Benson et al. A comparison of keratin gene expression between inflamed and control skin obtained by tape harvest. Journal of Investigative Dermatology 122(3):A48 (2004).
Benson et al. An analysis of select pathogenic messages in lesional and non-lesional psoriatic skin using non-invasive tape harvesting. Journal of Investigative Dermatology 126:2234-2241 (2006).
Benson et al. GenBank. Nucleic Acids. Res. 30(1):17-20 (2002).
Berardesca et al., Reduced ultraviolet-induced DNA damage and apoptosis in human skin with topical application of a photolyase-containing DNA repair enzyme cream: clues to skin cancer prevention. Molecular Medicine Reports 5(2):570-574 (2012).
Berger et al. A reappraisal of the 21-day cumulative irritancy test in man. J. Toxicol-Cut and Ocular Toxicol 1(2):101-107 (1982).
Bertucci et al. Gene expression profiling of cancer by use of DNA arrays: how far from the clinic. Lancet Oncol 2(11):674-682 (2001).
Bibkova et al. High-throughput DNA methylation profiling using universal bead arrays. Genome Res. 16:383-393 (2006).
Bittner et al. Molecular classification of cutaneous malignant melanoma by gene expression profiling. Nature 406:536-540 (2000).
Boelsma et al. Expression of skin-derived antileukoproteinase (SKALP) in reconstructed human epidermis and its value as a marker for skin irritation. Acta Derm Venereol 78(2):107-113 (1998).
Booken et al. Sézary syndrome is a unique cutaneous T-cell lymphoma as identified by an expanded gene signature including diagnostic marker molecules CDO1 and DNM3. Leukemia 22(2):393-9 (2008).
Borevitz et al. Large-scale identification of single-feature polymorphisms in complex genomes. Genome Res 13(3):513-523 (2003).
Boxman et al. Proteomic analysis of skin irritation reveals the induction of HSP27 by sodium lauryl sulphate in human skin. Br J Dermatol 146(5):777-785 (2002).
Brand et al. IL-1B Protein in Human Skin Lymph Does Not Discriminate Allergic from Irritant Contact Dermatitis. Contact Dermatitis,35:152-156 Munksgaard, Denmark (1996).
Brand et al. Untersuchung menschlicher Hautlymphe: Unterscheiden sich irritative und allergische Kontaktdermatitiden benglich ihres Zytokinmusters? Zeitschrift for Hautkrankheiten, 72:435-440 (1997). (English Abstract).
Brehmer-Andersson et al. Tape-Stripping Method for Cytological Diagnosis of Mycosis Fungoides. Acta Derm-Venereol 47:177-180 (1967).
Brennecke et al. Bantam encodes a developmentally regulate microRNA that control cell proliferation and regulates the proapoptotic gene hid in *Drosophila*. Cell 113(1):25-36 (2003).
Breslow. Thickness, cross-sectional areas and depth of invasion in the prognosis of cutaneous melanoma. Ann. Surg. 172:902-908 (1970).
Bunge et al. Improvement of Methodology for Assessing Bioequivalence of Topical Products http://www.fda.gov/ohrms/dockets/ac/03/slides3996s2 07 bunge.pdf Oct. 22, 2003.
Bustin. Quantification of mRNA using real-time reverse transcription PCR (RT-PCR): trends and problems. J Mol Endocrinol 29(1):23-39 (2002).
Cachia et al. CDKN2A mutation and deletion status in thin and thick primary melanoma. Clin. Cancer Res. 6(9):3511-3515 (2000).
Cai et al. Kaposi's sarcoma-associated herpesvirus expresses an array of viral microRNAs in latently infected cells. PNAS USA 102(15):5570-5575 (2005).
Calin et al. A MicroRNA signature associated with prognosis and progression in chronic lymphocytic leukemia. N Engl J Med. 353(17):1793-1801 (2005).
Callen et al. AAD Consensus statement on psoriasis therapies. J Amer Acad Dermatol 49:897-899 (2003).
Candiloro et al. Assessing combined methylation-sensitive high resolution melting and pyrosequencing for the analysis of heterogeneous DNA methylation. Epigenetics 6(4):500-507 (2011).
Carr et al. Gene-expression profiling in human cutaneous melanoma. Oncogene 22(20):3076-3080 (2003).
Chakraboty et al. Differential gene expression in genetically matched mouse melanoma cells with different metastatic potential. Gene 315L165 (2003).
Chang et al. A non-invasive genomic assay for the detection of melanoma in suspicious pigmented nevi. Cancer Research Abstract LB-221 (4 pgs.) (2008).
Chen et al. MicroRNAs modulate hematopoietic lineage differentiation. Science 303(5654):83-86 (2004).

(56) References Cited

OTHER PUBLICATIONS

Cheung et al. Natural variation in human gene expression assessed in lymphoblastoid cells. Nat Genet 33:422-425 (2003).
Childs. Noninvasive gene expression testing in amelanotic melanoma. JAMA Dermatol 154(2):223-224 (2018).
Choi et al. Genomic landscape of cutaneous T cell lymphoma. Nat Genet. 47(9):1011-9 (2015).
Chuaqui et al. Post-analysis follow-up and validation of microarray experiments. Nature Genetics 32(Supp):509-514 (2002).
Chung et al. Factors that control extravascular fibrinolysis. Semin Thromb Hemost 22(6):479-488 (1996).
Chung et al. Sodium dodecyl sulfate induces plasminogen activator inhibitor type 2 expression in epidermal keratinocytes in vivo and in vitro. J Invest Dermatol 117(3):647-653 (2001).
Ciafre et al. Extensive modulation of a set of MicroRNAs in primary glioblastoma. Biochem Biophys Res Commun. 334(4):1351-1358 (2005).
Clauser et al. Rapid mass spectrometromic peptide sequencing and mass matching for characterization of human melanoma proteins isolated by two-dimensional page. PNAS 92:5072-5076(1995).
Colonna. TREMs in the immune system and beyond. Nat Rev Immunol 3(6):445-553 (2003).
Conner et al. Detection of sickle cell Beta S-golbin allele by hybridization with synthetic oligonucleotides. PNAS USA 80:278-282 (1983).
Coquette et al. Analysis of interleukin-lalpha (IL-lalpha) and interleukin-8 (IL-8) expression and release in in vitro reconstructed human epidermis for the prediction of in vivo skin irritation and/or sensitization. Toxicol In Vitro 17(3):311-321 (2003).
Cosini et al. Cytokines and Irritant Contact Dermatitis. Toxicology Letters 102:103:277-282 (1998).
Costello et al. Restriction landmark genome scanning. Meth. Mol Biol 200:53-70 (2002).
Cottrell et al. A real-time PCR assay for DNA-methylation using methylation-specific blockers. Nucleic Acids Res. 32:e10 (2004).
Cottrell et al. Discovery and validation of 3 novel DNA methylation markers of prostate cancer prognosis. J. Urology 177:1753-1758 (2007).
Couzin-Frankel. As Questions Grow, Duke Halts Trials, Launches Investigation. Science Magazine pp. 614-615 (Aug. 2010).
Cullander et al. A quantitative minimally invasive assay for the detection of metals in the stratum corneum, J Pharm Biomed Anal. 22(2):265-279 (2000).
Cumberbatch et al. Differential regulation of epidermal langerhans cell migration by interleukins (IL)-lalpha and IL-lbeta during irritant- and allergen-induced cutaneous immune responses. Toxicol Appl Pharmacol 182(2):126-135 (2002).
Cummins et al. The colorectal microRNAome. PNAS USA 103(10):3687-3692 (2006).
Curtin et al. Distinct sets of genetic alterations in melanoma. The New England Journal of Medicine 353(20):2135-2147 (2005).
Davies et al. Mutations of the BRAF Gene in Human Cancer. Nature 417:949-954 (2002).
Davy et al. Ephrin-A5 modulates cell adhesion and morphology in an integrin-dependent manner. EMBO J 19(20):5396-5403 (2000).
Deeds et al. Patterns of melastatin mRNA expression in melanocytic tumors. Human Pathology 31(11):1346-1356 (2000).
Degraves et al. High-Sensitivity Quantitative PCR Platform. Biotechniques 34(1):106-115 (2003).
Deiman et al. Characteristics and applications of nucleic acid sequence-based amplification (NASBA). Mol. Biotechnol. 20(2):163-179 (2002).
Dekker et al. Characterization of interleukin-1 alpha-induced melanoma cell motility: inhibition by type I and type II receptor-blocking monoclonal antibodies. Melanoma Res. 7(3):223-230 (1997).
Dembinska-Kiec et al. Proangiogenic activity of beta-carotene is coupled with the activation of endothelial cell chemotaxis. Biochimica et Biophysica Acta 1740:222-239 (2005).
Deng et al. Targeted bisulfite sequencing reveals changes in DNA methylation associated with nuclear reprogramming. Nat. Biotechnol 27:353-360 (2009).
Dong et al. Chemokines and diseases. European Journal of Dermatology 13:224-230 (2003).
Draft Guidance for Industry on Topical Dermatological Drug Product NDA's and ANDA's—In Vivo Bioavailability, Bioequivalence, in Vitro Release and Associated Studies: Dermatopharmacokinetics (DPK) Method Issues, http://srpub.pharma.org/letters/08.17.98.topical.derm.html. PRMA 1998.
Dreher et al. Colorimetric Method For Quantifying Human Stratum Corneum Removed by Adhesive Tape Stripping. Acta Derma Venereol (Stockholm) 78:186-189 (1998).
D-SQUAME from Cu-DEM (2003).
Dulmage et al. Lessons learned from gene expression profiling of cutaneous T-cell lymphoma. Br J Dermatol 169(6):1188-97 (2013).
Duncan et al. Melastatin expression and prognosis in cutaneous malignant melanoma. Journal of Clinical Oncology 19(2):568-576 (2001).
Eads et al. MethyLight: a high-throughput assay to measure DNA methylation. Nucleic Acid Res. 28:e32 (2000).
Easty et al. Up-regulation of ephrin-A1 during melanoma progression. Int. J. Cancer 84:494-501 (1999).
Edelman et al. Analysis of sample set enrichment scores: assaying the enrichment of sets of genes for individual samples in genome-wide expression profiles. Bioinformatics 22(14):e108-116 (2006).
Efron et al. Empirical hayes methods and false discovery rates for microarrays. Genet Epidemiol 23(1):70-86 (2002).
Elder. Precursors to melanoma and their mimics: nevi of special sites. Modern Pathology 19:s4-s20 (2006).
Elwood et al., Melanoma and sun exposure: an overview of published studies. International Journal of Cancer 73(2):198-203 (1997).
Enard et al. Intra- and Interspecific Variation in Primate Gene Expression Patterns. Science 296:340-343 (2002).
Esquela-Kerscher et al., Oncomirs—microRNAs with a role in cancer. Nat Rev Cancer 6(4):259-69 (2006).
Fackler et al. Quantitative multiplex methylation-specific PCR analysis doubles detection of tumor cells in breast ductal fluid. Clin. Cancer Res. 12(11 Pt 1):3306-3310 (2006).
Fackler et al. Quantitative multiplex methylation-specific PCR assay for the detection of promoter hypermethylation in multiple genes in breast cancer. Cancer Res. 64(13):4442-4452 (2004).
Farage et al. Further Development of Noninvasive Method for Assessing Human Skin Irritation, Abstract # 1909, The Proctor & Gamble Company, (1998).
Feghali et al. Cytokines in acute and chronic inflammation. Front Biosci 2:d12-26 (1997).
Ferris et al. Impact on clinical practice of a non-invasive gene expression melanoma rule-out test: 12-month follow-up of negative test results and utility data from a large US registry study. Dermatology Online J 25(5):pii (May 2019).
Ferris et al. Noninvasive analysis of high-risk driver mutations and gene expression profiles in primary cutaneous melanoma. J Invest Dermatol 139:1127-1134 (2019).
Ferris et al. Real-world performance and utility of a noninvasive gene expression assay to evaluate melanoma risk in pigmented lesions. Melanoma Res 28(5):478-482 (2018).
Ferris et al. Utility of a noninvasive 2-gene molecular assay for cutaneous melanoma and effect on the decision to biopsy. JAMA Dermatol 153(7):675-680 (2017).
Flier et al. The CXCR3 activating chemokines IP-10, Mig, and IP-9 are expressed in allergic but not in irritant patch test reactions. J Invest Dermatol 113(4):5740-5748 (1999).
Fray et al. A potent, selective inhibitor of matrix metalloproteinase-3 for the topical treatment of chronic dermal ulcers. J Med Chem 46(16):3514-3525 (2003).
Freedberg et al. Keratins and the Keratinocyte Activation Cycle. The Journal of Investigative Dermatology 116(5):633-640 (2001).
Frommer et al. A genomic sequencing protocol that yields a positive display of 5-methylcytosine residues in individual DNA strands. PNAS USA 89:1827-1831 (1992).
Galiegue et al. Exploitation of expression profiles: examples in oncology. J Soc Biol 196(4):313-315 (2002).

(56) References Cited

OTHER PUBLICATIONS

Garcia-Sancha et al. MicroRNA Dysregulation in Cutaneous Squamous Cell Carcinoma (Review). Int. J. Mol. Sci. 20:2181 (2019).

Garofano et al. Comparison of Powerplex® 16 System and Other Multiplex STR Typing Kits on Casework, (Reporto Carabinieri Investigazioni Scientifiche, Parma, Italia.), 2000. Reference available at: http://www. promeea.com/eeneticidproc/ussvmp11proc/default.htm.

Garofano et al. PCR based analysis of epidermal cells found on adhesive tape, Advances in Forensic Haemogenetic, 6:281-283. (Istituto di Anatomia e Fisiologia Umana, Universita degli Studi ti Torino, Italy) (1996).

Garrett et al Tired of the same old grind in the new genomics and proteomics era? Targets Innovations in Genomics & Proteomics 1(5):156-162 (2002).

Gebhard et al. Genome-wide profiling of CpG methylation identifies novel targets of aberrant hypermethylation in myeloid leukemia. Cancer Res. 66:6118-6128 (2006).

Gebhard et al. Rapid and sensitive detection of CpG-methylation using methyl-binding (MB)-PCR. Nucleic Acids Res. 34:e82 (2006).

Genecard (www.genecards.org)—Accessed Nov. 11, 2009.

Gerami et al. Development and validation of a noninvasive 2-gene molecular assay for cutaneous melanoma. J Am Acad Dermatol 76(1):114-120.e2 (2017).

Gerami et al. Development of a novel noninvasive adhesive patch test for the evaluation of pigmented lesions of the skin. J Am Acad Dermatol 71(2):237-244 (2014).

Germai et al. Development and Validation of a Noninvasive 2-gene Molecular Assay for Cutaneous Melanoma. J Am Acad Dermatol 76(1):114-120 (2016).

Gerritsen et al. Repeated tape stripping of normal skin: a histological assessment and comparison with events seen in psoriasis. Arch Dermatol Res., 286(8):455-461 (1994).

Gershenwald et al. Gene expression profiling of human cutaneous melanoma: are we there yet? Cancer Biol Ther 3(1):121-123 (2004).

Ghali et al. Epidermal and Hair Follicle Progenitor Cells express Melanoma-Associated Chondroitin Sulfate Proteoglycan Core Protein. Journal of Investigative Dermatology 122:433-442 (2004).

Gibson et al. A Novel Method for Real Time Quantitative RT-PCR. Genome Research 6:995-1001 (1996).

Gloster et al. The epidemiology of skin cancer. Dermatol Surg. 22(3):217-226 (1996).

Goldschmidt et al. Desquamation of the Human Horny Layer. Archives of Dermatology 95:583-586 (1967).

Gong et al. MiRNA-221 promotes cutaneous squamous cell carcinoma progression by targeting PTEN. Cell Mol Biol Lett. 24:9 (2019).

Gonzalgo et al. Rapid quantitation of methylation differences at specific sites using methylation-sensitive single nucleotide primer extension (Ms-SNuPE). Nucleic Acids Res. 25:2529-2531 (1997).

Graham. Basic Pathologic Changes in Skin, in Dermal Pathology, Wd. J H Graham, W C Johnson, and E B Helwig, Harper-Row, Hagerstown, MD, pp. 119-135 (1972).

Grammatico et al. Involvement of the 4q21 region in human malignant melanomas: cytogenetic and immunocytochemical characterization of three primary cell cultures. World. J. of Surgery 19:350-351 (1995).

Grangsjo et al. Different Pathways in Irritant Contact Eczema? Early Differences in the Epidermal Elemental Content and Expression of Cytokines after Application of 2 Different Irritants. Contact Dermatitis 35:355-360 Munksgaard, Denmark (1996).

Granstein. New Treatments for Psoriasis. The New England Journal of Medicine 345(4):284-287 (2001).

GRO1. Cancer Genetics Web. (www.cancer-genetics.org) 2 pages (2003).

Gyorffy et al. A web-based data warehouse on gene expression in human malignant melanoma. Journal of Investigative Dermatology 127:394-399 (2007).

Hamid et al. In Vivo Expression of IL-12 and IL-13 in Atopic Dermatitis. Journal of Allergy and Clinical Immunology 98(l):1-8 (1996).

Hammond MicroRNAs as oncogenes. Curr Opin Genet Dev 16(1):4-9 (2006).

Haqq et al. The gene expression signatures of melanoma progression. PNAS USA 102(17):6092-6097 (2005).

Harris et al. Single-molecule DNA sequencing of a viral genome. Science 320:106-109 (2008).

Haskill et al. Identification of three related human GRO genes encoding cytokine functions. PNAS 87:7732-7736 (1990).

Hatfield et al. Differential analysis of DNA microarray gene expression data. Mol. Microbiol. 47(4):871-877 (2003).

Heaton et al. Surgical margins and prognostic factors in patients with thick (> 4mm) primary melanoma. Ann Surg Oncol 5:322-328 (1998).

Heid et al. Real Time Quantitative PCR. Genome Research 6:986-994 (1996).

Herman et al. Gene silencing in cancer in association with promoter hypermethylation. N Engl J Med 349(21):2042-2054 (2003).

Herman et al. Methylation-specific PCR: a novel PCR assay for methylation status of CpG islands. PNAS USA 93:9821-9826 (1996).

Herouy. Matrix metalloproteinases in skin pathology (Review). Int J Mol Med 7(1):3-12 (2001).

Hirao et al. Elevation of Interleukin 1 Receptor Antagonist in the Stratum Corneum of Sun-Exposed and Ultraviolet B-Irradiated Human Skin. The Journal of Investigative Dermatology 106(5):1102-1107 (1996).

Hodson et al. In situ PCR for visualization of microscale distribution of specific genes and gene products in prokaryotic communities. Applied and environmental microbiology 61(11):4074-4082 (1995).

Hoefakker et al. In vivo Cytokine Profiles in Allergic and Irritant Contact Dermatitis. Contact Dermatitis 33:258-266 Munksgaard, Denmark (1995).

Hoffrage et al. Communicating Statistical Information. Science 290(5500):2261-2262 (2000).

Hojyo-Tomoka et al. Does Cellophane Tape Stripping Remove the Horny Layer? Archives of Dermatology 106(5):767-768 (1972).

Holland et al. Detection of specific ploymerase charin reaction product by utilizing the 5'-3' exonuclease activity of Thermus aquaticus DNA polymerase. PNAS USA 88(16):7276-7280 (1991).

Holleran et al. Regulation of epidermal sphingolipid synthesis by permeability barrier function. J. Lipid Research 32:1151-1158 (1991).

Horak et al. ChIP-chip: a genomic approach for identifying transcription factor binding sites. Methods Enzymol 350:469-483 (2002).

Hornberger et al. Clinical and economic implications of a noninvasive molecular pathology assay for early detection of melanoma. JAMA Dermatol 154(9):1-8 (2018).

Howie et al. Epidermal keratinocyte production of interferon-gamma immunoreactive protein and mRNA is an early event in allergic contact dermatitis. Journal of Investigative Dermatology 106(6):1218-1223 (1996).

Hu et al. MicroRNA-186 promotes cell proliferation and inhibits cell apoptosis in cutaneous squamous cell carcinoma by targeting RETREG1. Expt. Therapeutical Medicine 17:1930-1938 (2019).

Huang et al. Highly Recurrent TERT Promoter Mutations in Human Melanoma. Science 339:957-959 (2013).

Hung et al. Global gene expression profiling in *Escherichia coli* K12: The effects of leucine-responsive regulatory protein. J. Biol. Chem. 277(43):40309-40323 (2002).

Ichinose. Physiopathology and regulation of factor XIII. Thromb Haemost 86(1):57-65 (2001).

Instructions for use DermTech adhesive skin biopsy kit. DermTech. Available at http://dermtech.com/wp-content/uploads/2015/10/dermtech-ifu-skin-collection-v7.pdf (Revised data Oct. 2015) (1 pg.).

Iorio et al. MicroRNA gene expression deregulation in human breast cancer. Cancer Res 65(16):7065-7070 (2005).

Itzkowitz et al. Improved fecal DNA test for colorectal cancer screening. Clin Gastroenterol. Hepatol. 5(1):111-117 (2007).

(56) References Cited

OTHER PUBLICATIONS

Jansen et al. Gene expression analysis differentiates melanomas from Spitz nevi. J Drugs Dermatol 17(5):574-576 (2018).
Jemal et al. Cancer statistics. CA Cancer J Clin 2003. 53(1):5-26 (2003).
Jovanovic. Molecular studies of melanoma. Archive of Oncology13:75-77 (2005).
Junghans et al. Epidermal Cytokines IL-IB, TNF-a, and IL-12 in Patients with Atopic Dermatitis: Response to Application of House Dust Mite Antigens. The Journal of Investigative Dermatology 111(6):1184-1188 (1998).
Kahari et al. Matrix metalloproteinases in skin. Exp Dermatol 6(5):199-213 (1997).
Kalia et al. Homogeneous transport in a heterogeneous membrane: water diffusion across human stratum corneum in vivo. Biophys J 71(5):2692-2700 (1996).
Kallioniemi. Biochip technologies in cancer research. Ann Med. Mar; 33(2):142-147 (2001).
Katerinaki et al. TNF-alpha increases human melanoma cell invasion and migration in vitro: the role of proteolytic enzymes. British Journ of Cancer 89:1123-1129 (2003).
Katz et al. Skin surface touch print for diagnosing fungal infections. American Family Physician 31(4):189-194 (1985).
Kawada et al. Processing of cathepsins L, B and D in psoriatic epidermis. Arch Dermatol Res 289(2):87-93 (1997).
Keppler, D. Towards novel anti-cancer strategies based on cystatin function. Cancer Letters 235(2):159-176 (2006).
Kerkhoff et al. The regulatory role of MRP8 (S100A8) and MRP14 (S100A9) in the transendothelial migration of human leukocytes. Pathobiology 67(5-6):230-232 (1999).
Kilpatrick. Animal lectins: a historical introduction and overview. Biochim Biophys Acta 1572(2-3):187-197 (2002).
Kim et al. Epigenomic Profiling Reveals Novel and Frequent Targets of Aberrant DNA Methylation-Mediated Silencing in Malignant Glioma. Cancer Research 66(15):7490-7501 (2006).
Kim et al. The promise of microarray technology in melanoma care. Cancer Contro. 9(1):49-53 (2002).
Klaschka et al. Individual Transparency Patterns of Adhesive-tape Strip Series of the Stratum Corneum. International Journal of Dermatology 16(10):836-841 (1977).
Klaschka et al. New Measuring Device of Horny Layer Transparency. Archives of Dermatology 254:313-325 (1975).
Kohnken et al. MicroRNAs in Cutaneous T-Cell Lymphoma: The Future of Therapy. J Invest Dermatol. 139(3):528-534 (2019).
Komine et al. Interleukin-1 induces transcription of keratin K6 in human epidermal keratinocytes. J Invest Dermatol 116(2):330-338 (2001).
Komine et al. Regulation of epidermal expression of keratin K17 in inflammatory skin diseases. J Invest Dermatol 107(4):569-575 (1996).
Kondo et al. Characterization of Epidermal Cytokine Profiles in Sensitization and elicitaion Phases of Allergic Contact dermatitis as well as Irritant Contact dermatitis in Mouse skin. Lymphokine and Cytokine Res. 13(6):367-375 (1994).
Kong et al. A multivariate approach for integrating genome-wide expression data and biological knowledge. Bioinformatics 22(19):2373-2380 (2006).
Koning et al.T Cell Subsets and Cytokines in Allergic and Non-allergic Children. I. Analysis of IL-4 IFN-gamma and IL-13 mRNA Expression and Protein Production. Cytokine 9(6):416-426 (1997).
Krasteva. Contact dermatitis. Int. Dermatol. 32:547-560 (1993).
Kricker et al., Sun exposure and non-melanocytic skin cancer. Cancer Causes & Control 5(4):367-392 (1994).
Kroese et al. Genetic tests and their evaluation: Can we answer the key questions? Genetics in Medicine 6:475-480 (2004).
Kupper. Production of Cytokines by Epithelial Tissues.Am. J Dermatopathol. 11:69-73 (1993).
Lacroix et al. A low-density DNA microarray for analysis of markers in breast cancer. Int J Biol Markers 17(1):5-23 (2002).
Landegren et al. A ligase-mediated gene detection technique. Science 241:1077-1080 (1988).
Landegren et al. DNA Diagnostics—Molecular Techniques and automation. Science, 242:229-237 (1988).
Lee et al. The C. elegans heterochronic gene lin-4 encodes small RNAs with antisense complementarity to lin-14. Cell 75:843-854 (1993).
Lendeckel et al. Synergistic action of DPIV and APN in the regulation of T cell function. Adv Exp Med Biol 524:123-131 (2003).
Lener et al. Expression profiling of aging in the human skin, Experimental Gerontology, 41:387-397 (2006).
Li et al. Model-based analysis of oligonucleotide arrays: expression index computation and outlier detection. PNAS USA 98(1): 31-36 (2001).
Lieb. Genome-wide mapping of protein-DNA interactions by chromatin immunoprecipitation and DNA microarray hybridization. Methods Mol Biol 224:99-109 (2003).
Lindahl et al., Quality control by DNA repair. Science 286(5446):1897-1905 (1999).
Liotta et al. Molecular profiling of Human Cancer, Nature Reviews/Genetics 1:48-56 (2000).
Litvinov et al. Gene expression analysis in Cutaneous T-Cell Lymphomas (CTCL) highlights disease heterogeneity and potential diagnostic and prognostic indicators. Oncoimmunology 6(5):e1306618 (2017).
Litvinov et al., The Use Of Transcriptional Profiling To Improve Personalized Diagnosis And Management Of Cutaneous T-Cell Lymphoma (CTCL). Clin Cancer Res. 21(12):2820-2829 (2015).
Livak et al. Analysis of Relative Gene Expression Data Using RealTime Quantitative PCR and the 2-delta delta Ct Method. Methods 25:402-408 (2001).
Ljland et al. Expression of Angiogenic and Immunosuppressive Factors by Uveal Melanoma Cell Lines, Melanoma Research, 9:445-450 (1999).
Lobmann et al. Expression of matrix-metalloproteinases and their inhibitors in the wounds of diabetic and non-diabetic patients. Diabetologia 45(7): 1011-1016 (2002).
Long et al. Improved statistical inference from DNA microarray data using analysis of variance and a Bayesian statistical framework. Analysis of global gene expression in *Escherichia coli* K12. J. Biol. Chem. 276(23):19937-19944 (2001).
Lu et al. MicroRNA expression profiles classify human cancers. Nature, 435(7043):834-838 (2005).
Lucas et al. Massive inflammatory syndrome and lymphocytic immunodeficiency in KARAP/DAP12-transgenic mice. Eur J Immunol 32(9):2653-2663 (2002).
Lucentini. Gene Association Studies Typically Wrong. The Scientist, 18(24):20 (2004).
Maddox et al. Elevated serum levels in human pregnancy of a molecule immunochemically similar to eosinophil granule major basic protein.J. Exp. Med. 158:1211-1226 (1983).
Mardis. Next-generation DNA sequencing methods. Annu. Rev. Genomics Hum. Genet. USA 9:387-402 (2008).
Margulies et al. Genome sequencing in microfabricated high-density picolitre reactors. Nature 437:376-380 (2005).
Marin et al., Molluscan shell proteins: primary structure, origin, and evolution. Current Topics in Developmental Biology 80:209-276 (2007).
Marionnet et al. Modulation of gene expression induced in human epidermis by environmental stress in vivo. J Invest Dermatol 121(6):1447-1458 (2003).
Marttin et al. A Critical Comparison of Methods to Quantify Stratum corneum removed by Tape Stripping. Skin Pharmacology 9:69-77 (1996).
Maxam et al. A new method for sequencing DNA. PNAS USA 74(2):560-564 (1977).
May et al. How Many Species are there on Earth? Science 241:1441-1449 (1988).
McCarty et al. Epidermal hyperplasia overlying human melanoma correlates with tumour depth and angiogenesis. Melanoma Res 13(4):379-387 (2003).

(56) References Cited

OTHER PUBLICATIONS

McKenzie et al. Interleukin-1 receptor antagonist inhibits subcutaneous B16 melanoma growth in vivo. Anticancer Research 16(1):437-441(1996).

McLean et al. Pharmacogenomic Analysis of Cytogenetic Response in Chronic Myeloid Leukemia Patients Treated with Imatinib. Clinical Cancer Research 10(1):155-165 (2004).

Melen et al. Human MxB protein, an interferon-alpha-inducible GTPase, contains a nuclear targeting signal and is localized in the heterochromatin region beneath the nuclear envelope. J Biol Chem 271(38):23478-23486 (1996).

Melt. Total Nucleic Acid Isolation System. Thermo Fisher Scientific, Part No. AM1983, P/N 1983M Revision D, 27. Retrieved from the Internet: < https://assets.thermofisher.com/TFS-Assets/LSG/manuals/cms_058167.pdf > on Jun. 2, 2018 (Oct. 2008) (pp. 1-31).

Méhul et al. Proteomic analysis of stratum corneum in Cutaneous T-Cell Lymphomas and psoriasis. Exp Dermatol 28(3):317-321 (2019).

Michael et al. Reduced accumulation of specific microRNAs in colorectal neoplasia. Mol Cancer Res. 1(12):882-891 (2003).

Mitchell et al. Global analysis of cellular transcription following infection with an HIV-based vector. Mol Ther 8(4):674-687 (2003).

Miyashiro et al. Molecular strategy for detecting metastatic cancers with use of multiple tumor-specific MAGE-A genes. Clinical Chemistry 47(3):505-512 (2001).

Molhuizen et al. Structural, biochemical, and cell biological aspects of the serine proteinase inhibitor SKALP/elafin/ESI. Biol Chem Hoppe Seyler 376(1):1-7 (1995).

Morhenn et al. A noninvasive method for quantifying and distinguishing inflammatory skin reactions. Journal of the American Academy of Dermatology 41(5 Pt 1):687-692(1999).

Muller-Decker et al. Arachidonic acid metabolism in primary irritant dermatitis produced by patch testing of human skin with surfactants. Toxicol Appl Pharmacol 153(1):59-67 (1998).

Muller-Decker et al. Keratinocyte-derived proinflammatory key mediators and cell viability as in vitro parameters of irritancy: a possible alternative to the Draize skin irritation test. Toxicol Appl Pharmacol 127(1):99-108 (1994).

Muthusamy et al. Epigenetic Silencing of Novel Tumor Suppressors in Malignant Melanoma. Cancer Research 66(23):11187-11193 (2006).

Nair et al. Virus-encoded microRNAs: novel regulators of gene expression. Trends Microbiol. 14(4):169-175 (2006).

NCBI GEO Profiles Database, DataSet Record GDS1989, excerpts (2 pages), Apr. 2006.

Nickoloff et al. Keratinocyte Interleukin-10 Expression is Upregulated in Tape-Stripped Skin, Poison Ivy Dermatitis, and Sezary Syndrome, but Not in Psoriatic Plaques. Clinical Immunology and Immunopathology 73(I):63-68 (1994).

Nickoloff et al. Perturbation of epidermal barrier function correlates with initiation of cytokine cascade in human skin. Journal of the American Academy of Dermatology 30(4):535-546 (1994).

Nikkola et al. High Expression Levels of Collagenase-1 and Stromelysin-1 Correlate with Shorter Disease-Free Survival in Human Metastic Melanoma. Int. J. Cancer 97:432-438 (2002).

Nurmi et al. High-performance real-time quantitative RT-PCR using lanthanide probes and a dual-temperature hybridization assay. Analytical Chemistry 74(14) 3525-3532 (2002).

O'Geen et al. Comparison of sample preparation methods for ChIP-chip assays. BioTechniques 41(5):577-580 (2006).

Ohmen et al. Overexpression of IL-10 in Atopic Dermatitis. The Journal of Immunology 154:1956-1963 (1995).

Olek et al. The pre-implantation ontogeny of the H19 methylation imprint Nat. Genet. 17(3):275-276 (1997).

Onodera et al. Macrophage migration inhibition factor up-regulates expression of matrix metalloproteinases in synovial fibroblasts of rheumatoid arthritis. J. Biol. Chem 275:444-450 (2000).

Orro et al., Development of TAP, a non-invasive test for qualitative and quantitative measurements of biomarkers from the skin surface. Biomarker Research 2: 20 doi: 10.1186/2050-7771-2-20 [1-12] (2014).

Page et al. The Power Atlas: a power and sample size atlas for microarray experimental design and research. BMC Bioinformatics 7:84 (2006).

Paik et al. A multigene assay to predict recurrence of tamoxifen-treated, node-negative breast cancer. N Eng J Med 351 (27):2817-2826 (2004).

Paludan et al. Use of the Polymerase Chain Reaction in Quantification of Interleukin 8 mRNA in Minute Epidermal Samples. Journal of Investigative Dermatology 99:830-835 (1992).

Pang et al. Pathway analysis using random forests classification and regression. Bioinformatic 22(16):2028-2036 (2006).

Pavey et al. Microarray expression profiling in melanoma reveals a BRAF mutation signature. Oncogene 23(23):4060-4067 (2004).

PCT/US1999/19012 International Preliminary Examination Report dated May 26, 2000.

PCT/US1999/19012 International Search Report dated Jan. 31, 2000.

PCT/US2002/20728 International Preliminary Examination Report dated Feb. 2, 2005.

PCT/US2002/20728 International Search Report dated Oct. 27, 2003.

PCT/US2005/10911 International Search Report dated Nov. 18, 2005.

PCT/US2005/10911 Written Opinion dated Nov. 18, 2005.

PCT/US2007/009686 International Search Report and Written Opinion dated Dec. 18, 2007.

PCT/US2008/062545 International Search Report dated Sep. 18, 2008.

PCT/US2008/062545 Written Opinion dated Sep. 18, 2008.

PCT/US2009/44035 International Search Report and Written Opinion dated Sep. 3, 2009.

PCT/US2014/044588 International Search Report and Written Opinion dated Oct. 20, 2014.

PCT/US2015/41599 International Search Report and Written Opinion dated Oct. 28, 2015.

PCT/US2016/30287 International Search Report and Written Opinion dated Aug. 16, 2016.

PCT/US2018/026902 International Search Report and Written Opinion dated Jul. 19, 2018.

PCT/US2019/018102 International Search Report and Written Opinion dated Jul. 1, 2019.

PCT/US2019/018102 Invitation to Pay Additional Fees dated May 9, 2019.

PCT/US2019/031203 International Invitation to Pay Additional Fees dated Jul. 11, 2019.

PCT/US2019/031203 International Search Report and Written Opinion dated Aug. 29, 2019.

Pelizzola et al. MEDME: an experimental and analytical methodology for the estimation of DNA methylation levels based on microarray derived MeDIP-enrichment. Genome Res. 18:1652-1659 (2008).

Perkins et al. A Noninvasive Method to Assess Skin Irritation and Compromised Skin Conditions Using Simple Tape Adsorption of Molecular Markers of Inflammation. Skin Res. Technol. 7(4):227-237 (2001).

Perkins et al. A non-invasive tape absorption method for recovery of inflammatory mediators to differentiate normal from compromised scalp conditions. Skin Res Technol 8(3):187-193 (2002).

Perkins et al. Development of a Noninvasive Method for Assessing Human Skin Irritation. The Toxicologist 36(1):365 (1997).

Petit-Zeman. MicroRNAs hit the big time. Nat Rev Drug Discov. 5(1):5 (2006).

Phan et al. Role of the C-terminal propeptide in the activity and maturation of gamma γ-interferon-inducible lysosomal thiol reductase (GILT). PNAS USA 99(19):12298-12303 (2002).

Pilcher et al. Role of matrix metalloproteinases and their inhibition in cutaneous wound healing and allergic contact hypersensitivity. Ann N Y Acad Sci 878:12-24 (1999).

(56) References Cited

OTHER PUBLICATIONS

Pistoor et al. Novel Predictive Assay for Contact Allergens Using Human Skin Explant Cultures, American Journal of Pathology 149(1):337-343 (1996).
Potts et al. Physical Methods for Studying Stratum Corneum Lipids, Seminars in Dermatology 11(2):129-138 (1992).
Prasad et al. Differential expression of degradome components in cutaneous squamous cell carcinomas. Mod Pathol 27(7):945-957 (2014).
Preston et al., Nonmelanoma cancers of the skin. New England Journal of Medicine 327(23):1649-1662 (1992).
Rauch et al. High-resolution mapping of DNA hypermethylation and hypomethylation in lung cancer. PNAS USA 105:252-257 (2008).
Raval et al. Loss of expression of tropomyosin-1, a novel class II tumor suppressor that induces anoikis, in primary breast tumors. Oncogene 22(40):6194-6203 (2003).
Rein et al. Identifying 5-methylcytosine and related modifications in DNA genomes. Nucleic Acids Res. 26(10):2255-2264 (1998).
Reinhart et al. The 21-nucleotide let-7 RNA regulates developmental timing in Caenorhabditis elegans. Nature 403(6772):901-906 (2000).
Rittie et al. UV-light-induced signal cascades and skin aging. Ageing Research Reviews 1:705-720 (2002).
Rivers et al. Non-invasive gene expression testing to rule out melanoma. Skin Therapy Letter 23(5):1-4 (2018).
Rivers et al. Ruling out Melanoma: A practical guide to improving performance through non-invasive gene expression testing. Skin Therapy Letter: Family Practice Edition 14(1):4-6 (2019).
Roberson et al., Psoriasis genetics: breaking the barrier. Trends in Genetics 26(9):415-423 (2010).
Rosenthal et al., Ultraviolet B light induces rapid changes in gene expression as detected by non-invasive, adhesive skin biopsies. [Poster Presentation, Orlando Florida] (Jun. 2019).
Rougier et al. In Vivo Correlation Between Stratum Corneum Resevoir Function and Percutaneous Absorption. J. Investigative Dermatology 81:275-278 (1983).
Rougier et al. In Vivo Percutaneous Penetration of Some organic Compounds Related to Anatomic Site in Humans: Predictive Assessment by the Stripping Method. J. Pharmaceutical Sciences 76:451-454 (1987).
Rougier et al. Regional variation in percutaneous absorption in man: measurement by the stripping method. Arch Dermatol Res. 278(6):465-469 (1986).
Rougier et al. The measurement of the stratum corneum reservoir. A predictive method for in vivo percutaneous absorption studies: influence of application time. J Invest Dermatol. 84(1):66-68 (1985).
Rowe. et al. Interleukin-4 and the Interleukin-4 Receptor in Allergic Contact Dermatitis. Contact Dermatitis 38(1):36-39 (1998).
Rudert. Genomics and proteomics tools for the clinic. Curr Opin. Mol. Ther.2(6):633-642 (2000).
Ryan et al. Cytokine mRNA Expression in Human Epidermis After Patch Treatment with Rhus and Sodium Lauryl Sulfate. American Journal of Contact Dermatitis 10(3):127-135 (1999).
Sadri et al. Rapid analysis of DNA methylation using new restriction enzyme sites created by bisulfite modification. Nucleic Acids Res. 24:5058-5059 (1996).
Saiki et al. A Novel Method For The Detection of Polymorphic Restriction Sites By Cleavage of Oligonucleotid Probes: Application To Sickle-Cell AnemiaBioTechnology 3:1008-1012 (1985).
Saito-Hisaminato et al. Genome-wide profiling of gene expression in 29 normal human tissues with a cDNA microarray. DNA Res 9:35-45 (2002).
Samal et al. Cloning and characterization of the cDNA encoding a novel human pre-B-cell colony-enhancing factor. Mol Cell Biol 14(2):1431-1437 (1994).
Sanger et al. DNA sequencing with chain-terminating inhibitors. PNAS USA 74(12):5463-5467 (1977).
Satagopan et al. A statistical perspective on gene expression data analysis. Stat Med 22(3):481-499 (2003).

Seftor et al. Cooperative interactions of laminin 5 gamma2 chain, matrix metalloproteinase-2, and membrane type-1-matrix/metalloproteinase are required for mimicry of embryonic vasculogenesis by aggressive melanoma. Cance Res 61(17):6322-6327 (2001).
Shattuck et al. MGSA/GRO transcription is differentially regulated in normal retinal pigment epithelial and melanoma cells. Molecular and Cellular Biology 14(1):791-802 (1994).
Shen et al., Epigenetic and genetic dissections of UV-induced global gene dysregulation in skin cells through multi-omics analyses. Scientific Reports 7:42646; doi: 10.1038/srep42646 [1-12] (2017).
Shen et al., Transcriptome analysis identifies the dysregulation of ultraviolet target genes in human skin cancers. PLoS One 11(9):e0163054 [1-14] (2016).
Shin et al. Lesional gene expression profiling in cutaneous T-cell lymphoma reveals natural clusters associated with disease outcome. Blood 110(8):3015-3027 (2007).
Shintani et al. Growth-Regulated Oncogene-1 Expression is Associated with Angiogenesis and Lymph Node Metastasis in Human Oral Cancer. Oncology 66:316-322 (2004).
Shiraishi et al. Isolation of DNA fragments associated with methylated CpG islands in human adenocarcinomas of the lung using a methylated DNA binding column and denaturing gradient gel electrophoresis. PNAS USA 96(6):2913-2918 (1999).
Si et al. Expression of the Neuroglandular Antigen and Analogues in Melanoma. CD9 Expression Appears Inversely Related to Metastic Potential of Melanoma. Int. J. Cancer 54:37-43 (1993).
Siegel et al. Further consideration of the pigmented lesion assay-reply. JAMA Dermatol 155(3):393-394 (2019).
Slack et al. MicroRNAs as a potential magic bullet in cancer. Future Oncol. 2(1):73-82 (2006).
SLAS. From Laboratory to Clinic: Novel Skin Sampling Technique Simplifies Disease Detection. Available at https://www.slas.org/eln/from-laboratory-to-clinic-novel-skin-sampling-technique-simplifies-disease-detection/ (2012) ((pgs).
Smyth et al. Statistical issues in cDNA microarray data analysis. Methods Mol Biol 224:111-136 (2003).
Soni et al. Progress toward ultrafast DNA sequencing using solid-state nanopores. Clin. Chem. 53:1996-2001 (2007).
Soufir et al. Association Between Endothelin Receptor B Nonsynonymous Variants and Melanoma Risk. Journ. Nat'l. Cancer Inst. 97(17):1297-1301 (2005).
Stege et al., Enzyme plus light therapy to repair DNA damage in ultraviolet-B-irradiated human skin. Proceedings of the National Academy of Sciences 97(4):1790-1795 (2000).
Steinert et al., Small proline-rich proteins are cross-bridging proteins in the cornified cell envelopes of stratified squamous epithelia. Journal of Structural Biology 122(1-2):76-85 (1998).
Stolz et al. Semiquantitative analysis of histologic criteria in thin malignant melanomas. J Am Acad Dermato. 20(6):1115-1120 (1989).
Stuart et al. In silico dissection of cell-type—associated patterns of gene expression in prostate cancer. PNAS USA 101(2):615-620 (2004).
Su et al. Identification of tumor-suppressor genes using human melanoma cell lines UACC903, UACC903(+6), and SRS3 by comparison of expression profiles. Mol Carcinog 28(2):119-127 (2000).
Suzuki et al. Control selection for RNA quantitation. Biotechniques 29(2):332-337 (2000).
Syrokou et al. Synthesis and expression of mRNA encoding for different versican splice variants is related to the aggregation of human epithelial mesothelioma cells. Anticancer Res 22(6C):4157-4162 (2002).
Tagawa. A microRNA cluster as a target of genomi amplification in malignant lymphoma. Leukemia. 19(11):2013-2016 (2005).
Takashi et al. Novel melanoma antigen, FCRL/FREB, identified by cDNA profile comparison using DNA chip Are immunogenic in multiple melanoma patients. International Journal of Cancer 114(2):283-290 (2005).
Thatcher et al. miRNA Expression Analysis During Normal Zebrafish Development and Following Inhibition of the Hedgehog and Notch Signaling Pathways. Developmental Dynamics 236:2172-2180 (2007).

(56) References Cited

OTHER PUBLICATIONS

Thiele et al. Macromolecular carbonyls in human stratum corneum: a biomarker for environmental oxidant exposure? FEBS letters 422:403-406 (1998).
Thiele et al. Protein Oxidation in Human Stratum Corneum: Susceptibility of Keratins to Oxidation In Vitro and Presence of a Keratin Oxidation Gradient In Vivo. Journal of Investigative Dermatology 113:335-339 (1999).
Thoma F. Light and dark in chromatin repair: repair of UV-induced DNA lesions by photolyase and nucleotide excision repair. The EMBO Journal 18(23):6585-6598 (1999).
Thorey et al. The Ca2+-binding proteins S100A8 and S100A9 are encoded by novel injury-regulated genes. J Biol Chem 276(38):35818-35825 (2001).
Tibshirani et al. Diagnosis of multiple cancer types by shrunken centroids of gene expression. PNAS USA 99(10):6567-6572 (2002).
Tomic-Canic et al. Epidermal signal transduction and transcription factor activation in activated keratinocytes. J Dermatol Sci 17(3):167-181 (1998).
Torabian et al. Biomarkers for melanoma.Current Opinion in Oncology 17:167-171 (2005).
Torre et al. Epidermal Cells on Stubs Used for Detection of GSR with SEM-EDX: Analysis of DNA Polymorphisms. Journal of Forensic Sciences (JFSCA) 41(4):658-659 (1996).
Toyota et al. Identification of differentially methylated sequences in colorectal cancer by methylated CpG island amplification. Cancer Res. 59:2307-2312 (1999).
Tricarico et al. Quantitative real-time reverse transcription polymerase chain reaction: normalization to rRNA or single housekeeping genes is inappropriate for human tissue biopsies. Anal Biochem 309(2):293-300 (2002).
Ulfgren et al. An immunohistochemical analysis of cytokine expression in allergic and irritant contact dermatitis. Acta Derm Venereol 80(3):167-170 (2000).
U.S. Appl. No. 09/375,609 Office Action dated Dec. 18, 2003.
U.S. Appl. No. 09/375,609 Office Action dated Jan. 31, 2001.
U.S. Appl. No. 09/375,609 Office Action dated Jul. 12, 2001.
U.S. Appl. No. 09/967,658 Office Action dated Apr. 22, 2003.
U.S. Appl. No. 09/967,658 Office Action dated Jun. 6, 2003.
U.S. Appl. No. 09/970,617 Office Action dated Jun. 2, 2004.
U.S. Appl. No. 09/972,531 Office Action dated Jun. 14, 2004.
U.S. Appl. No. 09/976,356 Office Action dated Sep. 24, 2003.
U.S. Appl. No. 09/976,361 Office Action dated Jun. 28, 2004.
U.S. Appl. No. 09/976,613 Office Action dated Jun. 28, 2004.
U.S. Appl. No. 10/184,846 Office Action dated May 5, 2005.
U.S. Appl. No. 10/184,846 Office Action dated Sep. 26, 2006.
U.S. Appl. No. 10/816,457 Office Action dated Mar. 13, 2006.
U.S. Appl. No. 10/816,457 Office Action dated Sep. 5, 2005.
U.S. Appl. No. 11/710,661 Office Action dated Jan. 11, 2010.
U.S. Appl. No. 11/710,661 Office Action dated Jul. 14, 2009.
U.S. Appl. No. 11/710,661 Office Action dated Jul. 21, 2010.
U.S. Appl. No. 11/788,644 Office Action dated Jul. 25, 2008.
U.S. Appl. No. 12/114,669 Office Action dated Aug. 5, 2010.
U.S. Appl. No. 12/114,669 Office Action dated Jan. 6, 2011.
U.S. Appl. No. 12/114,669 Office Action dated Jun. 21, 2011.
U.S. Appl. No. 12/114,669 Office Action dated Jun. 30, 2014.
U.S. Appl. No. 12/114,669 Office Action dated Nov. 17, 2009.
U.S. Appl. No. 12/114,669 Office Action dated Oct. 19, 2015.
U.S. Appl. No. 12/114,669 Office Action dated Oct. 27, 2014.
U.S. Appl. No. 12/991,685 Office Action dated Mar. 13, 2013.
U.S. Appl. No. 12/991,685 Office Action dated Nov. 4, 2013.
U.S. Appl. No. 13/136,278 Office Action dated Mar. 14, 2012.
U.S. Appl. No. 13/136,278 Office Action dated Sep. 25, 2012.
U.S. Appl. No. 13/847,434 Office Action dated Jul. 29, 2015.
U.S. Appl. No. 13/847,434 Office Action dated Mar. 21, 2014.
U.S. Appl. No. 13/847,434 Office Action dated Nov. 18, 2014.
U.S. Appl. No. 13/847,434 Office Action dated Oct. 10, 2013.
U.S. Appl. No. 14/172,784 Office Action dated Apr. 23, 2015.
U.S. Appl. No. 14/199,900 Notice of Allowance dated Mar. 30, 2015.
U.S. Appl. No. 14/199,900 Office Action dated Dec. 10, 2014.
U.S. Appl. No. 14/199,900 Pending Claims.
U.S. Appl. No. 14/208,155 Office Action dated Jul. 8, 2015.
U.S. Appl. No. 14/208,155 Office Action dated Nov. 20, 2014.
U.S. Appl. No. 14/806,453 Office Action dated Oct. 25, 2016.
U.S. Appl. No. 14/832,966 Office Action dated Apr. 12, 2018.
U.S. Appl. No. 14/832,966 Office Action dated Aug. 10, 2017.
U.S. Appl. No. 14/832,966 Office Action dated Nov. 16, 2018.
Ushijima et al. Methylation-Sensitive Representational Difference Analysis (MS-RDA). Methods Mol Biol 507:117-130 (2009).
Vallejo et al. Central role of thrombospondin-1 in the activation and clonal expansion of inflammatory T cells. J Immunol 164(6):2947-2954 (2000).
Van Der Molen et al. Tape stripping of human stratum corneum yields cell layers that originiate from various depths because of furrows in the skin. Archives of Dermatological Research 289:514-518 (1997).
Van Der Valk et al. A functional study of the skin barrier to evaporative water loss by means of repeated cellophane-tape stripping. Clinical and Experimental Dermatology 15(3):180-182 (1990).
Van Hoogdalem. Assay of Erythromycin in Tape Strips of Human Stratum corneum and Some Preliminary results in Man. Skin Pharmacol 5:124-128 (1992).
Van Ruissen et al. Differential effects of detergents on keratinocyte gene expression. J Invest Dermatol 110(4):358-363 (1998).
Vandesompele et al. Accurate normalization of real-time quantitative RT-PCR data by geometric averaging of multiple internal control genes. Genome Biology 3(7):-112 (2002).
Vaqué et al. PLCG1 mutations in cutaneous T-cell lymphomas. Blood 123(13):2034-43 (2014).
Verhoef. The phagocytic process and the role of complement in host defense. J Chemother 3(Suppl 1):93-97 (1991).
Vermeer et al. Segregation of receptor and ligand regulates activation of epithelial growth factor receptor. Nature 422(6929):322-326 (2003).
Volinia et al. A microRNA expression signature of human solid tumors defines cance gene targets. PNAS USA 103(7):2257-2261 (2006).
Wachsman et al. Differentiation of melanoma from dysplastic nevi in suspicious pigmented skin lesions by non-invasive tape stripping. Journal of Dermatology 127(Supp 1s):S145 (2007).
Wachsman et al. Noninvasiave genomic detection of melanoma, British Journal of Dermatology 164:797-806 (2011).
Wang et al. Melanoma-restricted Genes, J. of Translational Medicine 2:34 pp. 1-14 (2004).
Wang et al. MGSA/GRO-mediated melanocyte transformation involves induction of Ras expression. Oncogene 19:4647-4659 (2000).
Washington Report: Skin Tape Stripping Method for Generic Dermatologic Drug Approval Remains in Question, http://www.aadassociation.org/old/washReports/dec99_washrep.html (1999).
Wassem et al. Keratin 15 expression in stratified epithelia: down regulation in activated keratincytes. Journal of Investigative Dermatology 113:362-269 (1999).
Weber et al. Chromosome-wide and promoter-specific analyses identify sites of differential DNA methylation in normal and transformed human cells. Nat. Genet. 37:853-862 (2005).
Weigand et al. Removal of Stratum Corneum in Vivo: An Improvement of the Cellophane Tape Strapping Technique. The Journal of Investigative Dermatology 60(2):84-87 (1973).
Weinstock. Early detection of melanoma. JAMA 284:886-889 (2000).
Welss et al. Hurpin is a selective inhibitor of lysosomal cathepsin L and protects keratinocytes from ultraviolet-induced apoptosis. Biochemistry 42(24):7381-7389 (2003).
Werfel et al. Cytokines as Mediators of Allergic Tissue Response. Allergologie Dustrie Verlag Muenchen-Deisenhofen, DE 20(11):546-550 (1997).
Werfel et al. High IL-4 Secretion from Skin-Derived Nickel Specific T-lymphocytes is Associated with Atopy and Acute Eczema are associated with in Allergic Contact Dermatitis. Journal of Allergy and Clinical Immunology 101(1, Part2):S129 (1998).
Whipple et al. DNA microarrays in otolaryngology—head and neck surgery. Otolaryngol Head Neck Surg 127(3):196-204 (2002).

(56) References Cited

OTHER PUBLICATIONS

Wojdacz et al. Methylation-sensitive high resolution melting (MS-HRM): a new approach for sensitive and high-throughput assessment of methylation. Nucleic Acids Res. 35(6):e41 (2007).
Wojdacz et al. Methylation-sensitive high-resolution melting. Nature Protocols 3(12):1903-1908 (2008).
Wolf et al., Topical treatment with liposomes containing T4 endonuclease V protects human skin in vivo from ultraviolet-induced upregulation of interleukin-10 and tumor necrosis factor-α. Journal of Investigative Dermatology 114.1:149-156 (2000).
Wolyn et al. Light-response quantitative trait loci identified with composite interval and extreme array mapping in *Arabidopsis thaliana*. Genetics 167(2):907-917 (2004).
Wong et al. Analysis of RNA recovery and gene expression in the epidermis using non-invasive tape stripping. J Dermatol Science 44:81-92 (2006).
Wong et al. Use of RT-PCR and DNA Microarrays to Characterize RNA Recovered by Non-invasive Tape Harvesting of Normal and Inflamed Skin. Journal of Investigative Dermatology 123(1):159-167 (2004).
Wu et al. Preprocessing of oligonucleotide array data. Nat Biotechnol 22(6):656-658; author reply 658 (2004).
Wu et al. Stochastic models inspired by hybridization theory for short oligonucleotide arrays. J Comput Bio. 12(6):882-893 (2005).
Xiong et al. COBRA: a sensitive and quantitative DNA methylation assay. Nucleic Acids Res. 25:2532-2534 (1997).
Xu et al. Expression of Cytokine mRNAs in the Draining Lymph Nodes Following Contact Sensitivity in Mice. Toxicology Methods 7:137-148 (1997).
Xu et al. RT-PCR Analysis of In Vivo Cytokine Profiles in Murine Allergic Contact Dermatitis to DNCB. Toxicology Methods. 6:23-31 (1996).
Yanaihara et al. Unique microRNA molecular profiles in lung cancer diagnosis and prognosis. Cancer Cell. 9(3):189-198 (2006).
Yao et al. An adhesive patch-based skin biopsy device for molecular diagnostics and skin microbiome studies. J Drugs Dermatol 16:979-986 (2017).
Yao et al. Analytical Characteristics of a Noninvasive Gene Expression Assay for Pigmented Skin Lesions. Assay Drug Del Technol 14(6):355-363 (2016).
Yarosh et al., Pyrimidine dimer removal enhanced by DNA repair liposomes reduces the incidence of UV skin cancer in mice. Cancer Research 52(15):4227-4231 (1992).
Yarosh et al., Xeroderma pigmentosum study group. Effect of topically applied T4 endonuclease V in liposomes on skin cancer in xeroderma pigmentosum: a randomised study. The Lancet 357(9260):926-929 (2001).
Yawalkar et al. Pathogenesis of Drug-Induced Exanthema. Int Arch Allergy immunol. 124:336-338 (2001).
Yi et al. Morphogenesis in skin is governed by discrete sets of differentially expressed microRNAs. Nature Genetics 38(3):356-362 (2006).
Zou et al., Strand opening by the UvrA2B complex allows dynamic recognition of DNA damage. The EMBO Journal 18(17):4889-4901 (1999).
Co-pending U.S. Appl. No. 17/534,177, inventors Dobak; John Daniel et al., filed Nov. 23, 2021.
Crow. Type I interferon in the pathogenesis of lupus. Immunol 192:5459-5468 (2014).
Hayre. Oxytocin Levels Inversely Correlate With Skin Age Score and Solar Damage. J Drugs Dermatol 19(12):1146-1148 (2020).
Jolivet et al. Solutions for purifying nucleic acids by solid phase reversible immobilization (SPRI). Philippe Jolivet and Joseph W. Foley Ludmer Centre for Neuroinformatics and Mental Health Oct. 21, 2015 pp. 1-6.
Mok. The Jakinibs in systemic lupus erythematosus: progress and prospects. Expert Opin Investig Drugs. 28(1):85-92 (2019).
PCT/US2021/060641 Invitation to Pay Additional Fees dated Jan. 26, 2022.
TechNote 302. Bangs Laboratories, p. 1-5, Jun. 2016.
U.S. Appl. No. 16/603,435 Office Action dated Mar. 10, 2022.
U.S. Appl. No. 16/874,473 Office Action dated Jan. 24, 2022.
Zaba et al. Effective treatment of psoriasis with etanercept is linked to suppression of IL-17 signaling, not immediate response TNF genes. J Allergy Clin Immunol 124:1022 (2009).
Bogaczewicz et al. Medium-dose ultraviolet AI phototherapy and mRNA expression of TSLP, TARC, IL-5, and IL-13 in acute skin lesions in atopic dermatitis. Int'l J Derm 55(8):856-863 (2015).
Meng et al. New mechanism underlying IL-31-induced atopic dermatitis. J Allergy Clin Immunol 141(5):1677-1689 (2018).
Nobbe et al. IL-31 Expression by Inflammatory Cells is Preferentially Elevated in Atopic Dermatitis. Acta Derm Venereol 92(1):24-8 (2012).
PCT/US2022/018274 International Search Report and Written Opinion dated May 23, 2022.
Salz et al. ABSTRACT 101: Scurfy mice show autoimmune skin inflammation with features of atopic dermatitis including systemic upregulation of IL-31 and TSLP. J. Invest Dermatol 132:S19 (2012).
U.S. Appl. No. 16/874,473 Office Action dated Jun. 7, 2022.
Chng et al. Whole metagenome profiling reveals skin microbiome-dependent susceptibility to atopic dermatitis flare. Nat Microbiol 1(9):16106 (2016).
Lovly et al. Routine multiplex mutational profiling of melanomas enables enrollment in genotype-driven therapeutic trials. PLoS One 7(4):e35309 (2012).
U.S. Appl. No. 17/354,894 Office Action dated Dec. 19, 2022.

\* cited by examiner

| Genes Identified | Litvinov et al., 2017 | Dulmage and Geskin, 2013 | Litvinov et al., 2015 | Booken et al., 2008 | Shin et al., 2007 | Candidate Genes as Dx.Biomarker* |
|---|---|---|---|---|---|---|
| TOX | v | v | v | | | TOX |
| FYB | v | | v | | v | FYB |
| LEF1 | v | | v | | v | LEF1 |
| CCR4 | v | | v | | v | CCR4 |
| ITK | v | | v | | | ITK |
| EED | v | | | | | |
| IL-26 | v | | v | | v | IL26 |
| POU2AF | v | | | | v | POU2AF1 |
| STAT5A | v | v | v | | | STAT5A |
| BLK | v | | | | | |
| GTSF1 | v | | v | | | GTSF1 |
| PSORS1C2 | v | | | | | |
| TWIST1 | | v | | | | |
| KIR3DL2 | | v | | | | |
| PLS3 | | v | | v | | PLS3 |
| SATB1 | | v | | | | |
| BCL2 | | v | | | | |
| JUNB | | v | | | | |
| TGFBR2 | | v | | | | |
| CCL18 | | | v | | | |
| CCL26 | | | v | | | |
| T3JAM | | | v | | v | T3JAM |
| MMP12 | | | v | | v | MMP12 |
| LCK | | | v | | v | LCK |
| GNLY | | | v | | v | GNLY |
| IL2RA | | | v | | | |
| IL22 | | | v | | | |
| SYCP1 | | | v | | | |
| DNM3 | | v | | v | | DNM3 |
| IGFL2 | | | | v | | |
| CD01 | | | | v | | CD01 |
| NEDD4L | | v | | v | | NEDD4L |
| KLHDC5 | | | | v | | |
| TNFSF11 | | v | | v | v | TNFSF11 |

| | N | FYB | LEF1 | GNLY | DNM3 | ITK | IL26 | STAT5 |
|---|---|---|---|---|---|---|---|---|
| Average | ΔCt_CTCL | 12 | 10.02 | 10.95 | 11.03 | 11.81 | 10.85 | 13.23 | 7.49 |
| | ΔCt_NML | 11 | 12.12 | 10.39 | 13.74 | 13.39 | 13.10 | 14.03 | 10.32 |
| Median | ΔCt_CTCL | 12 | 9.68 | 9.27 | 12.48 | 11.39 | 10.02 | 13.77 | 7.14 |
| | ΔCt_NML | 11 | 12.15 | 10.58 | 14.06 | 14.06 | 14.06 | 14.21 | 10.00 |
| | ΔΔAverage | | -2.09 | 0.57 | -2.71 | -1.58 | -2.25 | -0.80 | -2.83 |
| | ΔΔmedian | | -2.47 | -1.31 | -1.58 | -2.67 | -4.04 | -0.45 | -2.85 |
| | p-value | | 0.048 | 0.716 | 0.043 | 0.111 | 0.076 | 0.383 | 0.021 |

FIG. 7B

| | N | TRAF3IP3 | TNFSF11 | CCL27 | CXCL10 | CXCL8 | CXCL9 | TNF |
|---|---|---|---|---|---|---|---|---|
| Average | ΔCt_CTCL | 12 | 7.27 | 12.41 | 11.41 | 11.34 | 4.17 | 10.28 | 9.63 |
| | ΔCt_NML | 11 | 9.73 | 13.08 | 11.88 | 13.84 | 7.36 | 12.65 | 12.16 |
| Median | ΔCt_CTCL | 12 | 7.18 | 13.38 | 11.95 | 13.31 | 5.01 | 13.44 | 8.73 |
| | ΔCt_NML | 11 | 9.64 | 14.06 | 13.20 | 14.19 | 8.26 | 13.43 | 13.20 |
| | ΔΔAverage | | -2.46 | -0.68 | -0.47 | -2.50 | -3.18 | -2.37 | -2.53 |
| | ΔΔmedian | | -2.45 | -0.69 | -1.25 | -0.87 | -3.25 | 0.01 | -4.47 |
| | p-value | | 0.004 | 0.566 | 0.682 | 0.054 | 0.056 | 0.188 | 0.067 |

| Gene Symbol | Entrez Gene ID | Gene Name | Gene Aliases |
|---|---|---|---|
| FYB | 2533 | FYN binding protein | ADAP; PRO0823; SLAP-130; SLAP130 |
| LEF1 | 51176 | lymphoid enhancer binding factor 1 | LEF-1; TCF10; TCF1ALPHA; TCF7L3 |
| GNLY | 10578 | granulysin | D2S69E; LAG-2; LAG2; NKG5; TLA519 |
| DNM3 | 26052 | dynamin 3 | Dyna III |
| ITK | 3702 | IL2 inducible T-cell kinase | EMT; LPFS1; LYK; PSCTK2 |
| IL26 | 55801 | interleukin 26 | AK155; IL-26 |
| STAT5 | 6776 | signal transducer and activator of transcription 5A | MGF; STAT5 |
| TRAF3IP3 | 80342 | TRAF3 interacting protein 3 | T3JAM |
| TNFSF11 | 8600 | tumor necrosis factor superfamily member 11 | CD254; hRANKL2; ODF; OPGL; OPTB2; RANKL; sOdf; TNLG6B; TRANCE |
| CCL27 | 10850 | C-C motif chemokine ligand 27 | ALP; CTACK; CTAK; ESKINE; ILC; PESKY; SCYA27 |
| CXCL10 | 3627 | C-X-C motif chemokine ligand 10 | C7; crg-2; gIP-10; IFI10; INP10; IP-10; mob-1; SCYB10 |
| CXCL8 | 3576 | C-X-C motif chemokine ligand 8 | GCP-1; GCP1; IL8; LECT; LUCT; LYNAP; MDNCF; MONAP; NAF; NAP-1; NAP1 |
| CXCL9 | 4283 | C-X-C motif chemokine ligand 9 | CMK; crg-10; Humig; MIG; SCYB9 |
| TNF | 7124 | tumor necrosis factor | DIF; TNF-alpha; TNFA; TNFSF2; TNLG1F |
| TOX | 9760 | thymocyte selection associated high mobility group box | TOX1 |
| CCR4 | 1233 | C-C motif chemokine receptor 4 | CC-CKR-4; CD194; ChemR13; CKR4; CMKBR4; HGCN:14099; K5-5 |
| POU2AF1 | 5450 | POU class 2 associating factor 1 | BOB1; OBF-1; OBF1; OCAB |
| GTSF1 | 121355 | gametocyte specific factor 1 | FAM112B |
| PLS3 | 5358 | plastin 3 | BMND18; T-plastin |
| MMP12 | 4321 | matrix metallopeptidase 12 | HME; ME; MME; MMP-12 |
| LCK | 3932 | LCK proto-oncogene, Src family tyrosine kinase | IMD22; LSK; p56lck; pp58lck; YT16 |
| NEDD4L | 23327 | neural precursor cell expressed, developmentally down-regulated 4-like, E3 ubiquitin protein ligase | hNEDD4-2; NEDD4-2; NEDD4.2; RSP5 |

FIG. 8A

| Gene Symbol | Chromosome Location | UniGene | Gene family or Superfamily |
|---|---|---|---|
| FYB | Chr.5: 39105252 - 39274523 on Build GRCh38 | Hs.370503 | a member of the FYN-binding protein family |
| LEF1 | Chr.4: 108047545 - 108168956 on Build GRCh38 | Hs.743478 | a member of the lymphoid enhancer binding factor family |
| GNLY | Chr.2: 85694291 - 85698854 on Build GRCh38 | Hs.105806 | a member of the saposin-like protein (SAPLIP) family |
| DNM3 | Chr.1: 171841478 - 172418466 on Build GRCh38 | Hs.654775 | a member of the dynamin family |
| ITK | Chr.5: 157180896 - 157255185 on Build GRCh38 | Hs.558348 | a member of the TEC family of kinases |
| IL26 | Chr.12: 68201349 - 68225791 on Build GRCh38 | Hs.272350 | a member of IL super family |
| STAT5 | Chr.17: 42287547 - 42311943 on Build GRCh38 | Hs.437058 | one of the seven-membered STAT family |
| TRAF3IP3 | Chr.1: 209756032 - 209782323 on Build GRCh38 | Hs.147434 | a member of the TRAF3 interacting protein family |
| TNFSF11 | Chr.13: 42562736 - 42608013 on Build GRCh38 | Hs.333791 | one of TNF Superfamily Member |
| CCL27 | Chr.9: 34661883 - 34662692 on Build GRCh38 | Hs.648124 | a member of the C-c motif chemokine ligand (CCL) super family |
| CXCL10 | Chr.4: 76021116 - 76023536 on Build GRCh38 | Hs.632586 | a member of the CXC chemokine family. |
| CXCL8 | Chr.4: 73740506 - 73743716 on Build GRCh38 | Hs.624 | a member of the CXC chemokine family. |
| CXCL9 | Chr.4: 76001342 - 76007523 on Build GRCh38 | Hs.77367 | a member of the CXC chemokine family. |
| TNF | Chr.6: 31575567 - 31578336 on Build GRCh38 | | one of TNF Superfamily Member |
| TOX | Chr.8: 58805418 - 59119293 on Build GRCh38 | Hs.491805 | a member of the Thymocyte Selection Associated High Mobility Group Box family |
| CCR4 | Chr.3: 32951555 - 32955312 on Build GRCh38 | Hs.184926 | a member of the C-C chemokine receptor type family |
| POU2AF1 | Chr.11: 111352251 - 111379432 on Build GRCh38 | Hs.654525 | a member of the POU domain class 2-associating factor or Oct binding factor family |
| GTSF1 | Chr.12: 54455952 - 54473602 on Build GRCh38 | Hs.524476 | a member of the Gametocyte-Specific Factor family |
| PLS3 | Chr.X: 115560850 - 115650861 on Build GRCh38 | Hs.496622 | a member of plastin family |
| MMP12 | Chr.11: 102862729 - 102875034 on Build GRCh38 | Hs.1695 | a member of the Matrix Metallopeptidase family |
| LCK | Chr.1: 32251239 - 32286167 on Build GRCh38 | Hs.470627 | a member of the lymphocyte-specific protein tyrosine kinase family |
| NEDD4L | Chr.18: 58044362 - 58401540 on Build GRCh38 | Hs.185677 | a member of the NEDD4 family of E3 HECT domain ubiquitin ligases |

FIG. 8B

GENE CLASSIFIERS AND USES THEREOF IN SKIN CANCERS

CROSS-REFERENCE

This application claims the benefit of U.S. Provisional Application No. 62/824,136, filed Mar. 26, 2019, which application is incorporated herein by reference in its entirety.

BACKGROUND OF THE DISCLOSURE

Skin diseases are some of the most common human illnesses and represent an important global burden in healthcare. Three skin diseases are in the top ten most prevalent diseases worldwide, and eight fall into the top 50. When considered collectively, skin conditions range from being the second to the 11th leading causes of years lived with disability.

SUMMARY OF THE DISCLOSURE

Disclosed herein, in certain embodiments, is a method of detecting the presence of a skin cancer based on molecular risk factors. In some instances, the skin cancer is a non-Hodgkin lymphoma. In some instances, the skin cancer is cutaneous T cell lymphoma (CTCL). In some instances, the non-Hodgkin lymphoma is CTCL. In some cases, the skin cancer is mycosis fungoides (MF) or Sézary syndrome (SS).

Disclosed herein, in certain embodiments, is a method of detecting gene expression level of FYN binding protein (FYB), IL2 inducible T-cell kinase (ITK), interleukin 26 (IL26), signal transducer and activator of transcription 5A (STAT5A), TRAF3 interacting protein 3 (TRAF3IP3), granulysin (GNLY), dynamin 3 (DNM3), tumor necrosis factor superfamily member 11 (TNFSF11), or a combination thereof in a subject in need thereof, comprising: (a) isolating nucleic acids from a skin sample obtained from the subject, wherein the skin sample comprises cells from the stratum corneum; and (b) detecting the expression levels of FYB, ITK, IL26, STAT5A, TRAF3IP3, GNLY, DNM3, TNFSF11, or a combination thereof, by contacting the isolated nucleic acids with a set of probes that recognizes FYB, ITK, IL26, STAT5A, TRAF3IP3, GNLY, DNM3, TNFSF11, or a combination thereof, and detects binding between FYB, ITK, IL26, STAT5A, TRAF3IP3, GNLY, DNM3, TNFSF11, or a combination thereof and the set of probes. In some embodiments, the method comprises detecting the expression levels of ITK, STAT5A, and TNFSF11. In some embodiments, the method comprises detecting the expression levels of ITK, IL26, STAT5A, and TNFSF11. In some embodiments, the method comprises detecting the expression levels of FYB, ITK, IL26, STAT5A, and TNFSF11. In some embodiments, the method comprises detecting the expression levels of FYB, ITK, IL26, STAT5A, TRAF3IP3, and TNFSF11. In some embodiments, the method comprises detecting the expression levels of FYB, ITK, IL26, STAT5A, TRAF3IP3, DNM3, and TNFSF11. In some embodiments, the method comprises detecting the expression levels of FYB, ITK, IL26, STAT5A, TRAF3IP3, GNLY, DNM3, and TNFSF11. In some embodiments, the expression level is an elevated gene expression level, compared to a gene expression level of an equivalent gene from a control sample. In some embodiments, the gene expression level of FYB, ITK, IL26, STAT5A, TRAF3IP3, DNM3, TNFSF11, or a combination thereof is elevated. In some embodiments, the expression level is a down-regulated gene expression level, compared to a gene expression level of an equivalent gene from a control sample. In some embodiments, the gene expression level of GNLY is down-regulated. In some embodiments, the set of probes recognizes at least one but no more than eight genes. In some embodiments, the method further comprises detecting the expression levels of TOX, LEF1, CCR4, POU2AF1, GTSF1, PLS3, MMP12, LCK, NEDD4L, or a combination thereof. In some embodiments, the detecting comprises contacting the isolated nucleic acids with an additional set of probes that recognizes TOX, LEF1, CCR4, POU2AF1, GTSF1, PLS3, MMP12, LCK, NEDD4L, or a combination thereof, and detects binding between TOX, LEF1, CCR4, POU2AF1, GTSF1, PLS3, MMP12, LCK, NEDD4L, or a combination thereof and the additional set of probes. In some embodiments, the additional set of probes recognizes one but no more than nine genes. In some embodiments, the cells from the stratum corneum comprise T cells or components of T cells. In some embodiments, the cells from the stratum corneum comprise keratinocytes. In some embodiments, the skin sample does not comprise melanocytes. In some embodiments, the skin sample is obtained by applying an adhesive patch to a skin region of the subject in a manner sufficient to adhere cells to the adhesive patch, and removing the adhesive patch from the skin region in a manner sufficient to retain the adhered cells to the adhesive patch. In some embodiments, the skin sample is obtained by applying a plurality of adhesive patches to a skin region of the subject in a manner sufficient to adhere cells to each of the adhesive patches, and removing each of the adhesive patches from the skin region in a manner sufficient to retain the adhered cells to each of the adhesive patches. In some embodiments, the plurality of adhesive patches comprises at least 4 adhesive patches. In some embodiments, the skin region is a skin lesion region. In some embodiments, the subject is suspected of having cutaneous T cell lymphoma (CTCL). In some embodiments, the subject is suspected of having mycosis fungoides (MF). In some embodiments, the subject is suspected of having Sézary syndrome (SS). In some embodiments, the subject is a human.

Disclosed herein, in certain embodiments, is a method of detecting gene expression levels from a first gene classifier and a second gene classifier in a subject in need thereof, comprising: (a) isolating nucleic acids from a skin sample obtained from the subject, wherein the skin sample comprises cells from the stratum corneum; (b) detecting the expression levels of one or more genes from the first gene classifier: FYB, ITK, IL26, STAT5A, TRAF3IP3, GNLY, DNM3, and TNFSF11, by contacting the isolated nucleic acids with a set of probes that recognizes one or more genes from the first gene classifier, and detects binding between one or more genes from the first gene classifier and the set of probes; and (c) detecting the expression levels of one or more genes from the second gene classifier: TOX, LEF1, CCR4, POU2AF1, GTSF1, PLS3, MMP12, LCK, and NEDD4L, by contacting the isolated nucleic acids with an additional set of probes that recognizes one or more genes from the second gene classifier, and detects binding between one or more genes from the second gene classifier and the additional set of probes. In some embodiments, the method comprises detecting the expression levels of ITK, STAT5A, and TNFSF11 from the first gene classifier. In some embodiments, the method comprises detecting the expression levels of ITK, IL26, STAT5A, and TNFSF11 from the first gene classifier. In some embodiments, the method comprises detecting the expression levels of FYB, ITK, IL26, STAT5A, and TNFSF11 from the first gene classifier. In some embodiments, the method comprises detecting the expression levels of FYB, ITK, IL26, STAT5A, TRAF3IP3, and TNFSF11 from the first gene classifier. In some embodiments, the method comprises detecting the expression levels of FYB, ITK, IL26, STAT5A, TRAF3IP3, DNM3, and TNFSF11 from the first gene classifier. In some embodiments, the method comprises detecting the expression levels of FYB, ITK, IL26, STAT5A, TRAF3IP3, GNLY, DNM3, and TNFSF11 from the first gene classifier. In some embodiments, the expression level is an elevated gene expression level, compared to a gene expression level of an equivalent gene from a control sample. In some embodiments, the gene expression level of FYB, ITK, IL26, STAT5A, TRAF3IP3, DNM3, TNFSF11, or a combination thereof is elevated. In some embodiments, the expression level is a down-regulated gene expression level, compared to a gene expression level of an equivalent gene from a control sample. In some embodiments, the gene expression level of GNLY is down-regulated. In some embodiments, the set of probes recognizes at least one but no more than eight genes. In some embodiments, the additional set of probes recognizes one but no more than nine genes. In some embodiments, the nucleic acids comprise RNA, DNA, or a combination thereof. In some embodiments, the RNA is mRNA. In some embodiments, the RNA is cell-free circulating RNA. In some embodiments, the cells from the stratum corneum comprise T cells or components of T cells. In some embodiments, the cells from the stratum corneum comprise keratinocytes. In some embodiments, the skin sample does not comprise melanocytes. In some embodiments, the skin sample is obtained by applying an adhesive patch to a skin region of the subject in a manner sufficient to adhere cells to the adhesive patch, and removing the adhesive patch from the skin region in a manner sufficient to retain the adhered cells to the adhesive patch. In some embodiments, the skin sample is obtained by applying a plurality of adhesive patches to a skin region of the subject in a manner sufficient to adhere cells to each of the adhesive patches, and removing each of the adhesive patches from the skin region in a manner sufficient to retain the adhered cells to each of the adhesive patches. In some embodiments, the plurality of adhesive patches comprises at least 4 adhesive patches. In some embodiments, the skin region is a skin lesion region. In some embodiments, the subject is suspected of having cutaneous T cell lymphoma (CTCL). In some embodiments, the subject is suspected of having mycosis fungoides (MF). In some embodiments, the subject is suspected of having Sézary syndrome (SS). In some embodiments, the subject is a human.

Disclosed herein, in certain embodiments, is a method of determining the presence of cutaneous T cell lymphoma (CTCL) in a skin sample, comprising: identifying a subject suspected of having CTCL; isolating nucleic acids from a skin sample obtained from the subject by applying an adhesive patch to a skin region of the subject in a manner sufficient to adhere skin sample cells to the adhesive patch, and removing the adhesive patch from the skin sample in a manner sufficient to retain the adhered skin sample cells to the adhesive patch, wherein the skin sample cells comprise cells from the stratum corneum; and detecting an expression level of at least one target gene known to be upregulated or downregulated in subjects with CTCL, by contacting the isolated nucleic acids with a set of probes that recognize the target gene, and detecting binding between the at least one target gene and the set of probes. In some embodiments, the nucleic acids comprise mRNA. In some embodiments, the cells from the stratum corneum comprise T cells or components of T cells. In some embodiments, the cells from the stratum corneum comprise keratinocytes. In some embodiments, the skin sample does not comprise melanocytes. In some embodiments, the skin sample is obtained by applying a plurality of adhesive patches to the skin region of the subject in a manner sufficient to adhere skin sample cells to each of the adhesive patches, and removing each of the plurality of adhesive patches from the skin region in a manner sufficient to retain the adhered skin sample cells to each of the adhesive patches. In some embodiments, the skin region comprises a skin lesion. Some embodiments include determining whether the subject has CTCL based on the expression level of the at least one target gene. Some embodiments include administering a CTCL treatment to the subject based on the determination of whether the subject has CTCL. In some embodiments, the CTCL treatment comprises a steroid, interferon, chemotherapy, phototherapy, radiation therapy, or a bone marrow transplant. In some embodiments, the subject has CTCL. In some embodiments, the CTCL comprises mycosis fungoides. In some embodiments, the CTCL comprises Sézary syndrome. In some embodiments, the subject is a human. In some embodiments, the expression level is upregulated compared to a gene expression level of an equivalent gene from a control sample. In some embodiments, the expression level is down-regulated compared to a gene expression level of an equivalent gene from a control sample. In some embodiments, the at least one target gene comprises a gene encoding an adapter protein, a gene encoding a tyrosine kinase, a gene encoding an interleukin, a gene encoding a transcription factor, a gene encoding a TNF receptor associated factor protein, a gene encoding a TNF, a gene encoding a TNF superfamily member, a gene encoding a saposin-like protein, a gene encoding a GTP-binding protein, a gene encoding a chromatin associated protein, a gene encoding a G-protein-coupled receptor, a gene encoding a transcriptional coactivator, a gene encoding a spermatogenesis protein, a gene encoding an actin-binding protein, a gene encoding a matrix metalloproteinase, a gene encoding a FYN-binding protein family member, a gene encoding a TEC kinase family member, a gene encoding a STAT, a gene encoding a TRAF3 interacting protein, a gene encoding a dynamin family member, a gene encoding a ubiquitin ligase, a gene encoding a thymocyte selection associated high mobility group box family member, a gene encoding a lymphoid enhancer binding factor family member, a gene encoding a C-C chemokine receptor type family member, a gene encoding an Oct binding factor family member, a gene encoding an gametocyte-specific family member, a gene encoding a plastin family member, a gene encoding a lymphocyte-specific protein tyrosine kinase family member, a gene encoding a member of the NEDD4 family of E3 HECT domain ubiquitin ligases, a gene encoding a C-C motif chemokine ligand family member, a gene encoding a chemokine, or a gene encoding a CXC chemokine, or a combination thereof. In some embodiments, the at least one target gene comprises a gene encoding a saposin-like protein, a gene encoding a FYN-binding protein family member, a gene encoding a TEC kinase family member, a gene encoding a STAT, a gene encoding a TRAF3 interacting protein, a gene encoding a CXC chemokine family member, or a combination thereof. In some embodiments, the at least one target gene comprises a gene encoding modulator of cell death, a gene encoding an antimicrobial, a gene encoding a cytokine, or a gene encoding a DNA-binding protein, or a combination thereof. In some embodiments, the at least one target gene comprises FYB, GNLY, ITK, STAT5, TRAF3IP3, CXCL10, CXCL8, and/or TNF, or a combination thereof. In some embodiments, the at least one target gene comprises a gene encoding a microRNA. In some embodiments, the microRNA comprises miR-21, miR-29b, miR-155, miR-186, miR-214, or miR-221. Some embodiments further comprise detecting the presence at least one genotype of one more additional target genes known to be mutated in subjects with CTCL, in the nucleic acids or in a separate set of nucleic acids isolated from the skin sample. In some embodiments, the nucleic acids or the separate set of nucleic acids comprise DNA. In some embodiments, determining whether the subject has CTCL further comprises determining whether the subject has CTCL based on the presence of the at least one genotype. In some embodiments, the one or more additional target genes comprise TP53, ZEB1, ARID1A, DNMT3A, CDKN2A, FAS, STAT5B, PRKCQ, RHOA, DNMT3A, PLCG1, or NFKB2.

Disclosed herein, in certain embodiments, is a method of treating a subject with cutaneous T cell lymphoma (CTCL), comprising: identifying a subject suspected of having CTCL; isolating nucleic acids from a skin sample obtained from the subject by applying an adhesive patch to a skin region of the subject in a manner sufficient to adhere skin sample cells to the adhesive patch, and removing the adhesive patch from the skin sample in a manner sufficient to retain the adhered skin sample cells to the adhesive patch, wherein the skin sample cells comprise cells from the stratum corneum; detecting an expression level of at least one target gene known to be upregulated or downregulated in subjects with CTCL, by contacting the isolated nucleic acids with a set of probes that recognize the target gene, and detecting binding between the at least one target gene and the set of probes; determining whether the subject has CTCL based on the expression level of the at least one target gene; and administering a CTCL treatment to the subject when the subject is determined to have CTCL based on the expression level of the at least one target gene, and not administering the CTCL treatment to the subject when the subject is not determined to have CTCL based on the expression level of the at least one target gene. In some embodiments, the nucleic acids comprise mRNA. In some embodiments, the cells from the stratum corneum comprise T cells or components of T cells. In some embodiments, the cells from the stratum corneum comprise keratinocytes. In some embodiments, the skin sample does not comprise melanocytes. In some embodiments, the skin sample is obtained by applying a plurality of adhesive patches to the skin region of the subject in a manner sufficient to adhere skin sample cells to each of the adhesive patches, and removing each of the plurality of adhesive patches from the skin region in a manner sufficient to retain the adhered skin sample cells to each of the adhesive patches. In some embodiments, the skin region comprises a skin lesion. Some embodiments include determining that the subject has CTCL based on the expression level of the at least one target gene. Some embodiments include administering a CTCL treatment to the subject based on the determination of whether the subject has CTCL. In some embodiments, the CTCL treatment comprises a steroid, interferon, chemotherapy, phototherapy, radiation therapy, or a bone marrow transplant. In some embodiments, the skin sample comprises a CTCL skin lesion. In some embodiments, the CTCL comprises mycosis fungoides. In some embodiments, the CTCL comprises Sézary syndrome. In some embodiments, the subject is a human. In some embodiments, the expression level is upregulated compared to a gene expression level of an equivalent gene from a control sample. In some embodiments, the expression level is downregulated compared to a gene expression level of an equivalent gene from a control sample. In some embodiments, the at least one target gene comprises a gene encoding an adapter protein, a gene encoding a tyrosine kinase, a gene encoding an interleukin, a gene encoding a transcription factor, a gene encoding a TNF receptor associated factor protein, a gene encoding a TNF, a gene encoding a TNF superfamily member, a gene encoding a saposin-like protein, a gene encoding a GTP-binding protein, a gene encoding a chromatin associated protein, a gene encoding a G-protein-coupled receptor, a gene encoding a transcriptional coactivator, a gene encoding a spermatogenesis protein, a gene encoding an actin-binding protein, a gene encoding a matrix metalloproteinase, a gene encoding a FYN-binding protein family member, a gene encoding a TEC kinase family member, a gene encoding a STAT, a gene encoding a TRAF3 interacting protein, a gene encoding a dynamin family member, a gene encoding a ubiquitin ligase, a gene encoding a thymocyte selection associated high mobility group box family member, a gene encoding a lymphoid enhancer binding factor family member, a gene encoding a C-C chemokine receptor type family member, a gene encoding an Oct binding factor family member, a gene encoding an gametocyte-specific family member, a gene encoding a plastin family member, a gene encoding a lymphocyte-specific protein tyrosine kinase family member, a gene encoding a member of the NEDD4 family of E3 HECT domain ubiquitin ligases, a gene encoding a C-C motif chemokine ligand family member, a gene encoding a chemokine, or a gene encoding a CXC chemokine, or a combination thereof. In some embodiments, the at least one target gene comprises a gene encoding a saposin-like protein, a gene encoding a FYN-binding protein family member, a gene encoding a TEC kinase family member, a gene encoding a STAT, a gene encoding a TRAF3 interacting protein, a gene encoding a CXC chemokine family member, or a combination thereof. In some embodiments, the at least one target gene comprises FYN binding protein (FYB), IL2 inducible T-cell kinase (ITK), interleukin 26 (IL26), signal transducer and activator of transcription 5A (STAT5A), TRAF3 interacting protein 3 (TRAF3IP3), granulysin (GNLY), dynamin 3 (DNM3), or tumor necrosis factor superfamily member 11 (TNFSF11), or a combination thereof. In some embodiments, the at least one target gene comprises TOX, LEF1, CCR4, POU2AF1, GTSF1, PLS3, WP12, LCK, or NEDD4L, or a combination thereof. In some embodiments, the at least one target gene comprises FYB, GNLY, ITK, STAT5, TRAF3IP3, CXCL10, CXCL8, or TNF, or a combination thereof. In some embodiments, the at least one target gene comprises a gene encoding a microRNA. In some embodiments, the microRNA comprises miR-21, miR-29b, miR-155, miR-186, miR-214, or miR-221. Some embodiments include detecting the presence at least one genotype of one more additional target genes known to be mutated in subjects with CTCL, in the nucleic acids or in a separate set of nucleic acids isolated from the skin sample. In some embodiments, the nucleic acids or the separate set of nucleic acids comprise DNA. In some embodiments, determining whether the subject has CTCL further comprises determining whether the subject has CTCL based on the presence of the at least one genotype. In some embodiments, the one or more additional target genes comprise TP53, ZEB1, ARID1A, DNMT3A, CDKN2A, FAS, STAT5B, PRKCQ, RHOA, DNMT3A, PLCG1, or NFKB2.

Disclosed herein, in certain embodiments, is a kit for determining the presence of cutaneous T cell lymphoma (CTCL) in a skin sample, comprising: an adhesive patch comprising an adhesive matrix configured to adhere skin sample cells from the stratum corneum of a subject; a nucleic acid isolation reagent; and a plurality of probes that recognize at least one target gene known to be upregulated or downregulated in subjects with CTCL.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1 illustrates exemplary gene biomarkers obtained from skin samples and tested for use as a diagnostic marker. The 'V' denotes genes displaying differential expression between CTCL, tumor and normal skin samples, in FFPE tissues from biopsies, as reported in the respective study shown in the top row of the Figure (left to right: Litvinov, I. V., et al. *Oncoimmunology* (2017) Mar. 17; 6(5): e136618. Dulmage, B. O. and Geskin, L. J. Br. J. *Dermatol.* (2013) Dec. 169(6):1188-97. Litvinov, I. V., et al. *Cancer Med.* (2015) Sep.; 4(9):1440-7. Booken, N., et al. *Leukemia* (2008) Feb.; 22(2):393-9. Shin, J., et. al. *Blood* (2007) Oct. 15;110(8):3015-27).

FIG. 7A is chart including gene expression data from lesional and non-lesional skin.

FIG. 7B is chart including gene expression data from lesional and non-lesional skin.

FIG. 8A is a chart depicting information about some genes.

FIG. 8B is a chart depicting information about some genes.

DETAILED DESCRIPTION OF THE DISCLOSURE

Figure 2:
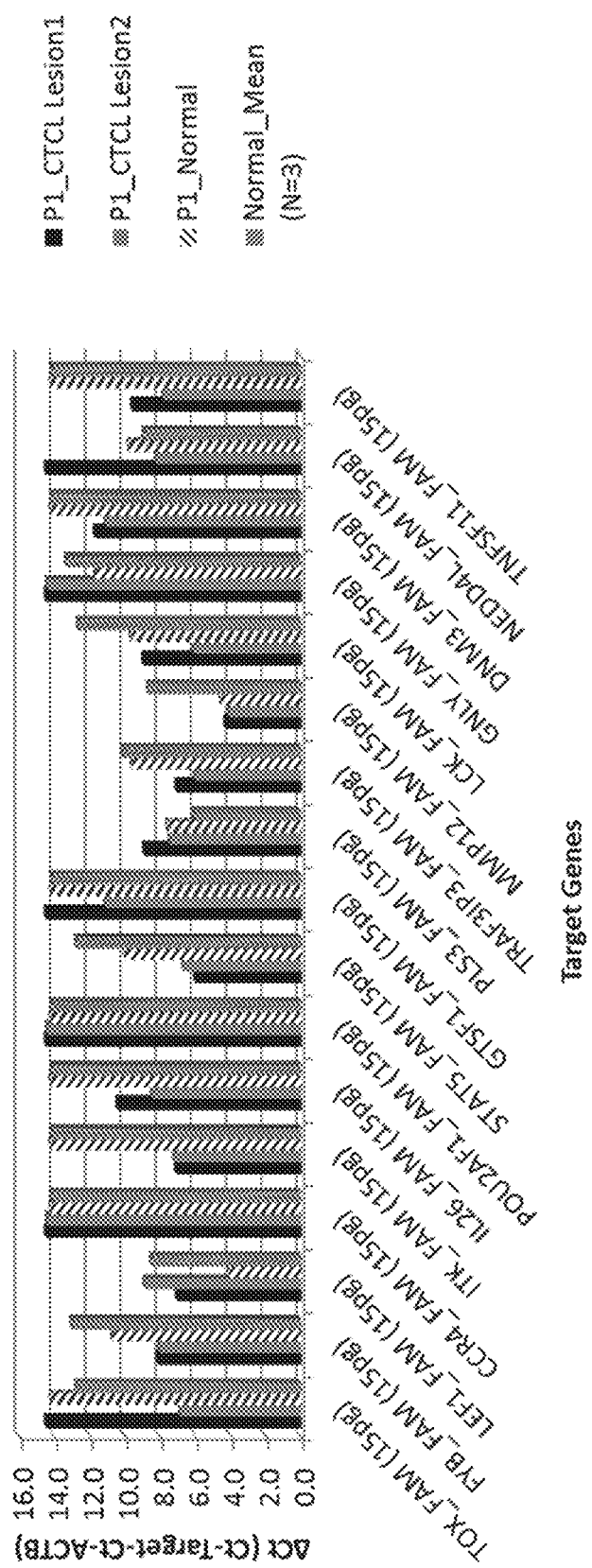
FIG. 2 shows the expression results of 17 exemplary genes tested in lesional, non-lesional, and healthy unaffected control skin samples obtained non-invasively via adhesive patches.

Non-melanoma skin cancer (NMSC) is the most common type of skin cancer and encompasses a collection of skin cancers including angiosarcoma, basal cell carcinoma (BCC), cutaneous B-cell lymphoma, cutaneous T-cell lymphoma (CTCL), dermatofibrosarcoma protuberans, Merkel cell carcinoma, sebaceous carcinoma, and squamous cell carcinoma of the skin (SCC). Cutaneous T-cell lymphoma (CTCL) is a class of non-Hodgkin lymphoma due to altered T cells. In general, the annual incidence of CTCL is about 0.5 per 100,000 in the population and can be observed in adults with a median age of 55-60 years. Further, there are about 7 clinical stages for CTCL (IA, IB, IIA, IIB, III, IVA, and IVB).

CTCL further comprises several subtypes including, but not limited to, mycosis fungoides (MF), Sézary syndrome (SS), pagetoid reticulosis, granulomatous slack skin, lymphomatoid papulosis, *pityriasis* lichenoides chronica, *pityriasis* lichenoides et varioliformis *acuta*, CD30+ cutaneous T-cell lymphoma, secondary cutaneous CD30+ large cell lymphoma, non-mycosis fungoides CD30− cutaneous large T-cell lymphoma, pleomorphic T-cell lymphoma, Lennert lymphoma, subcutaneous T-cell lymphoma, angiocentric lymphoma, and blastic NK-cell lymphoma. Mycosis fungoides (MF) is the most common type of CTCL and the disease phenotype can vary among patients. Sézary syndrome (SS) is an advanced and aggressive subtype of CTCL and is characterized by the presence of malignant lymphoma cells in the blood.

Heterogeneity is observed in the molecular changes (or dysregulated gene expression) between CTCL patients and in some instances within the same patient overtime. In some cases, this heterogeneity is attributed to the different causes which convert normal T cells into malignant T cells. In additional cases, this heterogeneity contributes to the difficulties in detecting the presence of CTCL and in diagnosing a subject in having CTCL.

In some embodiments, disclosed herein is a method of utilizing the expression level of genes in a gene classifier to determine the presence of CTCL. In some cases, the method comprises determining a change in the expression level of genes in a gene classifier, in which the change is compared to a gene expression level of an equivalent gene from a normal sample. In additional embodiments, disclosed herein is a method of determining whether a subject has CTCL based on the expression level of genes in a gene classifier. Some embodiments include the use of a genotype in determining the presence of the CTCL.

Disclosed herein, in some embodiments, are methods of determining the presence of cutaneous T cell lymphoma (CTCL) in a skin sample, comprising: identifying a subject suspected of having CTCL; isolating nucleic acids from a skin sample obtained from the subject by applying an adhesive patch to a skin region of the subject in a manner sufficient to adhere skin sample cells to the adhesive patch, and removing the adhesive patch from the skin sample in a manner sufficient to retain the adhered skin sample cells to the adhesive patch, wherein the skin sample cells comprise cells from the stratum corneum; and detecting an expression level of at least one target gene known to be upregulated or downregulated in subjects with CTCL, by contacting the isolated nucleic acids with a set of probes that recognize the target gene, and detecting binding between the at least one target gene and the set of probes. Some embodiments include the use of a genotype in determining the presence of the CTCL.

Disclosed herein, in some embodiments, are methods of treating a subject with cutaneous T cell lymphoma (CTCL), comprising: identifying a subject suspected of having CTCL; isolating nucleic acids from a skin sample obtained from the subject by applying an adhesive patch to a skin region of the subject in a manner sufficient to adhere skin sample cells to the adhesive patch, and removing the adhesive patch from the skin sample in a manner sufficient to retain the adhered skin sample cells to the adhesive patch, wherein the skin sample cells comprise cells from the stratum corneum; detecting an expression level of at least one target gene known to be upregulated or downregulated in subjects with CTCL, by contacting the isolated nucleic acids with a set of probes that recognize the target gene, and detecting binding between the at least one target gene and the set of probes; determining whether the subject has CTCL based on the expression level of the at least one target gene;

and administering a CTCL treatment to the subject when the subject is determined to have CTCL based on the expression level of the at least one target gene, and not administering the CTCL treatment to the subject when the subject is not determined to have CTCL based on the expression level of the at least one target gene. Some embodiments include the use of a genotype in determining the presence of the CTCL.

Disclosed herein, in some embodiments, are kits for determining the presence of cutaneous T cell lymphoma (CTCL) in a skin sample, comprising: an adhesive patch comprising an adhesive matrix configured to adhere skin sample cells from the stratum corneum of a subject; a nucleic acid isolation reagent; and a plurality of probes. In some embodiments, the probes recognize at least one target gene known to be upregulated or downregulated in subjects with CTCL. In some embodiments, the probes recognize a genotype of at least one target gene known to be mutated in subjects with CTCL.

The kits and methods disclosed herein have several advantages over the prior art. An advantage of using target genes for identifying subjects with skin cancer such as CTCL, or for determining the presence of a skin cancer such as CTCL in a skin sample, is the relatively low cost of obtaining genetic data such as information about gene expression or genotypes. An advantage of using an adhesive tape to collect a skin sample is its non-invasiveness.

In some cases, gene expression data, such as measured amounts of mRNA of one or more target genes, are indicative of a skin cancer such as CTCL. Because mRNA levels do not always correlate with protein levels for a given gene, an existing method that measures protein levels would not render obvious the methods described herein. The usefulness of expression levels of the various genes and type of genes described herein is unexpected in light of such methods because of the unpredictability of whether mRNA levels and protein levels will always align. For example, in one instance a mRNA expression level for a gene may be increased in a CTCL skin lesion compared to a control sample while the protein level of the gene may be unchanged; or vice versa, a protein level may be increased or decreased in a CTCL skin lesion while an mRNA level for the same gene as the protein is unchanged.

Target Genes, Gene Classifiers, and Methods of Use

Disclosed herein, in some embodiments, are methods that include measuring, detecting, or using a target gene. For example, some embodiments relate to a method of determining the presence of a skin cancer such as a cutaneous T cell lymphoma (CTCL) based on a presence or expression level of the target gene, and/or based on a mutation in the target gene. Some embodiments relate to a method of identifying a subject with the skin cancer (e.g. CTCL) based on a presence or expression level of the target gene, and/or based on a mutation in the target gene. Some embodiments include determining the presence of the skin cancer (e.g. CTCL) based on a presence or expression level of the target gene. Some embodiments include determining the presence of the skin cancer (e.g. CTCL) based on a mutation in the target gene. Some embodiments include the use of multiple target genes. Some embodiments include a target gene described in FIGS. 8A-8B. In some embodiments, the target genes described herein are used in any method described herein.

In some embodiments, the target gene encodes an adapter protein. In some embodiments, the adapter protein is a cytosolic adapter protein. In some embodiments, the adapter protein acts as an adapter protein in a signaling cascade such as a FYN and/or LCP2 signaling cascade. In some embodiments, the adapter protein is expressed by platelets, T cells, natural killer cells, myeloid cells, and/or dendritic cells. In some embodiments, the adapter protein is involved in cell motility, proliferation, activation, and cytokine production. A non-limiting example of such an adapter protein is the protein encoded by FYB. Some embodiments include measuring or detecting the presence or an amount of an mRNA encoding one or more adaptor proteins.

In some embodiments, the adapter protein is a FYN-binding protein family member. In some embodiments, the target gene encodes a FYN-binding protein family member. In some embodiments, the FYN-binding protein family member is FYB. Some embodiments include measuring or detecting the presence or an amount of mRNA encoding one or more FYN-binding protein family members.

In some embodiments, the target gene encodes an enzyme. In some embodiments, the enzyme is a kinase. In some embodiments, the target gene encodes a kinase. In some embodiments, the kinase is a tyrosine kinase. In some embodiments, the target gene encodes a tyrosine kinase. Examples of tyrosine kinases include but are not limited to proteins encoded by ITK and LCK. Some embodiments include multiple genes encoding tyrosine kinases as target genes. In some embodiments, the tyrosine kinases include ITK and LCK. Some embodiments include measuring or detecting the presence or an amount of an mRNA encoding one or more tyrosine kinase.

In some embodiments, the tyrosine kinase is an intracellular tyrosine kinase. In some embodiments, the tyrosine kinase is thought to play a role in T-cell proliferation and differentiation. In some embodiments, the tyrosine kinase is expressed in T-cells. A non-limiting example of such a tyrosine kinase is the protein encoded by ITC.

In some embodiments, the tyrosine kinase is a member of the TEC family of kinases. In some embodiments, the target gene encodes a TEC kinase family member. In some embodiments, the TEC family member is the protein encoded by ITC. Some embodiments include measuring or detecting the presence or an amount of mRNA encoding one or more TEC kinase family members.

In some embodiments, the tyrosine kinase is a lymphocyte-specific protein tyrosine kinase family member. In some embodiments, the target gene encodes a lymphocyte-specific protein tyrosine kinase family member. In some embodiments, the lymphocyte-specific protein tyrosine kinase family member is a non-receptor tyrosine kinase. In some embodiments, the lymphocyte-specific protein tyrosine kinase family member is a member of the Src family of protein tyrosine kinases. In some embodiments, the lymphocyte-specific protein tyrosine kinase family member is expressed in T cells. In some embodiments, the lymphocyte-specific protein tyrosine kinase family member is anchored to a plasma membrane. In some embodiments, the lymphocyte-specific protein tyrosine kinase family member associates with cytoplasmic tails of CD4 or CD8 co-receptors. In some embodiments, the lymphocyte-specific protein tyrosine kinase family member phosphorylates an intracellular chain of CD3 or a ζ-chains of a TCR complex. In some embodiments, the lymphocyte-specific protein tyrosine kinase family member phosphorylates ZAP-70. In some embodiments, upon T cell activation, the lymphocyte-specific protein tyrosine kinase family member translocates from outside a lipid raft to inside the lipid raft and activates Fyn. A non-limiting example of such a lymphocyte-specific protein tyrosine kinase family member is the protein encoded by LCK. Some embodiments include measuring or detecting the presence or an amount of mRNA encoding one or more lymphocyte-specific protein tyrosine kinase family members.

In some embodiments, the enzyme is a matrix metalloproteinase. In some embodiments, the target gene encodes a matrix metalloproteinase. In some embodiments, the matrix metalloproteinase a member of the peptidase M10 family of matrix metalloproteinases. In some embodiments, the matrix metalloproteinase is involved in the breakdown of an extracellular matrix. A non-limiting example of such a matrix metalloproteinase is the protein encoded by WP12. Some embodiments include measuring or detecting the presence or an amount of mRNA encoding one or more matrix metalloproteinases.

In some embodiments, the enzyme is a ubiquitin ligase. In some embodiments, the target gene encodes a ubiquitin ligase. In some embodiments, the ubiquitin ligase is an E3 ubiquitin ligase. In some embodiments, the ubiquitin ligase comprises a HECT domain. In some embodiments, the ubiquitin ligase is a member of the Nedd4 family of HECT domain E3 ubiquitin ligases. In some embodiments, the ubiquitin ligase ubiquitinates an epithelial sodium channel, a Na+-Cl-co-transporter, or a voltage gated sodium channel. In some embodiments, the ubiquitin ligase comprises a Ca2+-phospholipid binding domain. In some embodiments, the ubiquitin ligase comprises a WW protein-protein interaction domain. A non-limiting example of such a ubiquitin ligase is the protein encoded by NEDD4L. Some embodiments include measuring or detecting the presence or an amount of mRNA encoding one or more ubiquitin ligases as described herein.

In some embodiments, the ubiquitin ligase is a member of the NEDD4 family of E3 HECT domain ubiquitin ligases. In some embodiments, the target gene encodes a member of the NEDD4 family of E3 HECT domain ubiquitin ligases. In some embodiments, the member of the NEDD4 family of E3 HECT domain ubiquitin ligases is NEDD4L. Some embodiments include measuring or detecting the presence or an amount of mRNA encoding one or more members of the NEDD4 family of E3 HECT domain ubiquitin ligases.

In some embodiments, the enzyme is a guanosine triphosphate (GTP)-binding protein. In some embodiments, the target gene encodes a GTP-binding protein. In some embodiments, the GTP-binding protein is a GTPase. In some embodiments, the GTP-binding protein is involved in actin-membrane an process such as membrane budding. In some embodiments, the GTP-binding protein associates with microtubules. In some embodiments, the GTP-binding protein is involved in vesicular transport. A non-limiting example of such a GTP-binding protein is the protein encoded by DNM3. Some embodiments include measuring or detecting the presence or an amount of mRNA encoding one or more GTP-binding proteins.

In some embodiments, the GTP-binding protein is a dynamin. In some embodiments, the target gene encodes a dynamin. In some embodiments, the dynamin is DNM3. Some embodiments include measuring or detecting the presence or an amount of mRNA encoding one or more dynamins.

In some embodiments, the target gene encodes a member of a TNF receptor associated factor protein family. In some embodiments, the TNF receptor associated factor protein family member is TRAF3IP3. Some embodiments include measuring or detecting the presence or an amount of mRNA encoding one or more TNF receptor associated factor proteins.

In some embodiments, the member of a TNF receptor associated factor protein family is a TRAF3 interacting protein. In some embodiments, the target gene encodes a TRAF3 interacting protein. In some embodiments, the TRAF3 interacting protein mediates growth. In some embodiments, the TRAF3 interacting protein modulates the c-Jun N-terminal kinase signal transduction pathway. In some embodiments, the TRAF3 interacting protein interacts with a multi-protein assembly containing a phosphatase 2A catalytic subunit. A non-limiting example of such a TRAF3 interacting protein is the protein encoded by TRAF3IP3. Some embodiments include measuring or detecting the presence or an amount of mRNA encoding one or more TRAF3 interacting proteins.

In some embodiments, the target gene encodes a cytokine. Examples of cytokines include but are not limited to proteins encoded by TNFSF11, IL26, CCL27, CXCL8, CXCL9, CXCL10, and TNF. Examples of cytokines include but are not limited to chemokines and interleukins. Some embodiments include multiple genes encoding cytokines as target genes. In some embodiments, the cytokines include TNFSF11. In some embodiments, the cytokines include IL26. In some embodiments, the cytokines include CCL27. In some embodiments, the cytokines include CXCL8. In some embodiments, the cytokines include CXCL9. In some embodiments, the cytokines include CXCL10. In some embodiments, the cytokines include TNF. In some embodiments, the cytokines include 1, 2, 3, 4, 5, 6, or 7, or a range defined by any of the aforementioned integers, of TNFSF11, IL26, CCL27, CXCL8, CXCL9, CXCL10, or TNF. Some embodiments include measuring or detecting the presence or an amount of an mRNA encoding one or more cytokines.

In some embodiments, the cytokine is a TNF superfamily member. In some embodiments, the target gene encodes a TNF superfamily member. In some embodiments, the TNF superfamily member is involved in inflammation. In some embodiments, the TNF superfamily member is part of an acute phase inflammatory reaction. In some embodiments, the TNF superfamily member comprises a TNF domain. In some embodiments, the TNF superfamily member is a pyrogen. In some embodiments, the TNF superfamily member induces apoptosis. In some embodiments, the TNF superfamily member is secreted by a macrophage. In some embodiments, the TNF superfamily member binds TNFRSF1A/TNFR1 and/or TNFRSF1B/TNFBR. A non-limiting example of such a TNF superfamily member is TNFα, the protein encoded by TNF. In some embodiments, the cytokine is TNFα (encoded by TNF). Some embodiments include measuring or detecting the presence or an amount of mRNA encoding one or more TNF superfamily members.

In some embodiments, the cytokine is a modulator of cell death. In some embodiments, the cell death comprises or consists of apoptosis In some embodiments, the target gene encodes a modulator of cell death. Examples of cell death modulators include but are not limited to proteins encoded by IL26, GNLY, TNFSF11, and TNF. In some embodiments, the modulator of cell death is encoded by IL26. In some embodiments, the modulator of cell death is encoded by GNLY. In some embodiments, the modulator of cell death is encoded by TNFSF11. In some embodiments, the modulator of cell death is encoded by TNF. Some embodiments include multiple genes encoding modulators of cell death as target genes. In some embodiments, the modulators of cell death include proteins encoded by IL26 and GNLY. In some embodiments, the modulators of cell death include proteins encoded by GNLY and TNFSF11. In some embodiments, the modulators of cell death include proteins encoded by IL26 and TNFSF11. In some embodiments, the modulators of cell death include proteins encoded by IL26, GNLY, and TNFSF11. In some embodiments, the modulators of cell death include proteins encoded by TNF, IL26 and GNLY. In some embodiments, the modulators of cell death include proteins encoded by TNF, GNLY and TNFSF11. In some embodiments, the modulators of cell death include proteins encoded by TNF, IL26 and TNFSF11. In some embodiments, the modulators of cell death include proteins encoded by TNF, IL26, GNLY, and TNFSF11. Some embodiments include measuring or detecting the presence or an amount of an mRNA encoding one or more modulators of cell death as described herein.

In some embodiments, the cytokine is a chemokine. In some embodiments, the target gene encodes a chemokine. Examples of chemokines include but are not limited to proteins encoded by CCL27, CXCL8, CXCL9, and CXCL10. Some embodiments include multiple genes encoding chemokines as target genes. In some embodiments, the chemokines include CCL27 and CXCL8. In some embodiments, the chemokines include CCL27 and CXCL9. In some embodiments, the chemokines include CCL27 and CXCL10. In some embodiments, the chemokines include CXCL8, CXCL9, and CXCL10. In some embodiments, the chemokines include CCL27, CXCL8, and CXCL9. In some embodiments, the chemokines include CCL27, CXCL8, and CXCL10. In some embodiments, the chemokines include CCL27, CXCL9, and CXCL10. In some embodiments, the chemokines include CCL27, CXCL8, CXCL9, and CXCL10. In some embodiments, the chemokines include CXCL8 and CXCL9. In some embodiments, the chemokines include CXCL8 and CXCL10. In some embodiments, the chemokines include CXCL9 and CXCL10. Some embodiments include measuring or detecting the presence or an amount of an mRNA encoding one or more chemokines.

In some embodiments, the chemokine is a C-C motif chemokine ligand family member. In some embodiments, the target gene encodes a C-C motif chemokine ligand family member. Some embodiments include measuring or detecting the presence or an amount of mRNA encoding one or more C-C motif chemokine ligand family members. In some embodiments, the C-C motif chemokine ligand family member is CCL27.

In some embodiments, the C-C motif chemokine ligand family member is a CC cytokine. In some embodiments, the target gene encodes a CC cytokine. In some embodiments, the CC cytokine is clustered on the p-arm of chromosome 9. In some embodiments, the CC chemokine is secreted. In some embodiments, the CC cytokine is involved in an immunoregulatory or inflammatory process. In some embodiments, the CC cytokine comprises two adjacent cysteines. In some embodiments, the CC cytokine is chemotactic for skin-associated memory T lymphocytes. In some embodiments, the CC cytokine is associated with homing of memory T lymphocytes to the skin. In some embodiments, the CC cytokine plays a role in skin inflammation. In some embodiments, the CC cytokine binds a chemokine receptor such as CCR10. A non-limiting example of such a CC cytokine is the protein encoded by CCL27. Some embodiments include measuring or detecting the presence or an amount of mRNA encoding one or more CC cytokines.

In some embodiments, the chemokine is a CXC chemokine. In some embodiments, the target gene encodes a CXC chemokine. Examples of CXC chemokines include but are not limited to proteins encoded by CXCL8, CXCL9, and CXCL10. Some embodiments include multiple genes encoding CXC chemokines as target genes. In some embodiments, the CXC chemokines include CXCL8 and CXCL9. In some embodiments, the CXC chemokines include CXCL8 and CXCL10. In some embodiments, the CXC chemokines include CXCL9 and CXCL10. In some embodiments, the CXC chemokines include CXCL8, CXCL9, and CXCL10. Some embodiments include measuring or detecting the presence or an amount of an mRNA encoding one or more CXC chemokines.

In some embodiments, the CXC chemokine is produced by a macrophage. In some embodiments, the CXC chemokine is produced by an epithelial cell, airway smooth muscle cell, or an endothelial cell. In some embodiments, the CXC chemokine is stored in a storage vesicle such as a Weibel-Palade body by a cell such as an endothelial cell. In some embodiments, the CXC chemokine is initially produced as a precursor peptide which undergoes cleavage. In some embodiments, the CXC chemokine binds heparin. In some embodiments, the CXC chemokine binds by a receptor such as a GPCR, or a serpentine receptor such as CXCR1 or CXCR2. In some embodiments, the CXC chemokine is secreted. In some embodiments, the CXC chemokine mediates an immune reaction such as an innate immune reaction. In some embodiments, the CXC chemokine mediates activation of a neutrophil. In some embodiments, the CXC chemokine mediates migration of neutrophils into tissue from peripheral blood. A non-limiting example of such a CXC chemokine is the protein encoded by CXCL8.

In some embodiments, the CXC chemokine is a monokine induced by gamma interferon. In some embodiments, the CXC chemokine plays a role in chemotaxis. In some embodiments, the CXC chemokine promotes differentiation or multiplication of a leukocyte. In some embodiments, the CXC chemokine causes tissue extravasion. In some embodiments, the CXC chemokine mediates lymphocytic infiltration to the focal sites. In some embodiments, the CXC chemokine suppresses tumor growth. In some embodiments, the CXC chemokine interacts with CXCR3. In some embodiments, the CXC chemokine elicits a chemotactic function by interacting with CXCR3. In some embodiments, the CXC chemokine is involved in T cell trafficking. In some embodiments, the CXC chemokine is an antimicrobial. In some embodiments, the CXC chemokine is a chemoattractant for lymphocytes. In some embodiments, the CXC chemokine is not a chemoattractant for neutrophils. A non-limiting example of such a CXC chemokine is the protein encoded by CXCL9.

In some embodiments, the CXC chemokine is a chemoattractant. In some embodiments, the CXC chemokine is an antimicrobial. In some embodiments, the CXC chemokine interacts with CXCR3. In some embodiments, the CXC chemokine elicits a chemotactic function by interacting with CXCR3. A non-limiting example of such a CXC chemokine is the protein encoded by CXCL10. Some embodiments include measuring or detecting the presence or an amount of mRNA encoding one or more CXC chemokines.

In some embodiments, the cytokine is an interleukin. In some embodiments, the target gene encodes an interleukin. Examples of interleukins include but are not limited to proteins encoded by IL26 and CXCL8. Some embodiments include multiple genes encoding interleukins as target genes. In some embodiments, the interleukins include IL26 and CXCL8.

In some embodiments, the interleukin is expressed in a T cell such as a herpesvirus-transformed T cell. In some embodiments, the interleukin is a TH17-cell derived interleukin. In some embodiments, the TH17-cell derived cytokine is IL-26. In some embodiments, the interleukin induces phosphorylation of a transcription factor such as STAT1 or STAT3. In some embodiments, the interleukin enhances the secretion of another interleukin such as IL-10 or IL-8. In some embodiments, the interleukin is an antimicrobial. In some embodiments, the interleukin promotes sensing of bacterial and host cell death. In some embodiments, the interleukin is a cationic amphipathic protein. In some embodiments, the interleukin kills extracellular bacteria by membrane-pore formation. In some embodiments, the interleukin complexes with bacterial DNA or self-DNA released by dying bacterial or host cells. In some embodiments, the interleukin activates a Toll-like receptor such as Toll-like receptor 9. In some embodiments, the interleukin activates an IL-26 receptor. A non-limiting example of such an interleukin is the protein encoded by IL26. Some embodiments include measuring or detecting the presence or an amount of mRNA encoding one or more interleukins.

In some embodiments, the chemokine is an antimicrobial. In some embodiments, the interleukin is an antimicrobial. In some embodiments, the target gene encodes an antimicrobial. Examples of antimicrobials include but are not limited to proteins encoded by IL26 and GNLY. In some embodiments, the antimicrobial has an anti-tumor effect, or is also an anti-tumor protein. Some embodiments include multiple genes encoding antimicrobials as target genes. In some embodiments, the antimicrobials include IL26 and GNLY. Some embodiments include measuring or detecting the presence or an amount of an mRNA encoding one or more antimicrobials.

In some embodiments, the chemokine is an interleukin. In some embodiments, the interleukin is a member of the CXC chemokine family. In some embodiments, the interleukin is CXCL8.

In some embodiments, the interleukin is a member of the IL-10 family of cytokines. In some embodiments, the member of the IL-10 family of cytokines is IL-26.

In some embodiments, the target gene encodes a DNA-binding protein. Examples of genes encoding DNA-binding proteins include but are not limited to IL26, STAT5A, TOX, and LEF1. Some embodiments include multiple genes encoding DNA-binding proteins as target genes. In some embodiments, the DNA-binding proteins include IL26 and STAT5A. In some embodiments, the DNA-binding proteins include IL26 and TOX. In some embodiments, the DNA-binding proteins include IL26 and LEF1. In some embodiments, the DNA-binding proteins include STAT5A and TOX. In some embodiments, the DNA-binding proteins include STAT5A and LEF1. In some embodiments, the DNA-binding proteins include TOX and STAT5A. In some embodiments, the DNA-binding proteins include IL26, STAT5A, and TOX. In some embodiments, the DNA-binding proteins include IL26, STAT5A, and LEF1. In some embodiments, the DNA-binding proteins include IL26, TOX, and LEF1. In some embodiments, the DNA-binding proteins include STAT5A, TOX, and LEF1. In some embodiments, the DNA-binding proteins include IL26, STAT5A, TOX, and LEF1. Some embodiments include measuring or detecting the presence or an amount of an mRNA encoding one or more DNA-binding proteins.

In some embodiments, the DNA-binding protein is a transcription factor. In some embodiments, the target gene encodes a transcription factor. Examples of transcription factors include but are not limited to proteins encoded by STAT5A and LEF1. Some embodiments include multiple genes encoding transcription factors as target genes. In some embodiments, the transcription factors include STAT5A and LEF1. Some embodiments include measuring or detecting the presence or an amount of an mRNA encoding one or more transcription factors.

In some embodiments, the transcription factor is a signal transducer and activator of transcription (STAT) family member. In some embodiments, the target gene encodes a STAT family member. In some embodiments, the STAT family member includes an N-terminal domain, a coiled-coil domain, a DNA binding domain, a linker domain, a Src Homology 2 domain, and/or a transcriptional activation domain. In some embodiments, the STAT family member is phosphorylated by a receptor associated kinase. In some embodiments, the STAT family member forms homo- or heterodimers that translocate to the cell nucleus upon phosphorylation. In some embodiments, the STAT family member mediates the response of a cell ligand such as IL2, IL3, IL7 GM-CSF, erythropoietin, thrombopoietin, or a growth hormone. A non-limiting example of such a STAT family member is the protein encoded by STAT5A. Some embodiments include measuring or detecting the presence or an amount of mRNA encoding one or more STAT family members.

In some embodiments, the transcription factor is a lymphoid enhancer binding factor family member. In some embodiments, the target gene encodes a lymphoid enhancer binding factor family member. In some embodiments, the lymphoid enhancer binding factor family member is a nuclear protein. In some embodiments, the lymphoid enhancer binding factor family member is expressed in pre-B cells and/or in T cells. In some embodiments, the lymphoid enhancer binding factor family member binds to a T-cell receptor-alpha enhancer. In some embodiments, the lymphoid enhancer binding factor family member binding to the T-cell receptor-alpha enhancer increases enhancer activity. In some embodiments, the lymphoid enhancer binding factor family member is a member of a family of regulatory proteins that share homology with high mobility group protein-1. A non-limiting example of such a lymphoid enhancer binding factor family member is the protein encoded by LEF1. Some embodiments include measuring or detecting the presence or an amount of mRNA encoding one or more lymphoid enhancer binding factor family members.

In some embodiments, the target gene encodes a transcriptional coactivator. In some embodiments, the transcriptional coactivator is expressed in B-cell lymphocytes. In some embodiments, the transcriptional coactivator controls expression of immunoglobulin, CD20, CRISP-3, or CD36. A non-limiting example of such a transcriptional coactivator is the protein encoded by POU2AF1. Some embodiments include measuring or detecting the presence or an amount of mRNA encoding one or more transcriptional coactivators.

In some embodiments, the transcriptional coactivator is a POU domain class 2-associating factor family member. In some embodiments, the target gene encodes a POU domain class 2-associating factor family member. In some embodiments, the POU domain class 2-associating factor family member is an Oct binding factor family member. In some embodiments, the POU domain class 2-associating factor family member is POU2AF1. Some embodiments include measuring or detecting the presence or an amount of mRNA encoding one or more POU domain class 2-associating factor family members.

In some embodiments, the target gene encodes a saposin-like protein family member. In some embodiments, the saposin-like protein family member is present in cytotoxic granules of cytolytic T cells or natural killer (NK) cells and is released from the granules upon antigen stimulation. In some embodiments, the saposin-like protein family member is an antimicrobial. In some embodiments, the saposin-like protein family member induces cell death (e.g. apoptosis) in target cell. A non-limiting example of such a saposin-like protein family member is the protein encoded by GNLY. Some embodiments include measuring or detecting the presence or an amount of mRNA encoding one or more saposin-like protein family members as described herein.

In some embodiments, the target gene encodes a tumor necrosis factor (TNF) superfamily member. In some embodiments, the TNF superfamily member regulates apoptosis. In some embodiments, the TNF superfamily member is a ligand for a receptor such as receptor activator of nuclear factor κ B (RANK) or osteoprotegerin. In some embodiments, the TNF superfamily member controls cell proliferation, for example by modifying protein levels of Id4, Id2 or cyclin D1. In some embodiments, the TNF superfamily member functions as a factor in osteoclast differentiation or activation. In some embodiments, the TNF superfamily member is a cell survival factor. In some embodiments, the TNF superfamily member is involved in the regulation of T cell-dependent immune response. In some embodiments, the TNF superfamily member activates AKT/PKB, for example through a signaling complex involving SRC kinase and tumor necrosis factor receptor-associated factor (TRAF) 6. A non-limiting example of such a TNF superfamily member is the protein encoded by TNFSF11.

In some embodiments, the target gene encodes a chromatin associated protein. In some embodiments, the chromatin associated protein binds DNA in a sequence-specific manner binding protein. In some embodiments, the chromatin associated protein induces a bend in DNA bound by the protein. A non-limiting example of such a chromatin associated protein is the protein encoded by TOX. Some embodiments include measuring or detecting the presence or an amount of mRNA encoding one or more chromatin associated proteins.

In some embodiments, the chromatin associated protein is a thymocyte selection associated high mobility group (HMG) box family member. In some embodiments, the target gene encodes a thymocyte selection associated HMG box family member. In some embodiments, the HMG box family member includes a HMG box DNA binding domain. In some embodiments, the HMG box family member includes multiple HMG box DNA binding domains. In some embodiments, the HMG box family member includes no more than one HMG box DNA binding domain. In some embodiments, the HMG box family member binds DNA in a sequence-independent manner. In some embodiments, the thymocyte selection associated HMG box family member is TOX. Some embodiments include measuring or detecting the presence or an amount of mRNA encoding one or more thymocyte selection associated HMG box family members.

In some embodiments, the target gene encodes a G-protein-coupled receptor (GPCR). In some embodiments, the GPCR is a receptor for a CC chemokine such as MCPCCL2, CCL4, CCL5, CCL17, or CCL22. A non-limiting example of such a GPCR is the protein encoded by CCR4. Some embodiments include measuring or detecting the presence or an amount of mRNA encoding one or more GPCRs.

In some embodiments, the GPCR is a C-C chemokine receptor type family member. In some embodiments, the target gene encodes a C-C chemokine receptor type family member. In some embodiments, the C-C chemokine receptor type family member is CCR4. Some embodiments include measuring or detecting the presence or an amount of mRNA encoding one or more C-C chemokine receptor type family members.

In some embodiments, the target gene encodes a gametocyte-specific family member. In some embodiments, the gametocyte-specific family member is GTSF1. Some embodiments include measuring or detecting the presence or an amount of mRNA encoding one or more gametocyte-specific family members.

In some embodiments, the gametocyte-specific family member is a spermatogenesis protein. In some embodiments, the target gene encodes a spermatogenesis protein. In some embodiments, the spermatogenesis protein is expressed in testes. A non-limiting example of such a spermatogenesis protein is the protein encoded by GTSF1. Some embodiments include measuring or detecting the presence or an amount of mRNA encoding one or more spermatogenesis proteins.

In some embodiments, the target gene encodes an actin-binding protein. A non-limiting example of an actin-binding protein is the protein encoded by PLS3. Some embodiments include measuring or detecting the presence or an amount of mRNA encoding one or more actin-binding proteins.

In some embodiments, the actin-binding protein is a plastin family member. In some embodiments, the target gene encodes a plastin family member. Some embodiments include measuring or detecting the presence or an amount of mRNA encoding one or more plastin family members. In some embodiments, the plastin family member is PLS3.

In some embodiments, the target gene encodes FYN binding protein, and is represented by "FYB." In some embodiments, the target gene encodes lymphoid enhancer binding factor 1, and is represented by "LEF1". In some embodiments, the target gene encodes IL2 inducible T-cell kinase, and is represented by "ITK." In some embodiments, the target gene encodes interleukin 26, and is represented by "IL26." In some embodiments, the target gene encodes signal transducer and activator of transcription 5A, and is represented by "STAT5A." In some embodiments, the target gene encodes TRAF3 interacting protein 3, and is represented by "TRAF3IP3." In some embodiments, the target gene encodes granulysin, and is represented by "GNLY." In some embodiments, the target gene encodes dynamin 3, and is represented by "DNM3." In some embodiments, the target gene encodes tumor necrosis factor superfamily member 11, and is represented by "TNFSF11." In some embodiments, the target gene encodes thymocyte selection associated high mobility group box, and is represented by "TOX" In some embodiments, the target gene encodes C-C motif chemokine receptor 4, and is represented by "CCR4." In some embodiments, the target gene encodes POU class 2 associating factor 1, and is represented by "POU2AF1." In some embodiments, the target gene encodes gametocyte specific factor 1, and is represented by "GTSF1." In some embodiments, the target gene encodes plastin 3, and is represented by "PLS3." In some embodiments, the target gene encodes matrix metallopeptidase 12, and is represented by "MMP12." In some embodiments, the target gene encodes LCK proto-oncogene, Src family tyrosine kinase, and is represented by "LCK." In some embodiments, the target gene encodes Neural precursor cell expressed, developmentally down-regulated, and is represented by "NEDD4L." In some embodiments, the target gene encodes C-C motif chemokine ligand 27, and is represented by "CCL27." In some embodiments, the target gene encodes chemokine (C-X-C motif) ligand 8, and is represented by "CXCL8." CXCL8 may also be referred to as IL8. In some embodiments, the target gene encodes a chemokine such as the protein encoded by CXCL8. In some embodiments, the target gene encodes chemokine (C-X-C motif) ligand 9, and is represented by "CXCL9." In some embodiments, the target gene encodes C-X-C motif chemokine 10, and is represented by "CXCL10." In some embodiments, the target gene encodes tumor necrosis factor, and is represented by "TNF."

In some embodiments, the at least one target gene comprises FYB, GNLY, ITK, STAT5, TRAF3IP3, CXCL10, CXCL8, and/or TNF, or a combination thereof. Some embodiments include measuring, obtaining, or measuring a gene expression level of FYB, GNLY, ITK, STAT5, TRAF3IP3, CXCL10, CXCL8, and/or TNF, or a combination thereof. In some embodiments, the at least one target gene comprises FYB. In some embodiments, the at least one target gene comprises FYB. In some embodiments, the at least one target gene comprises GNLY. In some embodiments, the at least one target gene comprises ITK. In some embodiments, the at least one target gene comprises STAT5. In some embodiments, the at least one target gene comprises TRAF3IP3. In some embodiments, the at least one target gene comprises CXCL10. In some embodiments, the at least one target gene comprises CXCL8. In some embodiments, the at least one target gene comprises TNF. In some embodiments, the at least one target gene one, two, three, four, five, six, seven, or eight of FYB, GNLY, ITK, STAT5, TRAF3IP3, CXCL10, CXCL8, or TNF.

Measuring or determining expression levels of one or more target genes may be useful because some microRNAs are dysregulated in skin cancers such as CTCL. In some embodiments, one or more target genes are used to diagnose, identify, or determine the presence of a CTCL. In some embodiments, one or more target genes are used to rule out a skin cancer other than CTCL.

In some embodiments, the target gene encodes a microRNA. In some embodiments, the microRNA is a small non-coding RNA. In some embodiments, the microRNA comprises or consists of 19-25 nucleotides. In some embodiments, the microRNA is from an intronic, intergenic, or antisense nucleic acid region. In some embodiments, the microRNA regulates post-transcriptional gene expression. Some embodiments described herein, include an RNA comprising a microRNA as described herein. Measuring or determining expression levels of one or more microRNAs may be useful because some microRNAs are dysregulated in skin cancers such as CTCL.

Examples of microRNAs include but are not limited to miR-21, miR-27b, miR-29b, miR-30c, miR-34a, miR-93, miR-141/200c, miR-142, miR-146, miR-148a, miR-152, miR-155, miR-181a/b, miR-186, miR-203, miR-205, miR-214, miR-221, miR-326, miR-486, miR-663b, and miR-711. In some embodiments, the microRNA comprises miR-21, miR-29b, miR-155, miR-186, miR-214, or miR-221. In some embodiments, the microRNA comprises miR-21. In some embodiments, the miR-21 is upregulated in a CTCL skin sample relative to a control. In some embodiments, the microRNA comprises miR-27b. In some embodiments, the miR-27b is upregulated in a CTCL skin sample relative to a control. In some embodiments, the microRNA comprises miR-29b. In some embodiments, the miR-29b is downregulated in a CTCL skin sample relative to a control. In some embodiments, the microRNA comprises miR-30c. In some embodiments, the miR-30c is upregulated in a CTCL skin sample relative to a control. In some embodiments, the microRNA comprises miR-34a. In some embodiments, the miR-34a is upregulated in a CTCL skin sample relative to a control. In some embodiments, the microRNA comprises miR-93. In some embodiments, the miR-93 is upregulated in a CTCL skin sample relative to a control. In some embodiments, the microRNA comprises miR-141/200c. In some embodiments, the miR-141/200c is upregulated in a CTCL skin sample relative to a control. In some embodiments, the microRNA comprises miR-142. In some embodiments, the miR-142 is upregulated in a CTCL skin sample relative to a control. In some embodiments, the microRNA comprises miR-146. In some embodiments, the miR-146 is upregulated in a CTCL skin sample relative to a control. In some embodiments, the microRNA comprises miR-148a. In some embodiments, the miR-148a is upregulated in a CTCL skin sample relative to a control. In some embodiments, the microRNA comprises miR-148b. In some embodiments, the miR-148b is upregulated in a CTCL skin sample relative to a control. In some embodiments, the microRNA comprises miR-152. In some embodiments, the miR-152 is upregulated in a CTCL skin sample relative to a control. In some embodiments, the microRNA comprises miR-155. In some embodiments, the miR-155 is upregulated in a CTCL skin sample relative to a control. In some embodiments, the microRNA comprises miR-181a/b. In some embodiments, the miR-181a/b is upregulated in a CTCL skin sample relative to a control. In some embodiments, the microRNA comprises miR-186. In some embodiments, the miR-186 is upregulated in a CTCL skin sample relative to a control. In some embodiments, the microRNA comprises miR-203. In some embodiments, the miR-203 is downregulated in a CTCL skin sample relative to a control. In some embodiments, the microRNA comprises miR-205. In some embodiments, the miR-205 is downregulated in a CTCL skin sample relative to a control. In some embodiments, the microRNA comprises miR-214. In some embodiments, the miR-214 is upregulated in a CTCL skin sample relative to a control. In some embodiments, the microRNA comprises miR-221. In some embodiments, the miR-221 is upregulated in a CTCL skin sample relative to a control. In some embodiments, the microRNA comprises miR-326. In some embodiments, the miR-326 is upregulated in a CTCL skin sample relative to a control. In some embodiments, the microRNA comprises miR-486. In some embodiments, the miR-486 is upregulated in a CTCL skin sample relative to a control. In some embodiments, the microRNA comprises miR-663b. In some embodiments, the miR-663b is upregulated in a CTCL skin sample relative to a control. In some embodiments, the microRNA comprises miR-711. In some embodiments, the miR-711 is upregulated in a CTCL skin sample relative to a control. Some embodiment include the use of multiple microRNAs as target genes. Some embodiment include the use of 1, 2, 3, 4, 5, 6, 7, 8, 9, 10, 11, 12, 13, 14, 15, or more microRNAs as target genes. Some embodiment include the use of a range of microRNAs as target genes, for example a range defined by any two of 1, 2, 3, 4, 5, 6, 7, 8, 9, 10, 11, 12, 13, 14, or 15.

In some embodiments, an amount of the microRNA is increased in CTCL relative to a non-CTCL control. In some embodiments, an amount of the microRNA is decreased in CTCL relative to a non-CTCL control.

In some embodiments, the microRNA is part of a cytokine or interleukin signaling pathway. For example, IL2 signaling may lead to upregulation of miR-155, miR-21, and miR-214, and/or downregulation of miR-29b. In some embodiments, STAT5 leads to miR-155 upregulation in response to IL2 signaling. In some embodiments, STAT3 leads to miR-21 upregulation in response to IL2 signaling. In some embodiments, CTCL comprises increased IL2 signaling and upregulated miR-155, miR-21, and miR-214, and downregulated miR-29b. MiR-21 may target PTEN. MiR-155 may target FOXO3A. MiR-214 may target PTEN, LHX6, Bcl2, and/or KIF12. MiR-29b may target MMP2, DNMT3, SP-1, and/or BRD4. Any of these microRNA targets may be dysregulated in a skin cancer such as CTCL, and thus may be used as target genes in the methods described herein.

In some aspects, CTCL may be diagnosed or determined, and/or benign inflammatory dermatoses (BID) may be ruled out, based on upregulated expression of miR-326, miR-663b, miR-711, and/or miR-155 in CTCL compared to a control. In some aspects, CTCL may be diagnosed or determined, and/or BID may be ruled out, based on downregulated expression of miR-203 and/or miR-205 in CTCL compared to a control. In some embodiments, the microRNA expression is measured by microarray followed by PCR analysis. In some embodiments, these target genes are used to rule out a skin cancer other than CTCL.

In some aspects, CTCL may be diagnosed or determined, and/or benign inflammatory dermatoses (BID) may be ruled out, based on upregulated expression of miR-155, miR-21, miR-142, miR-146, and/or miR-181a/b in CTCL compared to a control. In some aspects, CTCL may be diagnosed or determined, and/or BID may be ruled out, based on downregulated expression of miR-141/200c in CTCL compared to a control. In some embodiments, the microRNA expression is measured using a microarray. In some embodiments, these target genes are used to rule out a skin cancer other than CTCL.

In some aspects, Sézary syndrome (a type of CTCL) may be diagnosed or determined, or ruled out, based on upregulated expression of miR-21, miR-214, and/or miR-486 in Sézary syndrome compared to a control. In some embodiments, the microRNA expression is measured using a microarray. In some embodiments, these target genes are used to rule out a skin cancer or CTCL other than Sézary syndrome.

In some aspects, an aggressive form of CTCL may be diagnosed or determined based on upregulated expression of miR-181a, miR-93, and/or miR-34a in aggressive forms of CTCL compared to a control such as a non-cancerous skin sample or compared to a non-aggressive or benign form of CTCL. In some embodiments, the microRNA expression is measured with PCR.

In some aspects, CTCL may be diagnosed or determined, and/or benign inflammatory dermatoses (BID) may be ruled out, based on upregulated or downregulated expression of miR-21. In some embodiments, the miR-21 expression is upregulated in a cancer such as bladder cancer. In some embodiments, the miR-21 expression is downregulated in a cancer such as PCNSL, glioblastoma, serosa-invasive gastric disorder, esophageal cancer, ovarian cancer, and/or NSCLC. In some embodiments, the miR-21 expression is measured in cerebrospinal fluid, ascites, urine, saliva, serum, and/or plasma.

In some embodiments, disclosed herein is a method of detecting the expression level of a gene from a gene classifier. In some instances, the method comprises detecting the expression level of FYN binding protein (FYB), IL2 inducible T-cell kinase (ITK), interleukin 26 (IL26), signal transducer and activator of transcription 5A (STAT5A), TRAF3 interacting protein 3 (TRAF3IP3), granulysin (GNLY), dynamin 3 (DNM3), tumor necrosis factor superfamily member 11 (TNFSF11), or a combination thereof. In some instances, the method comprises (a) isolating nucleic acids from a skin sample obtained from the subject, wherein the skin sample comprises cells from the stratum corneum; and (b) detecting the expression levels of FYB, ITK, IL26, STAT5A, TRAF3IP3, GNLY, DNM3, TNFSF11, or a combination thereof, by contacting the isolated nucleic acids with a set of probes that recognizes FYB, ITK, IL26, STAT5A, TRAF3IP3, GNLY, DNM3, TNFSF11, or a combination thereof, and detects binding between FYB, ITK, IL26, STAT5A, TRAF3IP3, GNLY, DNM3, TNFSF11, or a combination thereof and the set of probes. In the methods described herein, a gene classifier may include any target gene or combination of target genes described herein, and may include target gene expression levels or target gene mutations. Methods that describe a gene classifier may be used with target genes described herein in place of the gene classifier.

In some instances, the method comprises detecting the expression levels of two or more, three or more, or four or more of genes from the gene classifier: FYB, ITK, IL26, STAT5A, TRAF3IP3, GNLY, DNM3, and TNFSF11. In some cases, the method comprises detecting the expression levels of ITK, STAT5A, and TNFSF11. In some cases, the method comprises detecting the expression levels of ITK, IL26, STAT5A, and TNFSF11. In some cases, the method comprises detecting the expression levels of FYB, ITK, IL26, STAT5A, and TNFSF11. In some cases, the method comprises detecting the expression levels of FYB, ITK, IL26, STAT5A, TRAF3IP3, and TNFSF11. In some cases, the method comprises detecting the expression levels of FYB, ITK, IL26, STAT5A, TRAF3IP3, DNM3, and TNFSF11. In some cases, the method comprises detecting the expression levels of FYB, ITK, IL26, STAT5A, TRAF3IP3, GNLY, DNM3, and TNFSF11.

In some instances, the expression level is an elevated gene expression level. In some cases, the elevated gene expression level is compared to a gene expression level of an equivalent gene from a control sample. In some cases, the control sample is a normal skin sample. In some cases, the gene expression level of FYB, ITK, IL26, STAT5A, TRAF3IP3, DNM3, TNFSF11, or a combination thereof is elevated.

In some embodiments, the target gene expression is elevated by at least 1-fold, 2-fold, 3-fold, 4-fold, 5-fold, 10-fold, 20-fold, 30-fold, 40-fold, 50-fold, 60-fold, 70-fold, 80-fold, 90-fold, 100-fold, 110-fold, 120-fold, 130-fold, 150-fold, 200-fold, 300-fold, 500-fold, or more. In some embodiments, the target gene expression is decreased by at least 1-fold, 2-fold, 3-fold, 4-fold, 5-fold, 10-fold, 20-fold, 30-fold, 40-fold, 50-fold, 60-fold, 70-fold, 80-fold, 90-fold, 100-fold, 110-fold, 120-fold, 130-fold, 150-fold, 200-fold, 300-fold, 500-fold, or more. In some cases, the downregulated gene expression level is compared to a control. In some embodiments, the control is a gene expression level of an equivalent gene from a control sample. In some cases, the control sample is a normal skin sample.

In some cases, the gene expression level of FYB, ITK, IL26, STAT5A, TRAF3IP3, DNM3, or TNFSF11 is elevated by at least 1-fold, 2-fold, 3-fold, 4-fold, 5-fold, 10-fold, 20-fold, 30-fold, 40-fold, 50-fold, 60-fold, 70-fold, 80-fold, 90-fold, 100-fold, 110-fold, 120-fold, 130-fold, 150-fold, 200-fold, 300-fold, 500-fold, or more. In some cases, the gene expression level of FYB, ITK, IL26, STAT5A, TRAF3IP3, DNM3, or TNFSF11 is elevated by at least 10-fold. In some cases, the gene expression level of FYB, ITK, IL26, STAT5A, TRAF3IP3, DNM3, or TNFSF11 is elevated by at least 20-fold. In some cases, the gene expression level of FYB, ITK, IL26, STAT5A, TRAF3IP3, DNM3, or TNFSF11 is elevated by at least 30-fold. In some cases, the gene expression level of FYB, ITK, IL26, STAT5A, TRAF3IP3, DNM3, or TNFSF11 is elevated by at least 40-fold. In some cases, the gene expression level of FYB, ITK, IL26, STAT5A, TRAF3IP3, DNM3, or TNFSF11 is elevated by at least 50-fold. In some cases, the gene expression level of FYB, ITK, IL26, STAT5A, TRAF3IP3, DNM3, or TNFSF11 is elevated by at least 80-fold. In some cases, the gene expression level of FYB, ITK, IL26, STAT5A, TRAF3IP3, DNM3, or TNFSF11 is elevated by at least 100-fold. In some cases, the gene expression level of FYB, ITK, IL26, STAT5A, TRAF3IP3, DNM3, or TNFSF11 is elevated by at least 130-fold. In some cases, the gene expression level of FYB, ITK, IL26, STAT5A, TRAF3IP3, DNM3, or TNFSF11 is elevated by at least 150-fold. In some cases, the elevated gene expression level is compared to a gene expression level of an equivalent gene from a control sample. In some cases, the control sample is a normal skin sample.

In some cases, the gene expression level of FYB, ITK, IL26, STAT5A, TRAF3IP3, DNM3, or TNFSF11 is elevated by at least 10%, 20%, 30%, 40%, 50%, 60%, 70%, 80%, 90%, 100%, 200%, 300%, 400%, 500%, or more. In some cases, the gene expression level of FYB, ITK, IL26, STAT5A, TRAF3IP3, DNM3, or TNFSF11 is elevated by at least 10%. In some cases, the gene expression level of FYB, ITK, IL26, STAT5A, TRAF3IP3, DNM3, or TNFSF11 is elevated by at least 30%. In some cases, the gene expression level of FYB, ITK, IL26, STAT5A, TRAF3IP3, DNM3, or TNFSF11 is elevated by at least 50%. In some cases, the gene expression level of FYB, ITK, IL26, STAT5A, TRAF3IP3, DNM3, or TNFSF11 is elevated by at least 80%. In some cases, the gene expression level of FYB, ITK, IL26, STAT5A, TRAF3IP3, DNM3, or TNFSF11 is elevated by at least 100%. In some cases, the gene expression level of FYB, ITK, IL26, STAT5A, TRAF3IP3, DNM3, or TNFSF11 is elevated by at least 200%. In some cases, the gene expression level of FYB, ITK, IL26, STAT5A, TRAF3IP3, DNM3, or TNFSF11 is elevated by at least 300%. In some cases, the gene expression level of FYB, ITK, IL26, STAT5A, TRAF3IP3, DNM3, or TNFSF11 is elevated by at least 500%. In some cases, the elevated gene expression level is compared to a gene expression level of an equivalent gene from a control sample. In some cases, the control sample is a normal skin sample.

In some instances, the expression level is a down-regulated gene expression level. In some cases, the gene expression level of GNLY is down-regulated. In some cases, the down-regulated gene expression level is compared to a gene expression level of an equivalent gene from a control sample. In some cases, the control sample is a normal skin sample.

In some instances, the gene expression level of GNLY is down-regulated by at least 1-fold, 2-fold, 3-fold, 4-fold, 5-fold, 10-fold, 20-fold, 30-fold, 40-fold, 50-fold, 60-fold, 70-fold, 80-fold, 90-fold, 100-fold, 110-fold, 120-fold, 130-fold, 150-fold, 200-fold, 300-fold, 500-fold, or more. In some cases, the gene expression level of GNLY is down-regulated by at least 1-fold. In some cases, the gene expression level of GNLY is down-regulated by at least 5-fold. In some cases, the gene expression level of GNLY is down-regulated by at least 10-fold. In some cases, the gene expression level of GNLY is down-regulated by at least 20-fold. In some cases, the gene expression level of GNLY is down-regulated by at least 30-fold. In some cases, the gene expression level of GNLY is down-regulated by at least 40-fold. In some cases, the gene expression level of GNLY is down-regulated by at least 50-fold. In some cases, the gene expression level of GNLY is down-regulated by at least 100-fold.

In some instances, the gene expression level of GNLY is down-regulated by at least 10%, 20%, 30%, 40%, 50%, 60%, 70%, 80%, 90%, 100%, 200%, 300%, 400%, 500%, or more. In some cases, the gene expression level of GNLY is down-regulated by at least 10%. In some cases, the gene expression level of GNLY is down-regulated by at least 20%. In some cases, the gene expression level of GNLY is down-regulated by at least 30%. In some cases, the gene expression level of GNLY is down-regulated by at least 50%. In some cases, the gene expression level of GNLY is down-regulated by at least 80%. In some cases, the gene expression level of GNLY is down-regulated by at least 100%.

In some embodiments, the set of probes recognizes at least one but no more than eight genes selected from FYB, ITK, IL26, STAT5A, TRAF3IP3, GNLY, DNM3, and TNFSF11. In some cases, the set of probes recognizes ITK, STAT5A, and TNFSF11. In some cases, the set of probes recognizes ITK, IL26, STAT5A, and TNFSF11. In some cases, the set of probes recognizes FYB, ITK, IL26, STAT5A, and TNFSF11. In some cases, the set of probes recognizes FYB, ITK, IL26, STAT5A, TRAF3IP3, and TNFSF11. In some cases, the set of probes recognizes FYB, ITK, IL26, STAT5A, TRAF3IP3, DNM3, and TNFSF11. In some cases, the set of probes recognizes FYB, ITK, IL26, STAT5A, TRAF3IP3, GNLY, DNM3, and TNFSF11.

In some embodiments, the method further comprises detecting the expression levels of thymocyte selection associated high mobility group box (TOX); lymphoid enhancer binding factor 1 (LEF1); C-C motif chemokine receptor 4 (CCR4); POU class 2 associating factor 1 (POU2AF1); gametocyte specific factor 1 (GTSF1); plastin 3 (PLS3); matrix metallopeptidase 12 (WP12); LCK proto-oncogene, Src family tyrosine kinase (LCK); neural precursor cell expressed, developmentally down-regulated (NEDD4L); or a combination thereof. In some cases, the detecting comprises contacting the isolated nucleic acids with an additional set of probes that recognizes TOX, LEF1, CCR4, POU2AF1, GTSF1, PLS3, MMP12, LCK, NEDD4L, or a combination thereof, and detects binding between TOX, LEF1, CCR4, POU2AF1, GTSF1, PLS3, MMP12, LCK, NEDD4L, or a combination thereof and the additional set of probes.

In some cases, the additional set of probes recognizes one but no more than nine genes. In some cases, the additional set of probes recognizes 2, 3, 4, 5, 6, 7, 8, or 9 genes selected from TOX, LEF1, CCR4, POU2AF1, GTSF1, PLS3, MMP12, LCK, and NEDD4L.

In some cases, the expression level of one or more genes selected from TOX, LEF1, CCR4, POU2AF1, GTSF1, PLS3, MMP12, LCK, and NEDD4L is an elevated gene expression level. In such cases, the gene expression level is elevated by at least 1-fold, 2-fold, 3-fold, 4-fold, 5-fold, 10-fold, 20-fold, 30-fold, 40-fold, 50-fold, 60-fold, 70-fold, 80-fold, 90-fold, 100-fold, 110-fold, 120-fold, 130-fold, 150-fold, 200-fold, 300-fold, 500-fold, or more. In some instances, the gene expression level is elevated by at least 10%, 20%, 30%, 40%, 50%, 60%, 70%, 80%, 90%, 100%, 200%, 300%, 400%, 500%, or more. In some instances, the expression level is compared to a gene expression level of an equivalent gene from a control sample. In some instances, the control sample is a normal skin sample.

In additional cases, the expression level of one or more genes selected from TOX, LEF1, CCR4, POU2AF1, GTSF1, PLS3, MMP12, LCK, and NEDD4L is a down-regulated gene expression level. In such cases, the gene expression level is down-regulated by at least 1-fold, 2-fold, 3-fold, 4-fold, 5-fold, 10-fold, 20-fold, 30-fold, 40-fold, 50-fold, 60-fold, 70-fold, 80-fold, 90-fold, 100-fold, 110-fold, 120-fold, 130-fold, 150-fold, 200-fold, 300-fold, 500-fold, or more. In some instances, the gene expression level is down-regulated by at least 10%, 20%, 30%, 40%, 50%, 60%, 70%, 80%, 90%, 100%, 200%, 300%, 400%, 500%, or more. In some instances, the expression level is compared to a gene expression level of an equivalent gene from a control sample. In some instances, the control sample is a normal skin sample.

In some embodiments, a method described herein further comprises differentiating a skin cancer sample (e.g., a CTCL positive sample) from a non-cancer sample. In some cases, the method has an improved specificity. In some instances, the specificity is at least or about 70%, 75%, 80%, 85%, 90%, or more than 95% when detecting the gene expression level of FYB, ITK, IL26, STAT5A, TRAF3IP3, DNM3, TNFSF11, or a combination thereof. In some embodiments, the specificity is at least or about 70%, 75%, 80%, 85%, 90%, or more than 95% when detecting the gene expression level of TOX, LEF1, CCR4, POU2AF1, GTSF1, PLS3, MMP12, LCK, NEDD4L, or a combination thereof.

In some cases, the method also has an improved sensitivity. In some embodiments, the sensitivity is at least or about 70%, 75%, 80%, 85%, 90%, or more than 95% when detecting the gene expression levels of FYB, ITK, IL26, STAT5A, TRAF3IP3, DNM3, TNFSF11, or a combination thereof. In some embodiments, the sensitivity is at least or about 70%, 75%, 80%, 85%, 90%, or more than 95% when detecting the gene expression levels of TOX, LEF1, CCR4, POU2AF1, GTSF1, PLS3, MMP12, LCK, NEDD4L, or a combination thereof.

In some embodiments, a method described herein comprises detecting gene expression levels from a first gene classifier and a second gene classifier in a subject in need thereof, comprising: (a) isolating nucleic acids from a skin sample obtained from the subject, wherein the skin sample comprises cells from the stratum corneum; (b) detecting the expression levels of one or more genes from the first gene classifier: FYB, ITK, IL26, STAT5A, TRAF3IP3, GNLY, DNM3, and TNFSF11, by contacting the isolated nucleic acids with a set of probes that recognizes one or more genes from the first gene classifier, and detects binding between one or more genes from the first gene classifier and the set of probes; and (c) detecting the expression levels of one or more genes from the second gene classifier: TOX, LEF1, CCR4, POU2AF1, GTSF1, PLS3, MMP12, LCK, and NEDD4L, by contacting the isolated nucleic acids with an additional set of probes that recognizes one or more genes from the second gene classifier, and detects binding between one or more genes from the second gene classifier and the additional set of probes.

In some embodiments, a method described herein further comprises use of one or more additional targets to determine the presence of a skin cancer (e.g., CTCL). In some instances, the one or more additional targets include a target suitable for assessing CD4 to CD8 ratios, e.g., a target obtained from an immunohistochemistry analyses. In some instances, the one or more additional targets include CD4, CD7, CD8, and related CD markers such as CD45RA and CD45RO. In some instances, the one or more additional targets include a target suitable for assessing a loss of CD7 within a skin sample. In some instances, the one or more additional targets include a target suitable for assessing Th2 function (e.g., an increased expression of IL-4, IL-5, IL-10, or TGF-beta). In some instances, the one or more additional targets include a chemokine receptor family member such as CCR4 and CCR7. In some instances, the one or more additional targets include cutaneous lymphocyte-associated antigen (CLA). In some instances, the one or more additional targets include a micro RNA or mutation associated with non-cutaneous lymphomas.

In some embodiments, a number of probes in the set of probes described above is at least or about 1, 2, 3, 5, 6, 7, 8, 9, 10, 11, 12, 13, 14, 15, 16, 17, 18, 19, 20, 25, 30, or more than 30 probes. In some embodiments, the number of probes in the set of probes is about 6 probes. In some embodiments, the number of probes in the set of probes is about 7 probes. In some embodiments, the number of probes in the set of probes is about 8 probes. In some embodiments, the number of probes in the set of probes is about 9 probes. In some embodiments, the number of probes in the set of probes is about 13 probes.

In some embodiments, the set of probes comprises one or more primer pairs. In some embodiments, a number of primer pairs is at least or about 1, 2, 3, 5, 6, 7, 8, 9, 10, 11, 12, 13, 14, 15, 16, 17, 18, 19, 20, 25, 30, or more than 30 primer pairs. In some embodiments, the number of primer pairs is about 6 primer pairs. In some embodiments, the number of primer pairs is about 7 primer pairs. In some embodiments, the number of primer pairs is about 13 primer pairs.

In some embodiments, one or more probes in the set of probes is labeled. In some embodiments, the one or more probe is labeled with a radioactive label, a fluorescent label, an enzyme, a chemiluminescent tag, a colorimetric tag, an affinity tag or other labels or tags that are known in the art.

Exemplary affinity tags include, but are not limited to, biotin, desthiobiotin, histidine, polyhistidine, myc, hemagglutinin (HA), FLAG, glutathione S transferase (GST), or derivatives thereof. In some embodiments, the affinity tag is recognized by avidin, streptavidin, nickel, or glutathione.

In some embodiments, the fluorescent label is a fluorophore, a fluorescent protein, a fluorescent peptide, quantum dots, a fluorescent dye, a fluorescent material, or variations or combinations thereof.

Exemplary fluorophores include, but are not limited to, Alexa-Fluor dyes (e.g., Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 647, Alexa Fluor® 660, Alexa Fluor® 680, Alexa Fluor® 700, and Alexa Fluor® 750), APC, Cascade Blue, Cascade Yellow and R-phycoerythrin (PE), DyLight 405, DyLight 488, DyLight 550, DyLight 650, DyLight 680, DyLight 755, DyLight 800, FITC, Pacific Blue, PerCP, Rhodamine, and Texas Red, Cy5, Cy5.5, Cy7.

Examples of fluorescent peptides include but are not limited to GFP (Green Fluorescent Protein) or derivatives of GFP (e.g., EBFP, EBFP2, Azurite, mKalamal, ECFP, Cerulean, CyPet, YFP, Citrine, Venus, and YPet.

Examples of fluorescent dyes include, but are not limited to, xanthenes (e.g., rhodamines, rhodols and fluoresceins, and their derivatives); bimanes; coumarins and their derivatives (e.g., umbelliferone and aminomethyl coumarins); aromatic amines (e.g., dansyl; squarate dyes); benzofurans; fluorescent cyanines; indocarbocyanines; carbazoles; dicyanomethylene pyranes; polymethine; oxabenzanthrane; xanthene; pyrylium; carbostyl; perylene; acridone; quinacridone; rubrene; anthracene; coronene; phenanthrecene;

pyrene; butadiene; stilbene; porphyrin; pthalocyanine; lanthanide metal chelate complexes; rare-earth metal chelate complexes; and derivatives of such dyes. In some embodiments, the fluorescein dye is, but not limited to, 5-carboxyfluorescein, fluorescein-5-isothiocyanate, fluorescein-6-isothiocyanate and 6-carboxyfluorescein. In some embodiments, the rhodamine dye is, but not limited to, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, and rhodamine 101 sulfonyl chloride (sold under the tradename of TEXAS RED®). In some embodiments, the cyanine dye is Cy3, Cy3B, Cy3.5, Cy5, Cy5.5, Cy7, IRDYE680, Alexa Fluor 750, IRDye800CW, or ICG.

In some embodiments, the gene expression levels of FYB, ITK, IL26, STAT5A, TRAF3IP3, GNLY, DNM3, TNFSF11, or a combination thereof is measured using PCR. Examples of PCR techniques include, but are not limited to quantitative PCR (qPCR), single cell PCR, PCR-RFLP, digital PCR (dPCR), droplet digital PCR (ddPCR), single marker qPCR, hot start PCR, and Nested PCR.

In some embodiments, the gene expression levels of TOX, LEF1, CCR4, POU2AF1, GTSF1, PLS3, MMP12, LCK, NEDD4L, or a combination thereof is measured using PCR. Examples of PCR techniques include, but are not limited to quantitative PCR (qPCR), single cell PCR, PCR-RFLP, digital PCR (dPCR), droplet digital PCR (ddPCR), single marker qPCR, hot start PCR, and Nested PCR.

In some embodiments, the expression levels are measured using qPCR. In some embodiments, the qPCR comprises use of fluorescent dyes or fluorescent probes. In some embodiments, the fluorescent dye is an intercalating dye. Examples of intercalating dyes include, but are not limited to, intercalating dyes include SYBR green I, SYBR green II, SYBR gold, ethidium bromide, methylene blue, Pyronin Y, DAPI, acridine orange, Blue View, or phycoerythrin. In some embodiments, the qPCR comprises use of more than one fluorescent probe. In some embodiments, the use of more than one fluorescent probes allows for multiplexing. For example, different non-classical variants are hybridized to different fluorescent probes and can be detected in a single qPCR reaction. Some embodiments include detecting or measuring an amount of binding between genes of interest and a set of probes, and includes detecting or measuring a fluorescent dye or a fluorescent probe.

Disclosed herein, in some embodiments, are methods of determining the presence of a skin cancer or non-Hodgkin's lymphoma such as a cutaneous T cell lymphoma (CTCL). Some embodiments include isolating nucleic acids from a skin sample obtained from a subject. Some embodiments include measuring, detecting, receiving, or using an expression level of a target gene. Some embodiments include detecting an expression level of a target gene in the skin sample. Some embodiments include measuring an expression level of a target gene in the skin sample. Some embodiments include receiving an expression level of a target gene in the skin sample. Some embodiments include using an expression level of a target gene in the skin sample. Some embodiments include measuring an expression level of a target gene in the skin sample. Some embodiments include measuring or detecting an expression level of the target gene.

Some embodiments include multiple target genes. For example, multiple target genes may be measured, detected, or used in the methods described herein. Some embodiments include determining the presence of a skin cancer (e.g. CTCL) based on a presence or expression level of a first target gene, and based on a mutation in a second target gene. Some embodiments include determining the presence of a skin cancer (e.g. CTCL) based on a presence or expression level of multiple target genes. Some embodiments include determining the presence of a skin cancer (e.g. CTCL) based on mutations in multiple target genes. Some embodiments include determining the presence of a skin cancer (e.g. CTCL) based on a presence or expression level of multiple target genes s, and based on mutations in multiple target genes.

Some embodiments include more than one target gene (e.g., at least one target gene). For example, the method may include measuring, detecting, receiving, or using expression levels of multiple target genes. Some embodiments include 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 250, 300, 350, 400, 450, 500, 550, 600, 650, 700, 750, 800, 850, 900, 950, 1000, or more target genes. Some embodiments include 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 250, 300, 350, 400, 450, 500, 550, 600, 650, 700, 750, 800, 850, 900, 950, 1000, or more target genes, or a range of target genes defined by any two of the aforementioned integers. For example, some embodiments include measuring or detecting an expression level of 17 target genes. Some embodiments include measuring or detecting an expression level of 8 target genes. Some embodiments include measuring or detecting an expression level of 1-10 target genes. Some embodiments include measuring or detecting an expression level of 1-100 target genes. Some embodiments include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 55, at least 60, at least 65, at least 70, at least 75, at least 80, at least 85, at least 90, at least 95, or at least 100 target genes. Some embodiments include no more than 1, no more than 2, no more than 3, no more than 4, no more than 5, no more than 6, no more than 7, no more than 8, no more than 9, no more than 10, no more than 11, no more than 12, no more than 13, no more than 14, no more than 15, no more than 16, no more than 17, no more than 18, no more than 19, no more than 20, no more than 25, no more than 30, no more than 35, no more than 40, no more than 45, no more than 50, no more than 55, no more than 60, no more than 65, no more than 70, no more than 75, no more than 80, no more than 85, no more than 90, no more than 95, or no more than 100 target genes.

In some embodiments, the nucleic acids comprise RNA. In some embodiments, the nucleic acids comprise mRNA. In some embodiments, measuring or detecting the expression level of the target gene comprises measuring or detecting an amount of RNA or mRNA encoded by a nucleic acid comprising the target gene. In some embodiments, measuring or detecting the expression level of the target gene comprises measuring or detecting an amount of mRNA encoded by a nucleic acid comprising the target gene. In some embodiments, using or receiving the expression level of the target gene comprises using or receiving information on an amount of RNA or mRNA encoded by a nucleic acid comprising the target gene.

Disclosed herein, in some embodiments, are target gene mutations. In some embodiments, the target gene comprises a target gene mutation. In some embodiments, the target gene mutation includes a hotspot somatic mutation (e.g.

driver mutation). In some embodiments, the target gene mutation includes a significantly mutated gene. In some embodiments, the target gene mutation includes a hotspot somatic mutation from a significantly mutated gene. In some embodiments, the target gene comprises TP53. In some embodiments, the target gene comprises ZEB1. In some embodiments, the target gene comprises ARID1A. In some embodiments, the target gene comprises DNMT3A. In some embodiments, the target gene comprises CDKN2A. In some embodiments, the target gene comprises FAS. In some embodiments, the target gene comprises STAT5B. In some embodiments, the target gene comprises PRKCQ. In some embodiments, the target gene comprises RHOA. In some embodiments, the target gene comprises DNMT3A. In some embodiments, the target gene comprises PLCG1. In some embodiments, the target gene comprises NFKB2. In some embodiments, the target gene mutation comprises a mutation in any of TP53, ZEB1, ARID1A, DNMT3A, CDKN2A, FAS, STAT5B, PRKCQ, RHOA, DNMT3A, PLCG1, or NFKB2.

Some embodiments comprise a deletion mutation in one or more of TP53, ZEB1, ARID1A, DNMT3A, FAS, or CDKN2A. In some embodiments, the deletion mutation occurs in a subject with CTCL. Some embodiments comprise a deletion mutation in TP53. Some embodiments comprise a deletion mutation in ZEB1. Some embodiments comprise a deletion mutation in ARID1A. Some embodiments comprise a deletion mutation in DNMT3A. Some embodiments comprise a deletion mutation in FAS. Some embodiments comprise a deletion mutation in CDKN2A.

Some embodiments comprise a truncation. In some embodiments, the truncation occurs in a subject with CTCL. Some embodiments comprise a truncation of NFKB2. In some embodiments, the truncation is a C-terminal truncation. Some embodiments comprise a C-terminal truncation of NFKB2.

Some embodiments include a TP53 mutation. In some embodiments, the TP53 mutation comprises a Ser34* mutation. In some embodiments, the TP53 mutation comprises a Ser94* mutation. In some embodiments, the TP53 mutation comprises a Thr155Asn mutation. In some embodiments, the TP53 mutation comprises an Arg196*mutation. In some embodiments, the TP53 mutation comprises an Ala215Val mutation. In some embodiments, the TP53 mutation comprises an Ile254Thr mutation. In some embodiments, the TP53 mutation comprises an Arg273Pro mutation.

Some embodiments include a CD28 mutation. In some embodiments, the CD28 mutation comprises a Phe51Ile mutation. In some embodiments, the CD28 mutation comprises a Phe51Val mutation. In some embodiments, the CD28 mutation comprises a Gln77Pro mutation. In some embodiments, the CD28 mutation comprises a Lys81Asn mutation.

Some embodiments include a RhoA mutation. In some embodiments, the RhoA mutation comprises an Arg70Lys mutation. In some embodiments, the RhoA mutation comprises an Asn117Ile mutation.

Some embodiments include a DNMT3A mutation. In some embodiments, the DNMT3A mutation comprises a Pro233Leu mutation. In some embodiments, the DNMT3A mutation comprises a Tyr584* mutation. In some embodiments, the DNMT3A mutation comprises a Ser669Phe mutation. In some embodiments, the DNMT3A mutation comprises a Pro777Leu mutation.

Some embodiments include a FAS mutation. In some embodiments, the FAS mutation comprises a Ser212Cys mutation. In some embodiments, the FAS mutation comprises a Glu261Lys mutation. In some embodiments, the FAS mutation comprises an Asp265 Glu mutation.

Some embodiments include a PLCG1 mutation. In some embodiments, the PLCG1 mutation comprises an Arg48Trp mutation. In some embodiments, the PLCG1 mutation comprises an Asp342Asn mutation. In some embodiments, the PLCG1 mutation comprises a Ser345Phe mutation. In some embodiments, the PLCG1 mutation comprises a Glu1163Lys mutation.

Some embodiments include detecting the presence at least one genotype of one more target genes. Some embodiments include detecting the presence at least one genotype of one more target genes known to be mutated in subjects with CTCL, in nucleic acids isolated from the skin sample of a subject suspected of having CTCL. In some embodiments, the nucleic acids comprise or consist of DNA. Some embodiments include determining whether the subject has CTCL based on the presence of the at least one genotype. Some embodiments include methods of determining the presence of a skin cancer such as a cutaneous T cell lymphoma (CTCL), using a target gene mutation as described herein. Some embodiments comprise detecting a mutational change in a target gene. Some embodiments include detecting a mutational change of a target gene.

Some embodiments relate to detecting expression levels of one or more target genes, and detecting a target gene mutation in one or more other target genes. Some embodiments relate to detecting expression levels of one or more target genes, and detecting a target gene mutation in one or more of the same target genes.

In some instances, the mutation is a missense substitution, a nonsense substitution (*), a coding silent substitution, deletion (del), an insertion (ins), or a frameshift (fs). In some instances, both expression level and mutational change provide information regarding the skin cancer in the subject. Information regarding the disease includes, but is not limited to, identification of a skin cancer, likelihood of treatment success for a skin cancer, identification of progression of a skin cancer, and identification of a skin cancer stage. In some instances, at least one of expression level and mutational change are compared to a control sample for identification of the skin cancer, determining likelihood of treatment success for the skin cancer, identification of progression of the skin cancer, or identification of the skin cancer stage. In some instances, the control sample is any sample that is used for making any one of these determinations. In some instances, the control sample is from a healthy individual. In some instances, the control is a sample from an individual with a known disease or disorder. In some instances, the control is from a database or reference. In some instances, the control is a normal sample from the same individual. In some instances, the normal sample is a sample that does not comprise skin cancer, or a sample that would test negative for skin cancer. In some instances, the normal sample is assayed at the same time or at a different time.

Disclosed herein, in some embodiments, are methods of determining the presence of a skin cancer such as a cutaneous T cell lymphoma (CTCL), comprising isolating nucleic acids from a skin sample obtained from a subject, and detecting an expression level of a target gene. Some embodiments include measuring or detecting an expression level of the target gene. Some embodiments include detecting an expression level of the target gene. Some embodiments include measuring an expression level of the target gene. Some embodiments include more than one target gene (e.g., at least one target gene). In some embodiments, measuring or detecting the expression level of the target gene comprises measuring or detecting an amount of RNA or mRNA encoded by a nucleic acid comprising the target gene.

Disclosed herein, in some embodiments, are methods of determining the presence of cutaneous T cell lymphoma (CTCL) in a skin sample. Some embodiments include identifying a subject suspected of having CTCL. Some embodiments include isolating nucleic acids from a skin sample obtained from the subject. In some embodiments, the skin sample is obtained by applying an adhesive patch to a skin region of the subject. In some embodiments, the adhesive patch is applied in a manner sufficient to adhere skin sample cells to the adhesive patch. In some embodiments, the skin sample is further obtained by removing the adhesive patch from the skin sample in a manner sufficient to retain the adhered skin sample cells to the adhesive patch. In some embodiments, the skin sample cells comprise cells from the stratum corneum. In some embodiments, the skin sample cells consist of cells from the stratum corneum. Some embodiments include isolating nucleic acids from a skin sample obtained from the subject by applying an adhesive patch to a skin region of the subject in a manner sufficient to adhere skin sample cells to the adhesive patch, and removing the adhesive patch from the skin sample in a manner sufficient to retain the adhered skin sample cells to the adhesive patch, wherein the skin sample cells comprise or consist of cells from the stratum corneum. Some embodiments include measuring or detecting an expression level of at least one target gene. In some embodiments, the at least one target gene is known to be upregulated or downregulated in subjects with CTCL. Some embodiments include contacting the isolated nucleic acids with a set of probes that recognize the target gene. Some embodiments include detecting binding between the at least one target gene and the set of probes.

Disclosed herein, in some embodiments, are methods of determining the presence of cutaneous T cell lymphoma (CTCL) in a skin sample, comprising: identifying a subject suspected of having CTCL; isolating nucleic acids from a skin sample obtained from the subject by applying an adhesive patch to a skin region of the subject in a manner sufficient to adhere skin sample cells to the adhesive patch, and removing the adhesive patch from the skin sample in a manner sufficient to retain the adhered skin sample cells to the adhesive patch, wherein the skin sample cells comprise cells from the stratum corneum; and measuring or detecting an expression level of at least one target gene known to be upregulated or downregulated in subjects with CTCL, by contacting the isolated nucleic acids with a set of probes that recognize the target gene, and detecting binding between the at least one target gene and the set of probes.

Some embodiments include determining whether the subject has CTCL based on the expression level of the at least one target gene. In some embodiments, the expression level is upregulated compared to a gene expression level of an equivalent gene from a control sample. In some embodiments, the expression level is downregulated compared to a gene expression level of an equivalent gene from a control sample. In some embodiments, the at least one target gene comprises a gene encoding an adapter protein. In some embodiments, the at least one target gene comprises a gene encoding a tyrosine kinase. In some embodiments, the at least one target gene comprises a gene encoding an interleukin. In some embodiments, the at least one target gene comprises a gene encoding a transcription factor. In some embodiments, the at least one target gene comprises a gene encoding a TNF receptor associated factor protein. In some embodiments, the at least one target gene comprises a gene encoding a TNF. In some embodiments, the at least one target gene comprises a gene encoding a saposin-like protein. In some embodiments, the at least one target gene comprises a gene encoding a GTP-binding protein. In some embodiments, the at least one target gene comprises a gene encoding a chromatin associated protein. In some embodiments, the at least one target gene comprises a gene encoding a G-protein-coupled receptor. In some embodiments, the at least one target gene comprises a gene encoding a transcriptional coactivator. In some embodiments, the at least one target gene comprises a gene encoding a spermatogenesis protein. In some embodiments, the at least one target gene comprises a gene encoding an actin-binding protein. In some embodiments, the at least one target gene comprises a gene encoding a matrix metalloproteinase. In some embodiments, the at least one target gene comprises a gene encoding a ubiquitin ligase. In some embodiments, the at least one target gene comprises a gene encoding modulator of cell death. In some embodiments, the at least one target gene comprises a gene encoding an antimicrobial. In some embodiments, the at least one target gene comprises a gene encoding a cytokine. In some embodiments, the at least one target gene comprises a gene encoding a DNA-binding protein. In some embodiments, the at least one target gene comprises a FYN-binding protein family member. In some embodiments, the at least one target gene comprises a TEC kinase family member. In some embodiments, the at least one target gene comprises a STAT. In some embodiments, the at least one target gene comprises a TRAF3 interacting protein. In some embodiments, the at least one target gene comprises a dynamin family member. In some embodiments, the at least one target gene comprises a TNF superfamily member. In some embodiments, the at least one target gene comprises a thymocyte selection associated high mobility group box family member. In some embodiments, the at least one target gene comprises a lymphoid enhancer binding factor family member. In some embodiments, the at least one target gene comprises a C-C chemokine receptor type family member. In some embodiments, the at least one target gene comprises an Oct binding factor family member. In some embodiments, the at least one target gene comprises a gametocyte-specific family member. In some embodiments, the at least one target gene comprises a plastin family member. In some embodiments, the at least one target gene comprises a lymphocyte-specific protein tyrosine kinase family member. In some embodiments, the at least one target gene comprises a member of the NEDD4 family of E3 HECT domain ubiquitin ligases. In some embodiments, the at least one target gene comprises a C-C motif chemokine ligand family member. In some embodiments, the at least one target gene comprises a chemokine. In some embodiments, the at least one target gene comprises a CXC chemokine.

In some embodiments, the at least one target gene comprises a gene encoding a saposin-like protein, a gene encoding a FYN-binding protein family member, a gene encoding a TEC kinase family member, a gene encoding a STAT, a gene encoding a TRAF3 interacting protein, a gene encoding a CXC chemokine family member, and/or a combination thereof. In some embodiments, the at least one target gene is upregulated.

Disclosed herein, in some embodiments, are methods for non-invasively identifying a cutaneous T cell lymphoma (CTCL) in a subject suspected of having the CTCL. In some embodiments, the method includes isolating nucleic acids from a skin sample adhered to an adhesive patch, the skin sample having been obtained from the subject suspected of having the CTCL. Some embodiments include contacting the isolated nucleic acids with a set of probes that recognize one or more genes of interest implicated in the CTCL. Some embodiments include detecting or measuring an amount of binding between the genes of interest and the set of probes. Some embodiments include comparing the amount of binding between the genes of interest and the set of probes to a control or threshold amount of binding. Some embodiments include identifying the subject as having the CTCL, or as not having the CTCL, based on the amount of binding between the genes of interest and the set of probes relative to the control or threshold of binding. In some embodiments, identifying the subject as having the CTCL, or as not having the CTCL, based on the amount of binding between the genes of interest and the set of probes relative to the control or threshold amount of binding comprises applying the amount of binding to a random forest model, a boosting model, a logit model, a lasso model, or a combination thereof, and comprises taking into account interactions of the genes of interest. Some embodiments include administering an effective amount of a therapeutic agent to the subject identified as having the CTCL.

Disclosed herein, in some embodiments, are methods for non-invasively identifying a cutaneous T cell lymphoma (CTCL) in a subject suspected of having NMSC, the method comprising: isolating nucleic acids from a skin sample adhered to an adhesive patch, the skin sample having been obtained from the subject suspected of having the CTCL; contacting the isolated nucleic acids with a set of probes that recognize one or more genes of interest implicated in CTCL; and detecting or measuring an amount of binding between the genes of interest and the set of probes.

Disclosed herein, in some embodiments, are methods for non-invasively identifying a cutaneous T cell lymphoma (CTCL). Some embodiments include identifying a subject suspected of having the CTCL. Some embodiments include applying an adhesive patch to the subject's skin in a manner sufficient to adhere a skin sample to the adhesive patch. Some embodiments include removing the adhesive patch from the subject's skin in a manner sufficient to retain the skin sample adhered to the adhesive patch. Some embodiments include obtaining expression levels of genes of interest implicated in CTCL, or determining an amount of binding between the genes of interest and a set of probes that recognize the genes of interest.

Disclosed herein, in some embodiments, are methods for non-invasively identifying a cutaneous T cell lymphoma (CTCL), comprising: identifying a subject suspected of having the CTCL; applying an adhesive patch to the subject's skin in a manner sufficient to adhere a skin sample to the adhesive patch; removing the adhesive patch from the subject's skin in a manner sufficient to retain the skin sample adhered to the adhesive patch; and obtaining expression levels of genes of interest implicated in CTCL, or determining an amount of binding between the genes of interest and a set of probes that recognize the genes of interest.

Disclosed herein, in some embodiments, are methods for non-invasively identifying cutaneous T cell lymphoma (CTCL) in a subject suspected of having CTCL. In some embodiments, the method includes isolating nucleic acids from a skin sample adhered to an adhesive patch. In some embodiments, the skin sample was obtained from the stratum corneum of the subject suspected of having CTCL. Some embodiments include contacting the isolated nucleic acids with a set of probes that recognize target genes; and detecting or measuring an amount of binding between the nucleic acids and the set of probes.

Disclosed herein, in some embodiments, are methods for non-invasively identifying cutaneous T cell lymphoma (CTCL) in a subject suspected of having CTCL, the method comprising: isolating nucleic acids from a skin sample adhered to an adhesive patch, the skin sample having been obtained from the stratum corneum of the subject suspected of having CTCL; contacting the isolated nucleic acids with a set of probes that recognize target genes; and detecting or measuring an amount of binding between the nucleic acids and the set of probes.

Disclosed herein, in some embodiments, are methods for non-invasively identifying cutaneous T cell lymphoma (CTCL). In some embodiments, the method includes identifying a subject suspected of having CTCL. Some embodiments include applying an adhesive patch to the subject's skin in a manner sufficient to adhere a skin sample to the adhesive patch. Some embodiments include removing the adhesive patch from the subject's skin in a manner sufficient to retain the skin sample adhered to the adhesive patch. Some embodiments include obtaining expression levels of target genes implicated in CTCL. Some embodiments include determining an amount of binding between the genes of interest and a set of probes that recognize the target genes.

Disclosed herein, in some embodiments, are methods for non-invasively identifying cutaneous T cell lymphoma (CTCL), comprising: identifying a subject suspected of having CTCL; applying an adhesive patch to the subject's skin in a manner sufficient to adhere a skin sample to the adhesive patch; removing the adhesive patch from the subject's skin in a manner sufficient to retain the skin sample adhered to the adhesive patch; and obtaining expression levels of target genes implicated in CTCL, or determining an amount of binding between the genes of interest and a set of probes that recognize the target genes.

Some embodiments of the methods described herein include detecting the presence at least one genotype of one or more additional target genes known to be mutated in subjects with CTCL, in the nucleic acids or in a separate set of nucleic acids isolated from the skin sample. In some embodiments, the nucleic acids or the separate set of nucleic acids comprise DNA. In some embodiments, determining whether the subject has CTCL further comprises determining whether the subject has CTCL based on the presence of the at least one genotype.

Described herein, in some embodiments, are methods of detecting gene expression levels and mutational changes in a skin sample. In some embodiments, the method includes isolating nucleic acids from the skin sample. Some embodiments include measuring or detecting expression levels of one or more target genes. Some embodiments include detecting a mutational change of one or more other target genes. In some embodiments, the gene expression levels are detected by contacting the isolated nucleic acids with a set of probes, and detecting binding between the target genes and the set of probes. Some embodiments include contacting the isolated nucleic acids with a set of probes. Some embodiments include contacting detecting binding between the target genes and the set of probes. Some embodiments include detecting the gene expression levels by contacting the isolated nucleic acids with a set of probes, and detecting binding between the target genes and the set of probes.

Described herein, in some embodiments, are methods of detecting gene expression levels and mutational changes in a skin sample, comprising: isolating nucleic acids from the skin sample; and detecting the expression levels of one or more target genes; and a mutational change of one or more other target genes; wherein the gene expression levels are detected by contacting the isolated nucleic acids with a set of probes, and detecting binding between the target genes and the set of probes.

Methods of Treatment

Disclosed herein, in some embodiments, are methods of treating a subject suspected of having skin cancer. Some embodiments include methods of treating a subject with a skin cancer. In some embodiments, the method includes identifying a subject suspected of having the skin cancer. Some embodiments include isolating nucleic acids from a skin sample of the subject. In some embodiments, the skin sample is obtained from the subject by applying an adhesive patch to a skin region of the subject. In some embodiments, the adhesive patch is applied in a manner sufficient to adhere skin sample cells. In some embodiments, the skin sample is obtained from the subject further by removing the adhesive patch from the skin sample. In some embodiments, the adhesive patch is removed in a manner sufficient to retain the adhered skin sample cells to the adhesive patch. In some embodiments, the skin sample cells comprise cells from the stratum corneum. In some embodiments, the skin sample cells consist of cells from the stratum corneum. Some embodiments include measuring or detecting an expression level of at least one target gene. The target gene may include any of the target genes s described herein. In some embodiments, the at least one target gene is known to be upregulated or downregulated in subjects with the skin cancer. In some embodiments, the at least one target gene is upregulated or downregulated in the subject. Some embodiments include contacting the isolated nucleic acids with a set of probes that recognize the target gene. Some embodiments include detecting binding between the at least one target gene and the set of probes. In some embodiments, the expression level is detected or measured by contacting the isolated nucleic acids with a set of probes that recognize the target gene, and detecting binding between the at least one target gene and the set of probes. Some embodiments include receiving the expression level of the at least one target gene, wherein the expression level was measured or detected using a method as described herein. Some embodiments include determining whether the subject has the skin cancer based on the expression level of the at least one target gene. Some embodiments include administering a skin cancer treatment to the subject. Some embodiments include administering the skin cancer treatment to the subject when the subject is determined to have the skin cancer based on the expression level of the at least one target gene. Some embodiments include not administering the skin cancer treatment to the subject if the subject is not determined to have cancer based on the expression level of the at least one target gene. Some embodiments include withholding the skin cancer treatment from the subject when the subject is not determined to have skin cancer based on the expression level of the at least one target gene. In some embodiments, the subject has the skin cancer. In some embodiments, the skin cancer is cutaneous T cell lymphoma (CTCL). In some embodiments, the skin cancer treatment is a CTCL treatment.

Disclosed herein, in some embodiments, are methods of treating a subject with cutaneous T cell lymphoma (CTCL), comprising: identifying a subject suspected of having CTCL; isolating nucleic acids from a skin sample obtained from the subject by applying an adhesive patch to a skin region of the subject in a manner sufficient to adhere skin sample cells to the adhesive patch, and removing the adhesive patch from the skin sample in a manner sufficient to retain the adhered skin sample cells to the adhesive patch, wherein the skin sample cells comprise cells from the stratum corneum; detecting an expression level of at least one target gene known to be upregulated or downregulated in subjects with CTCL, by contacting the isolated nucleic acids with a set of probes that recognize the target gene, and detecting binding between the at least one target gene and the set of probes; determining whether the subject has CTCL based on the expression level of the at least one target gene; and administering a CTCL treatment to the subject when the subject is determined to have CTCL based on the expression level of the at least one target gene, and not administering the CTCL treatment to the subject when the subject is not determined to have CTCL based on the expression level of the at least one target gene.

Disclosed herein, in some embodiments, are methods of treating a subject with cutaneous T cell lymphoma (CTCL). Some embodiments include identifying a subject suspected of having CTCL. Some embodiments include obtaining a skin sample the subject by applying the adhesive patch to the subject's skin in a manner sufficient to adhere the skin sample to the adhesive patch, and removing the adhesive patch from the subject's skin in a manner sufficient to retain the skin sample adhered to the adhesive patch. Some embodiments include isolating nucleic acids from the skin sample. Some embodiments include contacting the isolated nucleic acids with a set of probes that recognize one or more genes of interest implicated in CTCL. Some embodiments include detecting or measuring the amount of binding between the genes of interest and the set of probes. Some embodiments include identifying the subject as having CTCL, or as not having CTCL, based on the amount of binding between the genes of interest and the set of probes. Some embodiments include administering a treatment for the CTCL based on the determination of whether the subject has CTCL.

Disclosed herein, in some embodiments, are methods of treating a subject with cutaneous T cell lymphoma (CTCL), comprising: identifying a subject suspected of having CTCL; obtaining a skin sample the subject by applying the adhesive patch to the subject's skin in a manner sufficient to adhere the skin sample to the adhesive patch, and removing the adhesive patch from the subject's skin in a manner sufficient to retain the skin sample adhered to the adhesive patch; isolating nucleic acids from the skin sample; contacting the isolated nucleic acids with a set of probes that recognize one or more genes of interest implicated in CTCL; detecting or measuring the amount of binding between the genes of interest and the set of probes; identifying the subject as having CTCL, or as not having CTCL, based on the amount of binding between the genes of interest and the set of probes; and administering a treatment for the CTCL based on the determination of whether the subject has CTCL.

Disclosed herein, in some embodiments, are methods of treating a subject suspected of having cutaneous T cell lymphoma (CTCL). In some embodiments, the method includes isolating nucleic acids from a skin sample adhered to an adhesive patch. In some embodiments, the skin sample has been obtained from the subject's stratum corneum. Some embodiments include contacting the isolated nucleic acids with a set of probes that recognize target genes. Some embodiments include detecting or measuring an amount of binding between the nucleic acids and the set of probes. Some embodiments include administering to the subject a treatment for CTCL when the amount of binding between the nucleic acids and the set of probes is altered in the skin sample relative to a control or threshold amount of binding. Some embodiments include determining that the subject has CTCL when the amount of binding between the nucleic acids and the set of probes in the skin sample is altered relative to the control or threshold amount of binding. In some embodiments, the amount of binding between the nucleic acids and the set of probes in the skin sample is greater than the control or threshold amount of binding. In some embodiments, the amount of binding between the nucleic acids and the set of probes in the skin sample is less than the control or threshold amount of binding.

Disclosed herein, in some embodiments, are methods of treating a subject suspected of having cutaneous T cell lymphoma (CTCL), comprising: isolating nucleic acids from a skin sample adhered to an adhesive patch, the skin sample having been obtained from the subject's stratum corneum; contacting the isolated nucleic acids with a set of probes that recognize target genes; detecting or measuring an amount of binding between the nucleic acids and the set of probes; and administering to the subject a treatment for CTCL when the amount of binding between the nucleic acids and the set of probes is altered in the skin sample relative to a control or threshold amount of binding.

Described herein, in some embodiments, are methods of treatment that include administering a skin cancer treatment such as a cutaneous T cell lymphoma (CTCL) treatment to a subject. Some embodiments include administering a CTCL treatment to the subject based on a determination of whether the subject has CTCL. In some embodiments, the CTCL treatment comprises a pharmaceutical composition. In some embodiments, the CTCL treatment comprises a steroid treatment. In some embodiments, the CTCL treatment comprises interferon treatment. In some embodiments, the CTCL treatment comprises chemotherapy. In some embodiments, the CTCL treatment comprises phototherapy. In some embodiments, the CTCL treatment comprises radiation therapy. In some embodiments, the CTCL treatment comprises a surgery. In some embodiments, the CTCL treatment comprises a transplant. In some embodiments, the CTCL treatment comprises a bone marrow transplant. In some embodiments, the CTCL treatment comprises a steroid, interferon, chemotherapy, phototherapy, radiation therapy, or a bone marrow transplant.

In some embodiments, the CTCL treatment includes administration of bexarotene to the subject. In some embodiments, the bexarotene is in a gel. In some embodiments, the CTCL treatment includes administration of mechlorethamine to the subject. In some embodiments, the mechlorethamine is in a gel. In some embodiments, the CTCL treatment includes administration of a retinoid to the subject. In some embodiments, the CTCL treatment includes administration of a corticosteroid to the subject. In some embodiments, the CTCL treatment includes administration of imiquimod to the subject. In some embodiments, the CTCL treatment includes administration of local radiation to the subject. In some embodiments, the CTCL treatment includes administration of ultraviolet light to the subject. In some embodiments, the CTCL treatment includes administration of extracorporeal photopheresis to the subject. In some embodiments, the CTCL treatment includes administration of acitretin to the subject. In some embodiments, the CTCL treatment includes administration of bexarotene to the subject. In some embodiments, the CTCL treatment includes administration of interferon to the subject. In some embodiments, the CTCL treatment includes administration of methotrexate to the subject. In some embodiments, the CTCL treatment includes administration of romidepsin to the subject. In some embodiments, the CTCL treatment includes administration of vorinostat to the subject.

Some embodiments include 1, 2, 3, 4, 5, 6, 7, 8, 9, 10, 11, 12, 13, 14, or 15, or more administrations of the skin cancer treatment. Some embodiments include a range defined by any two of 1, 2, 3, 4, 5, 6, 7, 8, 9, 10, 11, 12, 13, 14, or 15, administrations of the skin cancer treatment. Some embodiments include administration daily, weekly, biweekly, or monthly.

In some embodiments, the skin cancer treatment includes a pharmaceutical composition. In some embodiments, the pharmaceutical composition is sterile. In some embodiments, the pharmaceutical composition includes a pharmaceutically acceptable carrier. In some embodiments, the pharmaceutically acceptable carrier comprises water. In some embodiments, the pharmaceutically acceptable carrier comprises a buffer. In some embodiments, the pharmaceutically acceptable carrier comprises a saline solution. In some embodiments, the pharmaceutically acceptable carrier comprises water, a buffer, or a saline solution. In some embodiments, the composition comprises a liposome. In some embodiments, the pharmaceutically acceptable carrier comprises liposomes, lipids, nanoparticles, proteins, protein-antibody complexes, peptides, cellulose, nanogel, or a combination thereof.

In some embodiments, the skin cancer treatment results in prevention, inhibition, or reversion of the skin cancer in the subject. Some embodiments relate to use of a skin cancer treatment herein in the method of preventing, inhibiting, or reversing the skin cancer. Some embodiments relate to a method of preventing, inhibiting, or reversing a skin cancer such as cutaneous T cell lymphoma (CTCL) in a subject in need thereof. Some embodiments include administering a pharmaceutical composition to a subject with the skin cancer. In some embodiments, the administration prevents, inhibits, or reverses the skin cancer in the subject. In some embodiments, the pharmaceutical composition prevents, inhibits, or reverses the skin cancer in the subject.

Some embodiments include administering a skin cancer treatment. In some embodiments, administering comprises giving, applying or bringing the skin cancer treatment into contact with the subject. In some embodiments, administration is accomplished by any of a number of routes. In some embodiments, administration is accomplished by a topical, oral, subcutaneous, intramuscular, intraperitoneal, intravenous, intrathecal or intradermal route.

Components of the Skin Collection Kit

In some embodiments, the adhesive patch from the sample collection kit described herein comprises a first collection area comprising an adhesive matrix and a second area extending from the periphery of the first collection area. The adhesive matrix is located on a skin facing surface of the first collection area. The second area functions as a tab, suitable for applying and removing the adhesive patch. The tab is sufficient in size so that while applying the adhesive patch to a skin surface, the applicant does not come in contact with the matrix material of the first collection area. In some embodiments, the adhesive patch does not contain a second area tab. In some instances, the adhesive patch is handled with gloves to reduce contamination of the adhesive matrix prior to use.

In some embodiments, the first collection area is a polyurethane carrier film. In some embodiments, the adhesive matrix is comprised of a synthetic rubber compound. In some embodiments, the adhesive matrix is a styrene-isoprene-styrene (SIS) linear block copolymer compound. In some instances, the adhesive patch does not comprise latex, silicone, or both. In some instances, the adhesive patch is manufactured by applying an adhesive material as a liquid-solvent mixture to the first collection area and subsequently removing the solvent. In some embodiments, the adhesive matrix is configured to adhere cells from the stratum corneum of a skin sample.

The matrix material is sufficiently sticky to adhere to a skin sample. The matrix material is not so sticky that is causes scarring or bleeding or is difficult to remove. In some embodiments, the matrix material is comprised of a transparent material. In some instances, the matrix material is biocompatible. In some instances, the matrix material does not leave residue on the surface of the skin after removal. In certain instances, the matrix material is not a skin irritant.

In some embodiments, the adhesive patch comprises a flexible material, enabling the patch to conform to the shape of the skin surface upon application. In some instances, at least the first collection area is flexible. In some instances, the tab is plastic. In an illustrative example, the adhesive patch does not contain latex, silicone, or both. In some embodiments, the adhesive patch is made of a transparent material, so that the skin sampling area of the subject is visible after application of the adhesive patch to the skin surface. The transparency ensures that the adhesive patch is applied on the desired area of skin comprising the skin area to be sampled. In some embodiments, the adhesive patch is between about 5 and about 100 mm in length. In some embodiments, the first collection area is between about 5 and about 40 mm in length. In some embodiments, the first collection area is between about 10 and about 20 mm in length. In some embodiments the length of the first collection area is configured to accommodate the area of the skin surface to be sampled, including, but not limited to, about 19 mm, about 20 mm, about 21 mm, about 22 mm, about 23 mm, about 24 mm, about 25 mm, about 30 mm, about 35 mm, about 40 mm, about 45 mm, about 50 mm, about 55 mm, about 60 mm, about 65 mm, about 70 mm, about 75 mm, about 80 mm, about 85 mm, about 90 mm, and about 100 mm. In some embodiments, the first collection area is elliptical.

In further embodiments, the adhesive patch of this invention is provided on a peelable release sheet in the adhesive skin sample collection kit. In some embodiments, the adhesive patch provided on the peelable release sheet is configured to be stable at temperatures between −80° C. and 30° C. for at least 6 months, at least 1 year, at least 2 years, at least 3 years, and at least 4 years. In some instances, the peelable release sheet is a panel of a tri-fold skin sample collector.

In some instances, nucleic acids are stable on adhesive patch or patches when stored for a period of time or at a particular temperature. In some instances, the period of time is at least or about 1 day, 2 days, 3 days, 4 days, 5 days, 6 days, 7 days, 2 weeks, 3 weeks, 4 weeks, or more than 4 weeks. In some instances, the period of time is about 7 days. In some instances, the period of time is about 10 days. In some instances, the temperature is at least or about −80° C., −70° C., −60° C., −50° C., −40° C., −20° C., −10° C., −4° C., 0° C., 5° C., 15° C., 18° C., 20° C., 25° C., 30° C., 35° C., 40° C., 45° C., 50° C., or more than 50° C. The nucleic acids on the adhesive patch or patches, in some embodiments, are stored for any period of time described herein and any particular temperature described herein. For example, the nucleic acids on the adhesive patch or patches are stored for at least or about 7 days at about 25° C., 7 days at about 30° C., 7 days at about 40° C., 7 days at about 50° C., 7 days at about 60° C., or 7 days at about 70° C. In some instances, the nucleic acids on the adhesive patch or patches are stored for at least or about 10 days at about −80° C.

The peelable release sheet, in certain embodiments, is configured to hold a plurality of adhesive patches, including, but not limited to, 12, 11, 10, 9, 8, 7, 6, 5, 4, 3, 2, 1, from about 2 to about 8, from about 2 to about 7, from about 2 to about 6, from about 2 to about 4, from about 3 to about 6, from about 3 to about 8, from about 4 to about 10, from about 4 to about 8, from about 4 to about 6, from about 4 to about 5, from about 6 to about 10, from about 6 to about 8, or from about 4 to about 8. In some instances, the peelable release sheet is configured to hold about 12 adhesive patches. In some instances, the peelable release sheet is configured to hold about 11 adhesive patches. In some instances, the peelable release sheet is configured to hold about 10 adhesive patches. In some instances, the peelable release sheet is configured to hold about 9 adhesive patches. In some instances, the peelable release sheet is configured to hold about 8 adhesive patches. In some instances, the peelable release sheet is configured to hold about 7 adhesive patches. In some instances, the peelable release sheet is configured to hold about 6 adhesive patches. In some instances, the peelable release sheet is configured to hold about 5 adhesive patches. In some instances, the peelable release sheet is configured to hold about 4 adhesive patches. In some instances, the peelable release sheet is configured to hold about 3 adhesive patches. In some instances, the peelable release sheet is configured to hold about 2 adhesive patches. In some instances, the peelable release sheet is configured to hold about 1 adhesive patch.

Provided herein, in certain embodiments, are methods and compositions for obtaining a sample using an adhesive patch, wherein the adhesive patch is applied to the skin and removed from the skin. After removing the used adhesive patch from the skin surface, the patch stripping method, in some instances, further comprise storing the used patch on a placement area sheet, where the patch remains until the skin sample is isolated or otherwise utilized. In some instances, the used patch is configured to be stored on the placement area sheet for at least 1 week at temperatures between −80° C. and 30° C. In some embodiments, the used patch is configured to be stored on the placement area sheet for at least 2 weeks, at least 3 weeks, at least 1 month, at least 2 months, at least 3 months, at least 4 months, at least 5 months, and at least 6 months at temperatures between −80° C. to 30° C.

In some instances, the placement area sheet comprises a removable liner, provided that prior to storing the used patch on the placement area sheet, the removable liner is removed. In some instances, the placement area sheet is configured to hold a plurality of adhesive patches, including, but not limited to, 12, 11, 10, 9, 8, 7, 6, 5, 4, 3, 2, 1, from about 2 to about 8, from about 2 to about 7, from about 2 to about 6, from about 2 to about 4, from about 3 to about 6, from about 3 to about 8, from about 4 to about 10, from about 4 to about 8, from about 4 to about 6, from about 4 to about 5, from about 6 to about 10, from about 6 to about 8, or from about 4 to about 8. In some instances, the placement area sheet is configured to hold about 12 adhesive patches. In some instances, the placement area sheet is configured to hold about 11 adhesive patches. In some instances, the placement area sheet is configured to hold about 10 adhesive patches. In some instances, the placement area sheet is configured to hold about 9 adhesive patches. In some instances, the placement area sheet is configured to hold about 8 adhesive patches. In some instances, the placement area sheet is configured to hold about 7 adhesive patches. In some instances, the placement area sheet is configured to hold about 6 adhesive patches. In some instances, the placement area sheet is configured to hold about 5 adhesive patches. In some instances, the placement area sheet is configured to hold about 4 adhesive patches. In some instances, the placement area sheet is configured to hold about 3 adhesive patches. In some instances, the placement area sheet is configured to hold about 2 adhesive patches. In some instances, the placement area sheet is configured to hold about 1 adhesive patch.

The used patch, in some instances, is stored so that the matrix containing, skin facing surface of the used patch is in contact with the placement area sheet. In some instances, the placement area sheet is a panel of the tri-fold skin sample collector. In some instances, the tri-fold skin sample collector further comprises a clear panel. In some instances, the tri-fold skin sample collector is labeled with a unique barcode that is assigned to a subject. In some instances, the tri-fold skin sample collector comprises an area for labeling subject information.

In an illustrative embodiment, the adhesive skin sample collection kit comprises the tri-fold skin sample collector comprising adhesive patches stored on a peelable release panel. In some instances, the tri-fold skin sample collector further comprises a placement area panel with a removable liner. In some instances, the patch stripping method involves removing an adhesive patch from the tri-fold skin sample collector peelable release panel, applying the adhesive patch to a skin sample, removing the used adhesive patch containing a skin sample and placing the used patch on the placement area sheet. In some instances, the placement area panel is a single placement area panel sheet. In some instances, the identity of the skin sample collected is indexed to the tri-fold skin sample collector or placement area panel sheet by using a barcode or printing patient information on the collector or panel sheet. In some instances, the indexed tri-fold skin sample collector or placement sheet is sent to a diagnostic lab for processing. In some instances, the used patch is configured to be stored on the placement panel for at least 1 week at temperatures between −80° C. and 25° C. In some embodiments, the used patch is configured to be stored on the placement area panel for at least 2 weeks, at least 3 weeks, at least 1 month, at least 2 months, at least 3 months, at least 4 months, at least 5 months, and at least 6 months at temperatures between −80° C. and 25° C. In some embodiments, the indexed tri-fold skin sample collector or placement sheet is sent to a diagnostic lab using UPS or FedEx.

In an exemplary embodiment, the patch stripping method further comprises preparing the skin sample prior to application of the adhesive patch. Preparation of the skin sample includes, but is not limited to, removing hairs on the skin surface, cleansing the skin surface and/or drying the skin surface. In some instances, the skin surface is cleansed with an antiseptic including, but not limited to, alcohols, quaternary ammonium compounds, peroxides, chlorhexidine, halogenated phenol derivatives and quinolone derivatives. In some instances, the alcohol is about 0 to about 20%, about 20 to about 40%, about 40 to about 60%, about 60 to about 80%, or about 80 to about 100% isopropyl alcohol. In some instances, the antiseptic is 70% isopropyl alcohol.

In some embodiments, the patch stripping method is used to collect a skin sample from the surfaces including, but not limited to, the face, head, neck, arm, chest, abdomen, back, leg, hand or foot. In some instances, the skin surface is not located on a mucous membrane. In some instances, the skin surface is not ulcerated or bleeding. In certain instances, the skin surface has not been previously biopsied. In certain instances, the skin surface is not located on the soles of the feet or palms.

The patch stripping method, devices, and systems described herein are useful for the collection of a skin sample from a skin lesion. A skin lesion is a part of the skin that has an appearance or growth different from the surrounding skin. In some instances, the skin lesion is pigmented. A pigmented lesion includes, but is not limited to, a mole, dark colored skin spot and a melanin containing skin area. In some embodiments, the skin lesion is from about 5 mm to about 16 mm in diameter. In some instances, the skin lesion is from about 5 mm to about 15 mm, from about 5 mm to about 14 mm, from about 5 mm to about 13 mm, from about 5 mm to about 12 mm, from about 5 mm to about 11 mm, from about 5 mm to about 10 mm, from about 5 mm to about 9 mm, from about 5 mm to about 8 mm, from about 5 mm to about 7 mm, from about 5 mm to about 6 mm, from about 6 mm to about 15 mm, from about 7 mm to about 15 mm, from about 8 mm to about 15 mm, from about 9 mm to about 15 mm, from about 10 mm to about 15 mm, from about 11 mm to about 15 mm, from about 12 mm to about 15 mm, from about 13 mm to about 15 mm, from about 14 mm to about 15 mm, from about 6 to about 14 mm, from about 7 to about 13 mm, from about 8 to about 12 mm and from about 9 to about 11 mm in diameter. In some embodiments, the skin lesion is from about 10 mm to about 20 mm, from about 20 mm to about 30 mm, from about 30 mm to about 40 mm, from about 40 mm to about 50 mm, from about 50 mm to about 60 mm, from about 60 mm to about 70 mm, from about 70 mm to about 80 mm, from about 80 mm to about 90 mm, and from about 90 mm to about 100 mm in diameter. In some instances, the diameter is the longest diameter of the skin lesion. In some instances, the diameter is the smallest diameter of the skin lesion.

The adhesive skin sample collection kit, in some embodiments, comprises at least one adhesive patch, a sample collector, and an instruction for use sheet. In an exemplary embodiment, the sample collector is a tri-fold skin sample collector comprising a peelable release panel comprising at least one adhesive patch, a placement area panel comprising a removable liner, and a clear panel. The tri-fold skin sample collector, in some instances, further comprises a barcode and/or an area for transcribing patient information. In some instances, the adhesive skin sample collection kit is configured to include a plurality of adhesive patches, including but not limited to 12, 11, 10, 9, 8, 7, 6, 5, 4, 3, 2, 1, from about 2 to about 8, from about 2 to about 7, from about 2 to about 6, from about 2 to about 4, from about 3 to about 6, from about 3 to about 8, from about 4 to about 10, from about 4 to about 8, from about 4 to about 6, from about 4 to about 5, from about 6 to about 10, from about 6 to about 8, or from about 4 to about 8. The instructions for use sheet provide the kit operator all of the necessary information for carrying out the patch stripping method. The instructions for use sheet preferably include diagrams to illustrate the patch stripping method.

In some instances, the adhesive skin sample collection kit provides all the necessary components for performing the patch stripping method. In some embodiments, the adhesive skin sample collection kit includes a lab requisition form for providing patient information. In some instances, the kit further comprises accessory components. Accessory components include, but are not limited to, a marker, a resealable plastic bag, gloves and a cleansing reagent. The cleansing reagent includes, but is not limited to, an antiseptic such as isopropyl alcohol. In some instances, the components of the skin sample collection kit are provided in a cardboard box.

In some embodiments, the kit includes a skin collection device. In some embodiments, the skin collection device includes a non-invasive skin collection device. In some embodiments, the skin collection device includes an adhesive patch as described herein. In some embodiments, the skin collection device includes a brush. In some embodiments, the skin collection device includes a swab. In some embodiments, the skin collection device includes a probe. In some embodiments, the skin collection device includes a medical applicator. In some embodiments, the skin collection device includes a scraper. In some embodiments, the skin collection device includes an invasive skin collection device such as a needle or scalpel. In some embodiments, the skin collection device includes a needle. In some embodiments, the skin collection device includes a microneedle. In some embodiments, the skin collection device includes a hook.

Disclosed herein, in some embodiments, are kits for determining the presence of cutaneous T cell lymphoma (CTCL) in a skin sample. In some embodiments, the kit includes an adhesive patch. In some embodiments, the adhesive patch comprises an adhesive matrix configured to adhere skin sample cells from the stratum corneum of a subject. Some embodiments include a nucleic acid isolation reagent. Some embodiments include a plurality of probes that recognize at least one target gene. In some embodiments, the at least one target gene is known to be upregulated or downregulated in subjects with CTCL. Disclosed herein, in some embodiments, are kits for determining the presence of cutaneous T cell lymphoma (CTCL) in a skin sample, comprising: an adhesive patch comprising an adhesive matrix configured to adhere skin sample cells from the stratum corneum of a subject; a nucleic acid isolation reagent; and a plurality of probes that recognize at least one target gene known to be upregulated or downregulated in subjects with CTCL.

Examples of subjects include but are not limited to vertebrates, animals, mammals, dogs, cats, cattle, rodents, mice, rats, primates, monkeys, and humans. In some embodiments, the subject is a vertebrate. In some embodiments, the subject is an animal. In some embodiments, the subject is a mammal. In some embodiments, the subject is an animal, a mammal, a dog, a cat, cattle, a rodent, a mouse, a rat, a primate, or a monkey. In some embodiments, the subject is a human. In some embodiments, the subject is male. In some embodiments, the subject is female. In some embodiments, the subject has CTCL. In some embodiments, the CTCL comprises mycosis fungoides. In some embodiments, the CTCL comprises Sézary syndrome.

Cellular Material and Sample Process

In some embodiments of the methods described herein, a skin sample is obtained from the subject by applying an adhesive patch to a skin region of the subject. In some embodiments, the skin sample is obtained using an adhesive patch. In some embodiments, the adhesive patch comprises tape. In some embodiments, the skin sample is not obtained with an adhesive patch. In some instances, the skin sample is obtained using a brush. In some instances, the skin sample is obtained using a swab, for example a cotton swab. In some cases, the skin sample is obtained using a probe. In some cases, the skin sample is obtained using a hook. In some instances, the skin sample is obtained using a medical applicator. In some instances, the skin sample is obtained by scraping a skin surface of the subject. In some cases, the skin sample is obtained through excision. In some instances, the skin sample is biopsied. In some embodiments, the skin sample is a biopsy. In some instances, the skin sample is obtained using one or more needles. For example, the needles may be microneedles. In some instances, the biopsy is a needle biopsy, or a microneedle biopsy. In some instances, the skin sample is obtained invasively. In some instances, the skin sample is obtained non-invasively.

In some embodiments, the skin sample comprises cells of the stratum corneum. In some embodiments, the skin sample consists of cells of the stratum corneum. In some embodiments, the skin sample does not include the basal layer of the skin. In some embodiments, the skin sample comprises or consists of a skin depth of 10 μm, 50 μm, 100 μm, 150 μm, 200 μm, 250 μm, 300 μm, 350 μm, 400 μm, 450 μm, 500 μm, or a range of skin depths defined by any two of the aforementioned skin depths. In some embodiments, the skin sample comprises or consists of a skin depth of 50-100 μm. In some embodiments, the skin sample comprises or consists of a skin depth of 100-200 μm. In some embodiments, the skin sample comprises or consists of a skin depth of 200–300 μm. In some embodiments, the skin sample comprises or consists of a skin depth of 300-400 μm. In some embodiments, the skin sample comprises or consists of a skin depth of 400-500 μm.

In some embodiments, the skin sample is no more than 10 μm thick. In some embodiments, the skin sample is no more than 50 μm thick. In some embodiments, the skin sample is no more than 100 μm thick. In some embodiments, the skin sample is no more than 150 μm thick. In some embodiments, the skin sample is no more than 200 μm thick. In some embodiments, the skin sample is no more than 250 μm thick. In some embodiments, the skin sample is no more than 300 μm thick. In some embodiments, the skin sample is no more than 350 μm thick. In some embodiments, the skin sample is no more than 400 μm thick. In some embodiments, the skin sample is no more than 450 μm thick. In some embodiments, the skin sample is no more than 500 μm thick.

In some embodiments, the skin sample is at least 10 μm thick. In some embodiments, the skin sample is at least 50 μm thick. In some embodiments, the skin sample is at least 100 μm thick. In some embodiments, the skin sample is at least 150 μm thick. In some embodiments, the skin sample is at least 200 μm thick. In some embodiments, the skin sample is at least 250 μm thick. In some embodiments, the skin sample is at least 300 μm thick. In some embodiments, the skin sample is at least 350 μm thick. In some embodiments, the skin sample is at least 400 μm thick. In some embodiments, the skin sample is at least 450 μm thick. In some embodiments, the skin sample is at least 500 μm thick.

In some embodiments, the adhesive patch removes a skin sample from the subject at a depth no greater than 10 μm. In some embodiments, the adhesive patch removes a skin sample from the subject at a depth no greater than 50 μm. In some embodiments, the adhesive patch removes a skin sample from the subject at a depth no greater than 100 μm. In some embodiments, the adhesive patch removes a skin sample from the subject at a depth no greater than 150 μm. In some embodiments, the adhesive patch removes a skin sample from the subject at a depth no greater than 200 μm. In some embodiments, the adhesive patch removes a skin sample from the subject at a depth no greater than 250 μm. In some embodiments, the adhesive patch removes a skin sample from the subject at a depth no greater than 300 μm. In some embodiments, the adhesive patch removes a skin sample from the subject at a depth no greater than 350 μm. In some embodiments, the adhesive patch removes a skin sample from the subject at a depth no greater than 400 µm. In some embodiments, the adhesive patch removes a skin sample from the subject at a depth no greater than 450 µm. In some embodiments, the adhesive patch removes a skin sample from the subject at a depth no greater than 500 µm.

In some embodiments, the adhesive patch removes 1, 2, 3, 4, or 5 layers of stratum corneum from a skin surface of the subject. In some embodiments, the adhesive patch removes a range of layers of stratum corneum from a skin surface of the subject, for example a range defined by any two of the following integers: 1, 2, 3, 4, or 5. In some embodiments, the adhesive patch removes 1-5 layers of stratum corneum from a skin surface of the subject. In some embodiments, the adhesive patch removes 2-3 layers of stratum corneum from a skin surface of the subject. In some embodiments, the adhesive patch removes 2-4 layers of stratum corneum from a skin surface of the subject. In some embodiments, the adhesive patch removes no more than the basal layer of a skin surface from the subject.

The methods and devices provided herein, in certain embodiments, involve applying an adhesive or other similar patch to the skin in a manner so that an effective or sufficient amount of a tissue, such as a skin sample, adheres to the adhesive matrix of the adhesive patch. In some cases, the skin sample adhered to the adhesive matrix comprises or consists of cells from the stratum corneum of a subject. For example, the effective or sufficient amount of a skin sample is an amount that removably adheres to a material, such as the matrix or adhesive patch. The adhered skin sample, in certain embodiments, comprises cellular material including nucleic acids. In some instances, the nucleic acid is RNA or DNA. An effective amount of a skin sample contains an amount of cellular material sufficient for performing a diagnostic assay. In some instances, the diagnostic assay is performed using the cellular material isolated from the adhered skin sample on the used adhesive patch. In some instances, the diagnostic assay is performed on the cellular material adhered to the used adhesive patch. In some embodiments, an effect amount of a skin sample comprises an amount of RNA sufficient to perform a gene expression analysis. Sufficient amounts of RNA includes, but not limited to, picogram, nanogram, and microgram quantities. In some embodiments, the RNA includes mRNA. In some embodiments, the RNA includes microRNAs. In some embodiments, the RNA includes mRNA and microRNAs. In some embodiments, an effect amount of a skin sample comprises an amount of DNA sufficient to perform a gene expression analysis. Sufficient amounts of DNA includes, but not limited to, picogram, nanogram, and microgram quantities. In some embodiments, an effect amount of a skin sample comprises an amount of DNA and RNA sufficient to perform a gene expression analysis. Sufficient amounts of DNA and RNA includes, but not limited to, picogram, nanogram, and microgram quantities of the DNA and RNA.

Some embodiments include collecting cells from the stratum corneum of a subject, for instance, by using an adhesive tape with an adhesive matrix to adhere the cells from the stratum corneum to the adhesive matrix. In some embodiments, the cells from the stratum corneum comprise T cells or components of T cells. In some embodiments, the cells from the stratum corneum comprise keratinocytes. In some embodiments, the skin sample does not comprise melanocytes. In some embodiments, a skin sample is obtained by applying a plurality of adhesive patches to a skin region of a subject in a manner sufficient to adhere skin sample cells to each of the adhesive patches, and removing each of the plurality of adhesive patches from the skin region in a manner sufficient to retain the adhered skin sample cells to each of the adhesive patches. In some embodiments, the skin region comprises a skin lesion.

In some instances, the nucleic acid is a RNA molecule or a fragmented RNA molecule (RNA fragments). In some instances, the RNA is a microRNA (miRNA), a pre-miRNA, a pri-miRNA, a mRNA, a pre-mRNA, a viral RNA, a viroid RNA, a virusoid RNA, circular RNA (circRNA), a ribosomal RNA (rRNA), a transfer RNA (tRNA), a pre-tRNA, a long non-coding RNA (lncRNA), a small nuclear RNA (snRNA), a circulating RNA, a cell-free RNA, an exosomal RNA, a vector-expressed RNA, a RNA transcript, a synthetic RNA, or combinations thereof. In some instances, the RNA is mRNA. In some instances, the RNA is cell-free circulating RNA.

In some instances, the nucleic acid is DNA. DNA includes, but not limited to, genomic DNA, viral DNA, mitochondrial DNA, plasmid DNA, amplified DNA, circular DNA, circulating DNA, cell-free DNA, or exosomal DNA. In some instances, the DNA is single-stranded DNA (ssDNA), double-stranded DNA, denaturing double-stranded DNA, synthetic DNA, and combinations thereof. In some instances, the DNA is genomic DNA. In some instances, the DNA is cell-free circulating DNA.

In additional embodiments, the adhered skin sample comprises cellular material including nucleic acids such as RNA or DNA, in an amount that is at least about 1 picogram. In some embodiments, the amount of cellular material is no more than about 1 nanogram. In further or additional embodiments, the amount of cellular material is no more than about 1 microgram. In still further or additional embodiments, the amount of cellular material is no more than about 1 gram.

In further or additional embodiments, the amount of cellular material is from about 1 picogram to about 1 gram. In further or additional embodiments, the cellular material comprises an amount that is from about 50 microgram to about 1 gram, from about 100 picograms to about 500 micrograms, from about 500 picograms to about 100 micrograms, from about 750 picograms to about 1 microgram, from about 1 nanogram to about 750 nanograms, or from about 1 nanogram to about 500 nanograms.

In further or additional embodiments, the amount of cellular material, including nucleic acids such as RNA or DNA, comprises an amount that is from about 50 microgram to about 500 microgram, from about 100 microgram to about 450 microgram, from about 100 microgram to about 350 microgram, from about 100 microgram to about 300 microgram, from about 120 microgram to about 250 microgram, from about 150 microgram to about 200 microgram, from about 500 nanograms to about 5 nanograms, or from about 400 nanograms to about 10 nanograms, or from about 200 nanograms to about 15 nanograms, or from about 100 nanograms to about 20 nanograms, or from about 50 nanograms to about 10 nanograms, or from about 50 nanograms to about 25 nanograms.

In further or additional embodiments, the amount of cellular material, including nucleic acids such as RNA or DNA, is less than about 1 gram, is less than about 500 micrograms, is less than about 490 micrograms, is less than about 480 micrograms, is less than about 470 micrograms, is less than about 460 micrograms, is less than about 450 micrograms, is less than about 440 micrograms, is less than about 430 micrograms, is less than about 420 micrograms, is less than about 410 micrograms, is less than about 400 micrograms, is less than about 390 micrograms, is less than about 380 micrograms, is less than about 370 micrograms, is less than about 360 micrograms, is less than about 350 micrograms, is less than about 340 micrograms, is less than about 330 micrograms, is less than about 320 micrograms, is less than about 310 micrograms, is less than about 300 micrograms, is less than about 290 micrograms, is less than about 280 micrograms, is less than about 270 micrograms, is less than about 260 micrograms, is less than about 250 micrograms, is less than about 240 micrograms, is less than about 230 micrograms, is less than about 220 micrograms, is less than about 210 micrograms, is less than about 200 micrograms, is less than about 190 micrograms, is less than about 180 micrograms, is less than about 170 micrograms, is less than about 160 micrograms, is less than about 150 micrograms, is less than about 140 micrograms, is less than about 130 micrograms, is less than about 120 micrograms, is less than about 110 micrograms, is less than about 100 micrograms, is less than about 90 micrograms, is less than about 80 micrograms, is less than about 70 micrograms, is less than about 60 micrograms, is less than about 50 micrograms, is less than about 20 micrograms, is less than about 10 micrograms, is less than about 5 micrograms, is less than about 1 microgram, is less than about 750 nanograms, is less than about 500 nanograms, is less than about 250 nanograms, is less than about 150 nanograms, is less than about 100 nanograms, is less than about 50 nanograms, is less than about 25 nanograms, is less than about 15 nanograms, is less than about 1 nanogram, is less than about 750 picograms, is less than about 500 picograms, is less than about 250 picograms, is less than about 100 picograms, is less than about 50 picograms, is less than about 25 picograms, is less than about 15 picograms, or is less than about 1 picogram.

In some embodiments, isolated RNA from a collected skin sample is reverse transcribed into cDNA, for example for amplification by PCR to enrich for target genes. The expression levels of these target genes are quantified by quantitative PCR in a gene expression test. In some instances, in combination with quantitative PCR, a software program performed on a computer is utilized to quantify RNA isolated from the collected skin sample. In some instances, a software program or module is utilized to relate a quantity of RNA from a skin sample to a gene expression signature, wherein the gene expression signature is associated with a disease such as skin cancer. In some embodiments, a software program or module scores a sample based on gene expression levels. In some embodiments, the sample score is compared with a reference sample score to determine if there is a statistical significance between the gene expression signature and a disease.

In some instances, the layers of skin include epidermis, dermis, or hypodermis. The outer layer of epidermis is the stratum corneum layer, followed by stratum lucidum, stratum granulosum, stratum spinosum, and stratum basale. In some instances, the skin sample is obtained from the epidermis layer. In some cases, the skin sample is obtained from the stratum corneum layer. In some instances, the skin sample is obtained from the dermis.

In some instances, cells from the stratum corneum layer are obtained, which comprises keratinocytes. In some instances, cells from the stratum corneum layer comprise T cells or components of T cells. In some cases, melanocytes are not obtained from the skin sample.

Following extraction of nucleic acids from a biological sample, the nucleic acids, in some instances, are further purified. In some instances, the nucleic acids are RNA. In some instances, the nucleic acids are DNA. In some instances, the RNA is human RNA. In some instances, the DNA is human DNA. In some instances, the RNA is microbial RNA. In some instances, the DNA is microbial DNA. In some instances, human nucleic acids and microbial nucleic acids are purified from the same biological sample. In some instances, nucleic acids are purified using a column or resin based nucleic acid purification scheme. In some instances, this technique utilizes a support comprising a surface area for binding the nucleic acids. In some instances, the support is made of glass, silica, latex or a polymeric material. In some instances, the support comprises spherical beads.

Methods for isolating nucleic acids, in certain embodiments, comprise using spherical beads. In some instances, the beads comprise material for isolation of nucleic acids. Exemplary material for isolation of nucleic acids using beads include, but not limited to, glass, silica, latex, and a polymeric material. In some instances, the beads are magnetic. In some instances, the beads are silica coated. In some instances, the beads are silica-coated magnetic beads. In some instances, a diameter of the spherical bead is at least or about 0.5 um, 1 um, 1.5 um, 2 um, 2.5 um, 3 um, 3.5 um, 4 um, 4.5 um, 5 um, 5.5 um, 6 um, 6.5 um, 7 um, 7.5 um, 8 um, 8.5 um, 9 um, 9.5 um, 10 um, or more than 10 um.

In some cases, a yield of the nucleic acids products obtained using methods described herein is about 500 picograms or higher, about 600 picograms or higher, about 1000 picograms or higher, about 2000 picograms or higher, about 3000 picograms or higher, about 4000 picograms or higher, about 5000 picograms or higher, about 6000 picograms or higher, about 7000 picograms or higher, about 8000 picograms or higher, about 9000 picograms or higher, about 10000 picograms or higher, about 20000 picograms or higher, about 30000 picograms or higher, about 40000 picograms or higher, about 50000 picograms or higher, about 60000 picograms or higher, about 70000 picograms or higher, about 80000 picograms or higher, about 90000 picograms or higher, or about 100000 picograms or higher.

In some cases, a yield of the nucleic acids products obtained using methods described herein is about 100 picograms, 500 picograms, 600 picograms, 700 picograms, 800 picograms, 900 picograms, 1 nanogram, 5 nanograms, 10 nanograms, 15 nanograms, 20 nanograms, 21 nanograms, 22 nanograms, 23 nanograms, 24 nanograms, 25 nanograms, 26 nanograms, 27 nanograms, 28 nanograms, 29 nanograms, 30 nanograms, 35 nanograms, 40 nanograms, 50 nanograms, 60 nanograms, 70 nanograms, 80 nanograms, 90 nanograms, 100 nanograms, 500 nanograms, or higher.

In some cases, methods described herein provide less than less than 10%, less than 8%, less than 5%, less than 2%, less than 1%, or less than 0.5% product yield variations between samples.

In some cases, methods described herein provide a substantially homogenous population of a nucleic acid product.

In some cases, methods described herein provide less than 30%, less than 25%, less than 20%, less than 15%, less than 10%, less than 8%, less than 5%, less than 2%, less than 1%, or less than 0.5% contaminants.

In some instances, following extraction, nucleic acids are stored. In some instances, the nucleic acids are stored in water, Tris buffer, or Tris-EDTA buffer before subsequent analysis. In some instances, this storage is less than 8° C. In some instances, this storage is less than 4° C. In certain embodiments, this storage is less than 0° C. In some instances, this storage is less than −20° C. In certain embodiments, this storage is less than −70° C. In some instances, the nucleic acids are stored for about 1, 2, 3, 4, 5, 6, or 7 days. In some instances, the nucleic acids are stored for about 1, 2, 3, or 4 weeks. In some instances, the nucleic acids are stored for about 1, 2, 3, 4, 5, 6, 7, 8, 9, 10, 11, or 12 months.

In some instances, nucleic acids isolated using methods described herein are subjected to an amplification reaction following isolation and purification. In some instances, the nucleic acids to be amplified are RNA including, but not limited to, human RNA and human microbial RNA. In some instances, the nucleic acids to be amplified are DNA including, but not limited to, human DNA and human microbial DNA. Non-limiting amplification reactions include, but are not limited to, quantitative PCR (qPCR), self-sustained sequence replication, transcriptional amplification system, Q-Beta Replicase, rolling circle replication, or any other nucleic acid amplification known in the art. In some instances, the amplification reaction is PCR. In some instances, the amplification reaction is quantitative such as qPCR.

Provided herein are methods for detecting an expression level of one or more genes of interest from nucleic acids isolated from a biological sample. In some instances, the expression level is detected following an amplification reaction. In some instances, the nucleic acids are RNA. In some instances, the RNA is human RNA. In some instances, the RNA is microbial RNA. In some instances, the nucleic acids are DNA. In some instances, the DNA is human DNA. In some instances, the DNA is microbial DNA. In some instances, the expression level is determined using PCR. In some instances, the expression level is determined using qPCR. In some instances, the expression level is determined using a microarray. In some instances, the expression level is determined by sequencing.

Some embodiments include measuring a microRNA. In some embodiments, the measurement includes use of a stem-loop primer. Some embodiments include the use of poly-A tailing. Some embodiments include a pre-amplification of microRNAs.

Provided herein are methods and compositions for detecting a mutational change of one or more genes of interest from nucleic acids isolated from a biological sample. In some instances, the mutational change is detected following an amplification reaction. In some instances, the nucleic acids are RNA. In some instances, the nucleic acids are DNA. In some instances, the mutational change is detected using allele specific PCR. In some instances, the mutational change is detected using sequencing. In some instances, the sequencing is performed using the Sanger sequencing method. In some instances, the sequencing involves the use of chain terminating dideoxynucleotides. In some instances, the sequencing involves gel-electrophoresis. In some instances, the sequencing is performed using a next generation sequencing method. In some instances, sequencing includes, but not limited to, single-molecule real-time (SMRT) sequencing, Polony sequencing, sequencing by synthesis, sequencing by ligation, reversible terminator sequencing, proton detection sequencing, ion semiconductor sequencing, nanopore sequencing, electronic sequencing, pyrosequencing, Maxam-Gilbert sequencing, chain termination sequencing, +S sequencing, and sequencing by synthesis.

In some embodiments, the target gene mutation is detected using PCR. In some embodiments, the target gene mutation is detected using qPCR. In some embodiments, the target gene mutation is detected using sequencing. In some embodiments, the target gene mutation is detected using next generation sequencing. In some embodiments, the target gene mutation is detected using Sanger sequencing. In some embodiments, the target gene mutation is detected using an array. In some embodiments, the target gene mutation is detected using a mass spectrometry. In some embodiments, the target gene mutation is detected using a MassArray.

In some embodiments, the MassArray comprises mass spectrometry. In some embodiments, the MassArray includes DNA ionization, RNA separation, RNA detection, and/or an analysis of the detected RNAs. Some embodiments include a workflow including multiplex PCR, a mutant-specific extension protocol, and/or a MassArray analysis, followed by data analysis.

Certain Terminologies

Unless defined otherwise, all technical and scientific terms used herein have the same meaning as is commonly understood by one of skill in the art to which the claimed subject matter belongs. It is to be understood that the detailed description are exemplary and explanatory only and are not restrictive of any subject matter claimed. In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

FYN binding protein (FYB), also known as tyrosine-protein kinase FYN, Src-like kinase, tyrosine kinase P59fyn (T), or Src/Yes-related Novel, encodes a member of the protein-tyrosine kinase oncogene family. In some instances, FYB has National Center for Biotechnology Information (NCBI) Gene ID: 2534.

IL2 inducible T-cell kinase (ITK), also known as T-cell-specific kinase, tyrosine-protein kinase LYK, or IL2-inducible T-cell kinase, encodes an intracellular tyrosine kinase expressed in T-cells. In some instances, ITK has NCBI Gene ID: 3702.

Interleukin 26 (IL26) is also known as AK155 or protein AK155. In some instances, IL26 has NCBI Gene ID: 55801.

Signal transducer and activator of transcription 5A (STAT5A), also known as epididymis secretory sperm binding protein, encodes a member of the STAT family of transcription factors. In some instances, STAT5A has NCBI Gene ID: 6776.

TRAF3 interacting protein 3 (TRAF3IP3), also known as TNF receptor associated factor 3, RING-type E3 ubiquitin transferase TRAF3, CD40 receptor associated factor 1, or T3JAM, encodes a member of the TNF receptor associated factor protein family. In some instances, TRAF3IP3 has NCBI Gene ID: 80342.

Granulysin (GNLY), also known as T-lymphocyte activation gene 519 or lymphokine LAG-2, encodes a member of the saposin-like protein family. In some instances, GNLY has NCBI Gene ID: 10578.

Dynamin 3 (DNM3), also known as T-dynamin, encodes a member of a family of guanosine triphosphate (GTP)-binding proteins. In some instances, DNM3 has Gene ID: 26052.

Tumor necrosis factor superfamily member 11 (TNFSF11), also known as osteoclast differentiation factor or osteoprotegerin ligand, encodes a member of TNF cytokine family of proteins. In some instances, TNFSF11 has NCBI Gene ID: 8600.

Thymocyte selection associated high mobility group box (TOX), also known as thymus high mobility group box protein TOX, encodes a protein containing a HMG box DNA binding domain. In some instances, TOX has NCBI Gene ID: 9760.

Lymphoid enhancer binding factor 1 (LEF1), also known as T cell-specific transcription factor 1-alpha or TCF7L3, encodes a transcription factor protein. In some instances, LEF1 has NCBI Gene ID: 51176.

C-C motif chemokine receptor 4 (CCR4), also known as CMKBR4, encodes a member of the G-protein-coupled receptor family. In some instances, CCR4 has NCBI Gene ID: 1233.

POU class 2 associating factor 1 (POU2AF1), also known as B-cell-specific coactivator OBG-1, OCT-Binding factor 1, BOB-1, or OCA-B, is a protein coding gene. In some instances, POU2AF1 has NCBI Gene ID: 5450.

Gametocyte specific factor 1 (GTSF1), also known as family with sequence similarity 112, member B or FAM112B, encodes a protein involved in spermatogenesis. In some instances, GTSF1 has NCBI Gene ID: 121355.

Plastin 3 (PLS3), also known as T-Plastin, T fimbrin, or BMND18, encodes a family of the actin-binding proteins. In some instances, PLS3 has NCBI Gene ID: 5358.

Matrix metallopeptidase 12 (MMP12), also known as HME or macrophage elastase, encodes a member of the peptidase M10 family of matrix metalloproteinases. In some instances, WP12 has NCBI Gene ID: 4321.

LCK proto-oncogene, Src family tyrosine kinase (LCK), also known as lymphocyte cell-specific protein-tyrosine kinase, T cell=specific protein-tyrosine kinase, or protein YT16, encodes a member of the Src family of protein tyrosine kinases. In some instances, LCK has NCBI Gene ID: 3932.

Neural precursor cell expressed, developmentally down-regulated (NEDD4L), also known as 4-like, E3 ubiquitin protein ligase, HECT-type E3 ubiquitin transferase NED4L, or NEDD4.2, encodes a member of the Nedd4 family of HECT domain E3 ubiquitin ligases. In some instances, NEDD4L has NCBI Gene ID: 23327.

NUMBERED EMBODIMENTS

Disclosed herein, in some embodiments, are the following:

1. A method of detecting gene expression level of FYN binding protein (FYB), IL2 inducible T-cell kinase (ITK), interleukin 26 (IL26), signal transducer and activator of transcription 5A (STAT5A), TRAF3 interacting protein 3 (TRAF3IP3), granulysin (GNLY), dynamin 3 (DNM3), tumor necrosis factor superfamily member 11 (TNFSF11), or a combination thereof in a subject in need thereof, comprising:
   a) isolating nucleic acids from a skin sample obtained from the subject, wherein the skin sample comprises cells from the stratum corneum; and
   b) detecting the expression levels of FYB, ITK, IL26, STAT5A, TRAF3IP3, GNLY, DNM3, TNFSF11, or a combination thereof, by contacting the isolated nucleic acids with a set of probes that recognizes FYB, ITK, IL26, STAT5A, TRAF3IP3, GNLY, DNM3, TNFSF11, or a combination thereof, and detects binding between FYB, ITK, IL26, STAT5A, TRAF3IP3, GNLY, DNM3, TNFSF11, or a combination thereof and the set of probes.
2. The method of embodiment 1, wherein the method comprises detecting the expression levels of ITK, STAT5A, and TNFSF11.
3. The method of embodiment 1, wherein the method comprises detecting the expression levels of ITK, IL26, STAT5A, and TNFSF11.
4. The method of embodiment 1, wherein the method comprises detecting the expression levels of FYB, ITK, IL26, STAT5A, and TNFSF11.
5. The method of embodiment 1, wherein the method comprises detecting the expression levels of FYB, ITK, IL26, STAT5A, TRAF3IP3, and TNFSF11.
6. The method of embodiment 1, wherein the method comprises detecting the expression levels of FYB, ITK, IL26, STAT5A, TRAF3IP3, DNM3, and TNFSF11.
7. The method of embodiment 1, wherein the method comprises detecting the expression levels of FYB, ITK, IL26, STAT5A, TRAF3IP3, GNLY, DNM3, and TNFSF11.
8. The method of any one of the embodiments 1-7, wherein the expression level is an elevated gene expression level, compared to a gene expression level of an equivalent gene from a control sample.
9. The method of embodiment 8, wherein the gene expression level of FYB, ITK, IL26, STAT5A, TRAF3IP3, DNM3, TNFSF11, or a combination thereof is elevated.
10. The method of any one of the embodiments 1-7, wherein the expression level is a down-regulated gene expression level, compared to a gene expression level of an equivalent gene from a control sample.
11. The method of embodiment 10, wherein the gene expression level of GNLY is down-regulated.
12. The method of embodiment 1, wherein the set of probes recognizes at least one but no more than eight genes.
13. The method of embodiment 1, further comprising detecting the expression levels of TOX, LEF1, CCR4, POU2AF1, GTSF1, PLS3, MMP12, LCK, NEDD4L, or a combination thereof.
14. The method of embodiment 13, wherein the detecting comprises contacting the isolated nucleic acids with an additional set of probes that recognizes TOX, LEF1, CCR4, POU2AF1, GTSF1, PLS3, MMP12, LCK, NEDD4L, or a combination thereof, and detects binding between TOX, LEF1, CCR4, POU2AF1, GTSF1, PLS3, MMP12, LCK, NEDD4L, or a combination thereof and the additional set of probes.

15. The method of embodiment 14, wherein the additional set of probes recognizes one but no more than nine genes.

16. A method of detecting gene expression levels from a first gene classifier and a second gene classifier in a subject in need thereof, comprising:
    a) isolating nucleic acids from a skin sample obtained from the subject, wherein the skin sample comprises cells from the stratum corneum;
    b) detecting the expression levels of one or more genes from the first gene classifier: FYB, ITK, IL26, STAT5A, TRAF3IP3, GNLY, DNM3, and TNFSF11, by contacting the isolated nucleic acids with a set of probes that recognizes one or more genes from the first gene classifier, and detects binding between one or more genes from the first gene classifier and the set of probes; and
    c) detecting the expression levels of one or more genes from the second gene classifier: TOX, LEF1, CCR4, POU2AF1, GTSF1, PLS3, MMP12, LCK, and NEDD4L, by contacting the isolated nucleic acids with an additional set of probes that recognizes one or more genes from the second gene classifier, and detects binding between one or more genes from the second gene classifier and the additional set of probes.

17. The method of embodiment 16, wherein the method comprises detecting the expression levels of ITK, STAT5A, and TNFSF11 from the first gene classifier.

18. The method of embodiment 16, wherein the method comprises detecting the expression levels of ITK, IL26, STAT5A, and TNFSF11 from the first gene classifier.

19. The method of embodiment 16, wherein the method comprises detecting the expression levels of FYB, ITK, IL26, STAT5A, and TNFSF11 from the first gene classifier.

20. The method of embodiment 16, wherein the method comprises detecting the expression levels of FYB, ITK, IL26, STAT5A, TRAF3IP3, and TNFSF11 from the first gene classifier.

21. The method of embodiment 16, wherein the method comprises detecting the expression levels of FYB, ITK, IL26, STAT5A, TRAF3IP3, DNM3, and TNFSF11 from the first gene classifier.

22. The method of embodiment 16, wherein the method comprises detecting the expression levels of FYB, ITK, IL26, STAT5A, TRAF3IP3, GNLY, DNM3, and TNFSF11 from the first gene classifier.

23. The method of any one of the embodiments 16-22, wherein the expression level is an elevated gene expression level, compared to a gene expression level of an equivalent gene from a control sample.

24. The method of embodiment 23, wherein the gene expression level of FYB, ITK, IL26, STAT5A, TRAF3IP3, DNM3, TNFSF11, or a combination thereof is elevated.

25. The method of any one of the embodiments 16-22, wherein the expression level is a down-regulated gene expression level, compared to a gene expression level of an equivalent gene from a control sample.

26. The method of embodiment 25, wherein the gene expression level of GNLY is down-regulated.

27. The method of embodiment 16, wherein the set of probes recognizes at least one but no more than eight genes.

28. The method of embodiment 16, wherein the additional set of probes recognizes one but no more than nine genes.

29. The method of any one of the embodiments 1-28, wherein the nucleic acids comprise RNA, DNA, or a combination thereof 30. The method of embodiment 29, wherein the RNA is mRNA.

31. The method of embodiment 29, wherein the RNA is cell-free circulating RNA.

32. The method of any one of the embodiments 1-31, wherein the cells from the stratum corneum comprises T cells or components of T cells.

33. The method of any one of the embodiments 1-31, wherein the cells from the stratum corneum comprises keratinocytes.

34. The method of any one of the embodiments 1-33, wherein the skin sample does not comprise melanocytes.

35. The method of any one of the embodiments 1-34, wherein the skin sample is obtained by applying an adhesive patch to a skin region of the subject in a manner sufficient to adhere cells to the adhesive patch, and removing the adhesive patch from the skin region in a manner sufficient to retain the adhered cells to the adhesive patch.

36. The method of any one of the embodiments 1-34, wherein the skin sample is obtained by applying a plurality of adhesive patches to a skin region of the subject in a manner sufficient to adhere cells to each of the adhesive patches, and removing each of the adhesive patches from the skin region in a manner sufficient to retain the adhered cells to each of the adhesive patches.

37. The method of embodiment 36, wherein the plurality of adhesive patches comprises at least 4 adhesive patches.

38. The method of embodiment 35 or 36, wherein the skin region is a skin lesion region.

39. The method of any one of the embodiments 1-38, wherein the subject is suspected of having cutaneous T cell lymphoma (CTCL).

40. The method of any one of the embodiments 1-39, wherein the subject is suspected of having mycosis fungoides (MF).

41. The method of any one of the embodiments 1-39, wherein the subject is suspected of having Sézary syndrome (SS).

42. The method of any of the preceding embodiments, wherein the subject is a human.

43. A method of determining the presence of cutaneous T cell lymphoma (CTCL) in a skin sample, comprising:
    a) identifying a subject suspected of having CTCL;
    b) isolating nucleic acids from a skin sample obtained from the subject by applying an adhesive patch to a skin region of the subject in a manner sufficient to adhere skin sample cells to the adhesive patch, and removing the adhesive patch from the skin sample in a manner sufficient to retain the adhered skin sample cells to the adhesive patch, wherein the skin sample cells comprise cells from the stratum corneum; and
    c) detecting an expression level of at least one target gene known to be upregulated or downregulated in subjects with CTCL, by contacting the isolated nucleic acids with a set of probes that recognize the target gene, and detecting binding between the at least one target gene and the set of probes.

44. The method of claim 43, wherein the nucleic acids comprise mRNA.

45. The method of claim 43 or 44, wherein the cells from the stratum corneum comprise T cells or components of T cells.

46. The method of any one of claims 43-45, wherein the cells from the stratum corneum comprise keratinocytes.

47. The method of any one of claims 43-46, wherein the skin sample does not comprise melanocytes.

48. The method of any one of claims 43-47, wherein the skin sample is obtained by applying a plurality of adhesive patches to the skin region of the subject in a manner sufficient to adhere skin sample cells to each of the adhesive patches, and removing each of the plurality of adhesive patches from the skin region in a manner sufficient to retain the adhered skin sample cells to each of the adhesive patches.

49. The method of any one of claims 43-48, wherein the skin region comprises a skin lesion.

50. The method of any one of claims 43-49, further comprising determining whether the subject has CTCL based on the expression level of the at least one target gene.

51. The method of any one of claims 43-50, further comprising administering a CTCL treatment to the subject based on the determination of whether the subject has CTCL.

52. The method of claim 51, wherein the CTCL treatment comprises a steroid, interferon, chemotherapy, phototherapy, radiation therapy, or a bone marrow transplant.

53. The method of any one of claims 43-52, wherein the subject has CTCL.

54. The method of any one of claims 43-53, wherein the CTCL comprises mycosis fungoides.

55. The method of any one of claims 43-54, wherein the CTCL comprises Sézary syndrome.

56. The method of any one of claims 43-55, wherein the subject is a human.

57. The method of any one of claims 43-56, wherein the expression level is upregulated compared to a gene expression level of an equivalent gene from a control sample.

58. The method of any one of claims 43-57, wherein the expression level is downregulated compared to a gene expression level of an equivalent gene from a control sample.

59. The method of any one of claims 43-58, wherein the at least one target gene comprises a gene encoding an adapter protein, a gene encoding a tyrosine kinase, a gene encoding an interleukin, a gene encoding a transcription factor, a gene encoding a TNF receptor associated factor protein, a gene encoding a TNF, a gene encoding a TNF superfamily member, a gene encoding a saposin-like protein, a gene encoding a GTP-binding protein, a gene encoding a chromatin associated protein, a gene encoding a G-protein-coupled receptor, a gene encoding a transcriptional coactivator, a gene encoding a spermatogenesis protein, a gene encoding an actin-binding protein, a gene encoding a matrix metalloproteinase, a gene encoding a FYN-binding protein family member, a gene encoding a TEC kinase family member, a gene encoding a STAT, a gene encoding a TRAF3 interacting protein, a gene encoding a dynamin family member, a gene encoding a ubiquitin ligase, a gene encoding a thymocyte selection associated high mobility group box family member, a gene encoding a lymphoid enhancer binding factor family member, a gene encoding a C-C chemokine receptor type family member, a gene encoding an Oct binding factor family member, a gene encoding an gametocyte-specific family member, a gene encoding a plastin family member, a gene encoding a lymphocyte-specific protein tyrosine kinase family member, a gene encoding a member of the NEDD4 family of E3 HECT domain ubiquitin ligases, a gene encoding a C-C motif chemokine ligand family member, a gene encoding a chemokine, or a gene encoding a CXC chemokine, or a combination thereof.

60. The method of any one of claims 43-59, wherein the at least one target gene comprises a gene encoding modulator of cell death, a gene encoding an antimicrobial, a gene encoding a cytokine, or a gene encoding a DNA-binding protein, or a combination thereof 61. The method of any one of claims 43-60, wherein the at least one target gene comprises FYN binding protein (FYB), IL2 inducible T-cell kinase (ITK), interleukin 26 (IL26), signal transducer and activator of transcription 5A (STAT5A), TRAF3 interacting protein 3 (TRAF3IP3), granulysin (GNLY), dynamin 3 (DNM3), or tumor necrosis factor superfamily member 11 (TNFSF11), or a combination thereof.

62. The method of any one of claims 43-61, wherein the at least one target gene comprises TOX, LEF1, CCR4, POU2AF1, GTSF1, PLS3, MMP12, LCK, or NEDD4L, or a combination thereof.

63. The method of any one of claims 43-62, wherein the at least one target gene comprises FYB, GNLY, ITK, STAT5, TRAF3IP3, CXCL10, CXCL8, or TNF, or a combination thereof.

64. The method of any one of claims 43-63, wherein the at least one target gene comprises a gene encoding a microRNA.

65. The method of claim 64, wherein the microRNA comprises miR-21, miR-29b, miR-155, miR-186, miR-214, or miR-221.

66. The method of any one of claims 43-65, further comprising detecting the presence at least one genotype of one more additional target genes known to be mutated in subjects with CTCL, in the nucleic acids or in a separate set of nucleic acids isolated from the skin sample.

67. The method of claim 66, wherein the nucleic acids or the separate set of nucleic acids comprise DNA.

68. The method of claim 66 or 67, wherein determining whether the subject has CTCL further comprises determining whether the subject has CTCL based on the presence of the at least one genotype.

69. The method of any one of claims 66-68, wherein the one or more additional target genes comprise TP53, ZEB1, ARID1A, DNMT3A, CDKN2A, FAS, STAT5B, PRKCQ, RHOA, DNMT3A, PLCG1, or NFKB2.

70. A method of treating a subject with cutaneous T cell lymphoma (CTCL), comprising:
   a) identifying a subject suspected of having CTCL;
   b) isolating nucleic acids from a skin sample obtained from the subject by applying an adhesive patch to a skin region of the subject in a manner sufficient to adhere skin sample cells to the adhesive patch, and removing the adhesive patch from the skin sample in a manner sufficient to retain the adhered skin sample cells to the adhesive patch, wherein the skin sample cells comprise cells from the stratum corneum;
   c) detecting an expression level of at least one target gene known to be upregulated or downregulated in subjects with CTCL, by contacting the isolated nucleic acids with a set of probes that recognize the target gene, and detecting binding between the at least one target gene and the set of probes;
   d) determining whether the subject has CTCL based on the expression level of the at least one target gene; and
   e) administering a CTCL treatment to the subject when the subject is determined to have CTCL based on the expression level of the at least one target gene, and not administering the CTCL treatment to the subject when the subject is not determined to have CTCL based on the expression level of the at least one target gene.

71. The method of claim 70, wherein the nucleic acids comprise mRNA.

72. The method of claim 70 or 71, wherein the cells from the stratum corneum comprise T cells or components of T cells.

73. The method of any one of claims 70-72, wherein the cells from the stratum corneum comprise keratinocytes.

74. The method of any one of claims 70-73, wherein the skin sample does not comprise melanocytes.

75. The method of any one of claims 70-74, wherein the skin sample is obtained by applying a plurality of adhesive patches to the skin region of the subject in a manner sufficient to adhere skin sample cells to each of the adhesive patches, and removing each of the plurality of adhesive patches from the skin region in a manner sufficient to retain the adhered skin sample cells to each of the adhesive patches.

76. The method of any one of claims 70-75, wherein the skin region comprises a skin lesion.

77. The method of any one of claims 70-76, further comprising determining that the subject has CTCL based on the expression level of the at least one target gene.

78. The method of any one of claims 70-77, further comprising administering a CTCL treatment to the subject based on the determination of whether the subject has CTCL.

79. The method of claim 78, wherein the CTCL treatment comprises a steroid, interferon, chemotherapy, phototherapy, radiation therapy, or a bone marrow transplant.

80. The method of any one of claims 70-79, wherein the skin sample comprises a CTCL skin lesion.

81. The method of any one of claims 70-80, wherein the CTCL comprises mycosis fungoides.

82. The method of any one of claims 70-81, wherein the CTCL comprises Sézary syndrome.

83. The method of any one of claims 70-82, wherein the subject is a human.

84. The method of any one of claims 70-83, wherein the expression level is upregulated compared to a gene expression level of an equivalent gene from a control sample.

85. The method of any one of claims 70-84, wherein the expression level is downregulated compared to a gene expression level of an equivalent gene from a control sample.

86. The method of any one of claims 70-85, wherein the at least one target gene comprises a gene encoding an adapter protein, a gene encoding a tyrosine kinase, a gene encoding an interleukin, a gene encoding a transcription factor, a gene encoding a TNF receptor associated factor protein, a gene encoding a TNF, a gene encoding a TNF superfamily member, a gene encoding a saposin-like protein, a gene encoding a GTP-binding protein, a gene encoding a chromatin associated protein, a gene encoding a G-protein-coupled receptor, a gene encoding a transcriptional coactivator, a gene encoding a spermatogenesis protein, a gene encoding an actin-binding protein, a gene encoding a matrix metalloproteinase, a gene encoding a FYN-binding protein family member, a gene encoding a TEC kinase family member, a gene encoding a STAT, a gene encoding a TRAF3 interacting protein, a gene encoding a dynamin family member, a gene encoding a ubiquitin ligase, a gene encoding a thymocyte selection associated high mobility group box family member, a gene encoding a lymphoid enhancer binding factor family member, a gene encoding a C-C chemokine receptor type family member, a gene encoding an Oct binding factor family member, a gene encoding an gametocyte-specific family member, a gene encoding a plastin family member, a gene encoding a lymphocyte-specific protein tyrosine kinase family member, a gene encoding a member of the NEDD4 family of E3 HECT domain ubiquitin ligases, a gene encoding a C-C motif chemokine ligand family member, a gene encoding a chemokine, or a gene encoding a CXC chemokine, or a combination thereof.

87. The method of any one of claims 70-86, wherein the at least one target gene comprises a gene encoding modulator of cell death, a gene encoding an antimicrobial, a gene encoding a cytokine, or a gene encoding a DNA-binding protein, or a combination thereof 88. The method of any one of claims 70-87, wherein the at least one target gene comprises FYN binding protein (FYB), IL2 inducible T-cell kinase (ITK), interleukin 26 (IL26), signal transducer and activator of transcription 5A (STAT5A), TRAF3 interacting protein 3 (TRAF3IP3), granulysin (GNLY), dynamin 3 (DNM3), or tumor necrosis factor superfamily member 11 (TNFSF11), or a combination thereof 89. The method of any one of claims 70-88, wherein the at least one target gene comprises TOX, LEF1, CCR4, POU2AF1, GTSF1, PLS3, MMP12, LCK, or NEDD4L, or a combination thereof.

90. The method of any one of claims 70-89, wherein the at least one target gene comprises FYB, GNLY, ITK, STAT5, TRAF3IP3, CXCL10, CXCL8, or TNF, or a combination thereof.

91. The method of any one of claims 70-90, wherein the at least one target gene comprises a gene encoding a microRNA.

92. The method of claim 91, wherein the microRNA comprises miR-21, miR-29b, miR-155, miR-186, miR-214, or miR-221.

93. The method of any one of claims 70-92, further comprising detecting the presence at least one genotype of one more additional target genes known to be mutated in subjects with CTCL, in the nucleic acids or in a separate set of nucleic acids isolated from the skin sample.

94. The method of claim 92, wherein the nucleic acids or the separate set of nucleic acids comprise DNA.

95. The method of claim 94 or 95, wherein determining whether the subject has CTCL further comprises determining whether the subject has CTCL based on the presence of the at least one genotype.

96. The method of any one of claims 66-68, wherein the one or more additional target genes comprise TP53, ZEB1, ARID1A, DNMT3A, CDKN2A, FAS, STAT5B, PRKCQ, RHOA, DNMT3A, PLCG1, or NFKB2.

EXAMPLES

These examples are provided for illustrative purposes only and not to limit the scope of the claims provided herein.

Example 1

Epidermal skin samples (lesional and non-lesional samples) were collected with non-invasive adhesive patches. Total RNA was extracted from the skin samples on adhesive patches with a silica-coated magnetic bead-based extraction method. qRT-PCR was utilized for measurement of gene expression of both target genes and a house keeping gene.

Quantification of the target expression utilized a Ct measurement of both the target and housekeeping genes measured in parallel in the qRT-PCR, and changes of the target gene expression in test samples were presented as ΔCt, where ΔCt=Ct.target−Ct.housepeeking. A smaller ΔCt value indicates a stronger (or increased) gene expression in the test samples, and vice versa. Changes of the target gene expression in lesional samples compared to control samples (either non-lesional or normal skin samples) were calculated from the ΔCt values of both lesional and control samples, and presented as ΔΔCt, where ΔΔCt=ΔCt.lesion−ΔCt.control. A smaller ΔΔCt indicates a smaller change of the target gene expression between the lesional and control samples, and these changes were presented as fold of changes (FC), calculated from the ΔΔCt value as $FC=2^{-\Delta\Delta Ct}$.

Similar expression patterns or T-cell receptor rearrangements in different lesions from the same subject are indicative of clonality which can also be indicative of the presence of CTCL or helpful in the diagnosis of CTCL.

FIG. 1 illustrates exemplary gene expression biomarkers obtained from skin samples and tested for use as a diagnostic marker. The 'V' denotes genes displaying differential expression between CTCL tumor and normal skin samples, in FFPE tissues from biopsies, as reported in the respective study shown in the top row of the Figure.

FIG. 2 shows the expression results of 17 exemplary genes tested in lesional, non-lesional, and healthy unaffected control skin samples obtained non-invasively via adhesive patches.

Figure 3:
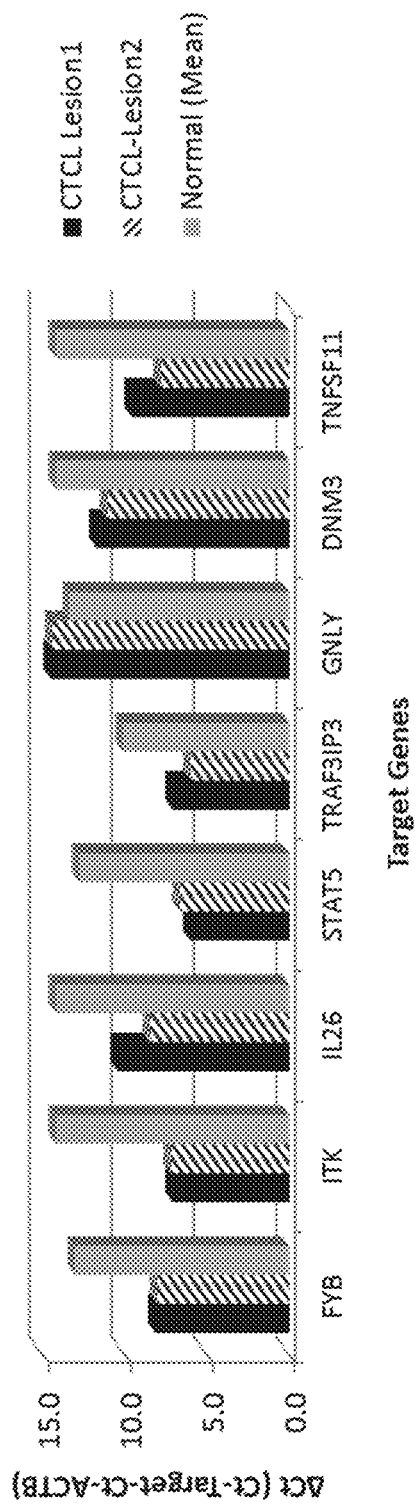
FIG. 3 shows the expression levels of exemplary target genes normalized to housekeeping genes analyzed in parallel (shown as ΔCt (=Ct.target−Ct.HouseKeeping).

FIG. 3 shows the expression levels of exemplary target genes normalized to housekeeping genes analyzed in parallel (shown as ΔCt (=Ct.target−Ct.HouseKeeping).

Figure 4:
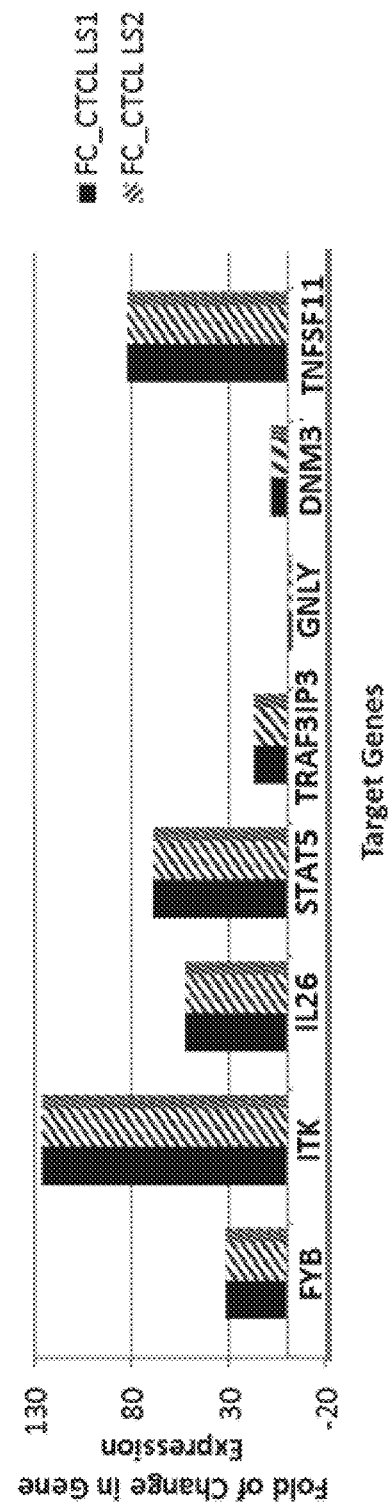
FIG. 4 shows fold change (FC) of the target genes from FIG. 3 in CTCL lesional skin samples compared to healthy unaffected controls (normal skin).
Figure 5:
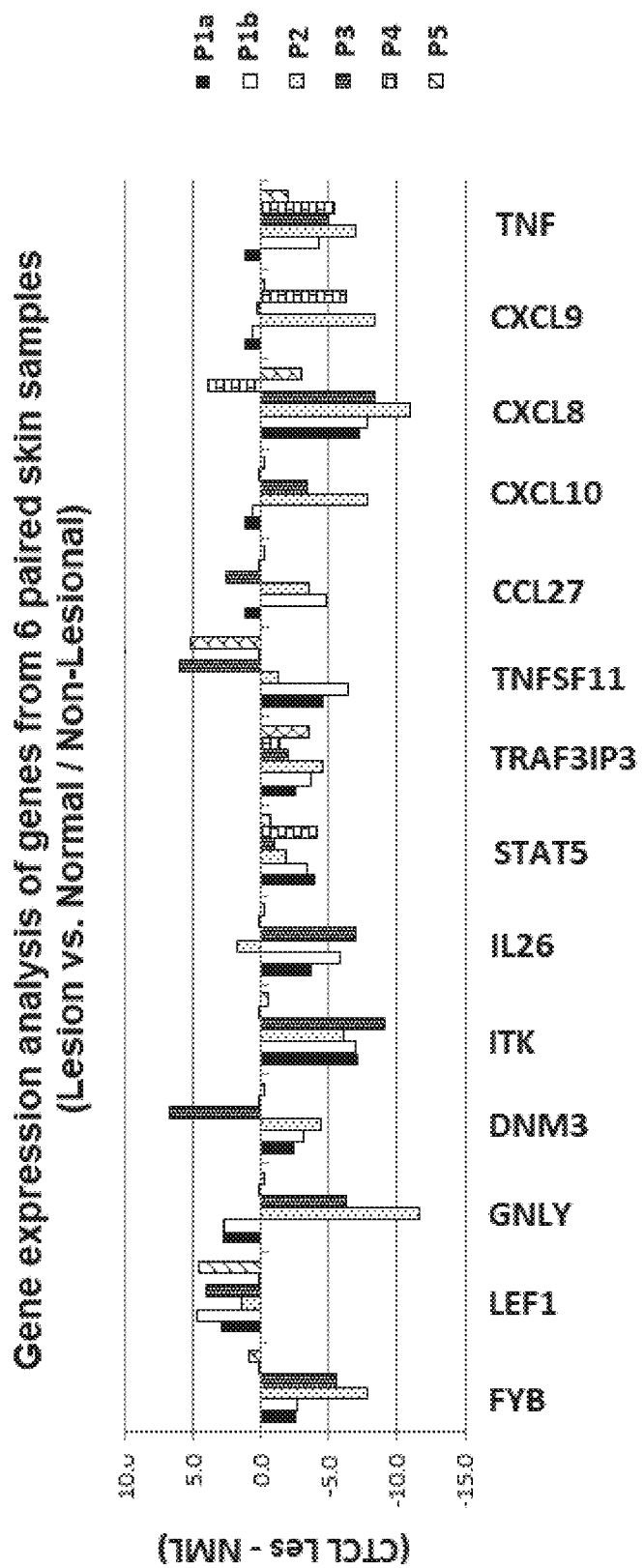
FIG. 5 depicts a gene expression analysis.
Figure 6:
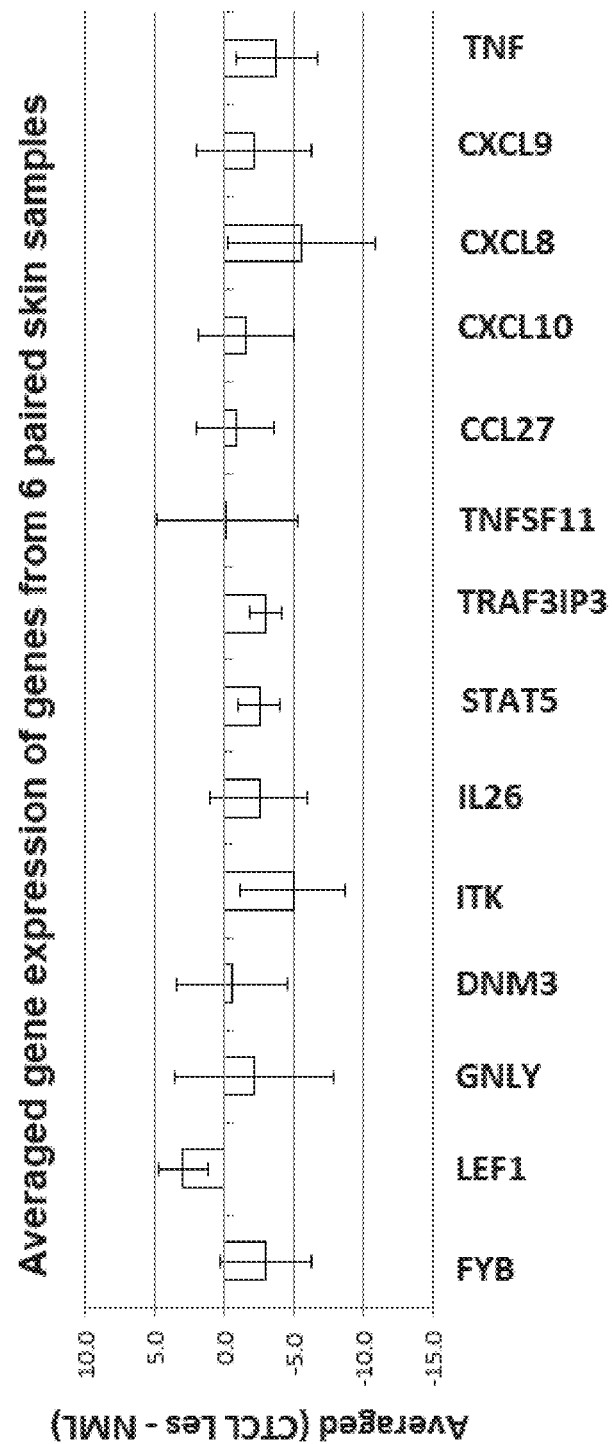
FIG. 6 depicts average gene expression data from lesional and non-lesional skin.

FIG. 4 shows fold change (FC) of the target genes from FIG. 3 in CTCL lesional skin samples compared to healthy unaffected controls (normal skin).

STAT5 shown in FIG. 2-FIG. 4 refers to STAT5A.

Example 2

Additional skin samples, all collected with adhesive patches, were analyzed for gene expression changes by RT-qPCR following the procedures in Example 1. A total of 23 samples were included in the analysis. The samples included 12 CTCL samples and 11 normal skin samples, among which 6 were paired lesional and normal skin samples (i.e. each pair of sample came from one test subject or patient) and the rest were unpaired samples (lesional and normal skin samples from different test subjects).

The gene expression analysis included Ct values of target and housekeeping gene (ACTB) in qPCR from each sample; ΔCt values (=Ct_target−Ct_ACTB), for normalized gene expression levels in each sample; ΔΔCt values (=ΔCt Lesion−ΔCt_NML), for changes in gene expression in lesional skins compared to normal skins in the paired samples (only the paired samples); P-values from statistical analysis of gene expression differences (based on ΔCt values) between the 2 groups of skin samples (lesional vs. normal/non-lesional); statistical analysis (with P-values). Five additional genes were included in the analysis performed in this example. Information relating to the genes in the gene expression analysis is included in FIGS. 8A-8B.

Gene expression data are shown in FIGS. 5-7B. A negative ΔΔCt value indicates an increased gene expression in lesional skin sample. The gene expression data show that 8 tested target genes had p-values below or close to 0.05, indicating that they may be used as target genes. The data indicated that the 8 genes may be used for a CTCL rule-out test. Of the 9 previously picked genes from Example 1, 4 had p-values below 0.05, and 1 had a p-value below 0.1 (p=0.076). Three of the 5 additional genes (compared to Example 1) showed increased gene expression matching increased protein levels reported in CTCL lesional skin samples.

Example 3

Skin samples will be collected with adhesive patches, and analyzed for changes in microRNA expression levels in CTCL lesion samples compared to paired normal skin samples. The expression levels of the following microRNAs will be analyzed to determine which are upregulated or downregulated compared to the control skin samples: miR-21, miR-27b, miR-29b, miR-30c, miR-34a, miR-93, miR-141/200c, miR-142, miR-146, miR-148a, miR-152, miR-155, miR-181a/b, miR-186, miR-203, miR-205, miR-214, miR-221, miR-326, miR-486, miR-663b, and miR-711. In some embodiments, the microRNA comprises miR-21, miR-29b, miR-155, miR-186, miR-214, and miR-221.

MicroRNA data will be grouped into with gene expression data from Example 2 to determine groupings of genes whose expression levels work exceptionally well for differentiating CTCL lesions from non-CTCL samples, compared to the individual gene expression levels.

Example 4

Skin samples will be collected with adhesive patches, and analyzed for the presence and amount of in target gene mutations compared to paired normal skin samples. The mutational status of the following genes will be assessed: TP53, ZEB1, ARID1A, DNMT3A, CDKN2A, FAS, STAT5B, PRKCQ, RHOA, DNMT3A, PLCG1, and NFKB2.

Target gene mutation data will be assessed in combination with gene expression data from Examples 3 and/or 4 to determine groupings of target gene mutations and target gene expression levels that work exceptionally well for differentiating CTCL lesions from non-CTCL samples, compared to individual target gene mutations and expression levels.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating cutaneous T cell lymphoma (CTCL) in a human subject, comprising:
    (a) isolating nucleic acids from a skin sample obtained from the subject by applying at least one adhesive patch to a skin region of the subject in a manner sufficient to adhere skin sample cells to the at least one adhesive patch, and removing the at least one adhesive patch from the skin sample in a manner sufficient to retain the adhered skin sample cells to the at least one adhesive patch, wherein the skin sample cells are substantially free of melanocytes;

(b) measuring gene expression levels of at least one target gene comprising LEF1 by contacting the isolated nucleic acids with at least one probe that recognizes nucleic acids corresponding to the at least one target gene, and detecting binding between the nucleic acids corresponding to the at least one target gene and the at least one probe;

(c) determining that gene expression levels of the at least one target gene are increased at least two-fold compared to a control sample;

(d) identifying the skin sample with the at least two-fold increase in gene expression as being from a CTCL lesion based on the determining; and (e) administering a CTCL treatment comprising a steroid, interferon, chemotherapy, phototherapy, radiation therapy, a bone marrow transplant, or any combination thereof based on the identifying.

2. The method of claim 1, wherein the nucleic acids comprise mRNA.

3. The method of claim 1, wherein the cells comprise T cells or components of T cells.

4. The method of claim 1, wherein the cells comprise keratinocytes.

5. The method of claim 1, wherein applying the at least one adhesive patch to the skin region of the subject in a manner sufficient to adhere skin sample cells to the at least one adhesive patch, and removing the at least one adhesive patch from the skin sample in a manner sufficient to retain the adhered skin sample cells to the at least one adhesive patch comprises applying a plurality of adhesive patches to the skin region of the subject in a manner sufficient to adhere skin sample cells to each adhesive patch of the plurality of adhesive patches, and removing each adhesive patch of the plurality of adhesive patches from the skin region in a manner sufficient to retain the adhered skin sample cells to each adhesive patch of the plurality of adhesive patches.

6. The method of claim 1, wherein the skin region comprises a skin lesion.

7. The method of claim 1, wherein the CTCL comprises mycosis fungoides.

8. The method of claim 1, wherein the CTCL comprises Sézary syndrome.

9. The method of claim 1, wherein the gene expression level is increased as least 10 fold compared to a gene expression level of an equivalent gene from a control sample.

10. The method of claim 1, wherein the at least one target gene further comprises a gene encoding a saposin-like protein, a gene encoding a FYN-binding protein family member, a gene encoding a TEC kinase family member, a gene encoding a STAT, a gene encoding a TRAF3 interacting protein, a gene encoding a CXC chemokine family member, or a combination thereof.

11. The method of claim 1, wherein the at least one target gene further comprises a first gene encoding a DNA-binding protein and one or more of a gene encoding modulator of cell death, a gene encoding an antimicrobial, a gene encoding a cytokine, a second gene encoding a DNA-binding protein, or a combination thereof.

12. The method of claim 1, wherein the at least one target gene comprises at least two target genes.

13. The method of claim 1, wherein the at least one target gene comprises at least three target genes.

14. The method of claim 1, wherein identifying has a specificity of at least 70%.

15. The method of claim 1, wherein identifying has a sensitivity of at least 70%.

16. The method of claim 1, wherein applying the at least one adhesive patch to the skin region does not remove cells from the basal skin layer.

17. The method of claim 1, wherein applying the at least one adhesive patch to the skin region removes cells no deeper than 100 microns from the skin surface.

18. The method of claim 1, wherein applying the at least one adhesive patch to the skin region removes no more than five layers from the stratum corneum.

* * * * *